US010968481B2

(12) United States Patent
van Rooyen et al.

(10) Patent No.: US 10,968,481 B2
(45) Date of Patent: Apr. 6, 2021

(54) GRAPHENE FET DEVICES, SYSTEMS, AND METHODS OF USING THE SAME FOR SEQUENCING NUCLEIC ACIDS

(71) Applicant: Nanomedical Diagnostics, Inc., San Diego, CA (US)

(72) Inventors: Pieter van Rooyen, La Jolla, CA (US); Mitchell Lerner, La Jolla, CA (US); Paul Hoffman, La Jolla, CA (US); Brett R. Goldsmith, San Diego, CA (US)

(73) Assignee: Cardea Bio, Inc., San Diego, CA (US)

( * ) Notice: Subject to any disclaimer, the term of this patent is extended or adjusted under 35 U.S.C. 154(b) by 0 days.

(21) Appl. No.: 16/656,470

(22) Filed: Oct. 17, 2019

(65) Prior Publication Data

US 2020/0181695 A1 Jun. 11, 2020

Related U.S. Application Data

(63) Continuation of application No. 15/483,983, filed on Apr. 10, 2017, now Pat. No. 10,494,670, which is a (Continued)

(51) Int. Cl.
*H01L 29/16* (2006.01)
*G01N 27/414* (2006.01)
(Continued)

(52) U.S. Cl.
CPC ...... *C12Q 1/6869* (2013.01); *B01L 3/502715* (2013.01); *B01L 3/502761* (2013.01);
(Continued)

(58) Field of Classification Search
CPC .......... H01L 29/1606; H01L 29/66015; G01N 27/414; G01N 27/4141; G01N 27/4145; G01N 27/4146; G01N 27/4148
See application file for complete search history.

(56) References Cited

U.S. PATENT DOCUMENTS 9,857,328 B2 * 1/2018 Hoffman ........... H01L 21/76883
10,006,910 B2 * 6/2018 Hoffman ............ G01N 33/5438
(Continued)

OTHER PUBLICATIONS

Xu et al. "Electrophoretic and field-effect graphene for all-electrical DNA array technology", Nature Communications (Sep. 5, 2014): pp. 1-9. (Year: 2014).*

*Primary Examiner* — Michele Fan
(74) *Attorney, Agent, or Firm* — Kunzler Bean & Adamson

(57) ABSTRACT

Chemically-sensitive field effect transistors for biosensor chips and system are disclosed. The itransisitors have a multi-layered structure for performing a set of measurements of a biological reaction involving a binding event for one or more biological analytes that may be label-free. The multilayer structure includes a first insulating layer above a substrate layer and a source electrode and a drain electrode disposed positioned over the first insulating layer; a second insulating layer above the first insulating layer and proximate the source and drain electrodes forming side wall members of a well for a fluid comprising the analytes; a 2D graphene layer forming a channel between source and drain electrodes; a solution gate, formed by fluid flowed over the channel, configured to enable determining differences between one or more sample I-Vg curves having a shifted and changed shape relative to a reference curve; embodiments may include ion-selective membranes and/or ion getters.

20 Claims, 45 Drawing Sheets

Related U.S. Application Data continuation of application No. 15/065,744, filed on Mar. 9, 2016, now Pat. No. 9,618,474, which is a continuation-in-part of application No. 14/963,253, filed on Dec. 9, 2015, now Pat. No. 10,429,342.

(60) Provisional application No. 62/206,228, filed on Aug. 17, 2015, provisional application No. 62/199,987, filed on Aug. 1, 2015, provisional application No. 62/130,621, filed on Mar. 10, 2015, provisional application No. 62/130,598, filed on Mar. 9, 2015, provisional application No. 62/130,604, filed on Mar. 9, 2015, provisional application No. 62/094,016, filed on Dec. 18, 2014.

(51) Int. Cl.
| | | |
|---|---|---|
| *C12Q 1/6869* | (2018.01) | |
| *C12Q 1/6874* | (2018.01) | |
| *B01L 3/00* | (2006.01) | |
| *H01L 27/085* | (2006.01) | |
| *H01L 29/24* | (2006.01) | |

(52) U.S. Cl.
CPC ......... *C12Q 1/6874* (2013.01); *G01N 27/414* (2013.01); *G01N 27/4145* (2013.01); *G01N 27/4146* (2013.01); *G01N 27/4148* (2013.01); *H01L 27/085* (2013.01); *H01L 29/1606* (2013.01); *H01L 29/24* (2013.01); *B01L 2300/0627* (2013.01); *B01L 2300/0858* (2013.01); *B01L 2300/0887* (2013.01); *B01L 2300/12* (2013.01)

(56) References Cited

U.S. PATENT DOCUMENTS

| | | | |
|---|---|---|---|
| 10,429,342 B2* | 10/2019 | Hoffman | H01L 29/1606 |
| 2008/0035494 A1* | 2/2008 | Gomez | B82Y 15/00 |
| | | | 205/792 |
| 2008/0143389 A1* | 6/2008 | Keshavarzi | B82Y 10/00 |
| | | | 326/112 |
| 2009/0008629 A1* | 1/2009 | Matsumoto | B82Y 10/00 |
| | | | 257/24 |
| 2009/0162927 A1* | 6/2009 | Naaman | G11C 13/0014 |
| | | | 435/287.1 |
| 2010/0258787 A1* | 10/2010 | Chae | H01L 29/0895 |
| | | | 257/39 |
| 2013/0214252 A1* | 8/2013 | Park | H01L 21/02527 |
| | | | 257/29 |
| 2013/0234762 A1* | 9/2013 | Han | H01L 29/78684 |
| | | | 327/109 |
| 2017/0200909 A1* | 7/2017 | Sonkusale | H01L 29/1606 |
| 2018/0313784 A1* | 11/2018 | White | H01L 29/127 |

* cited by examiner

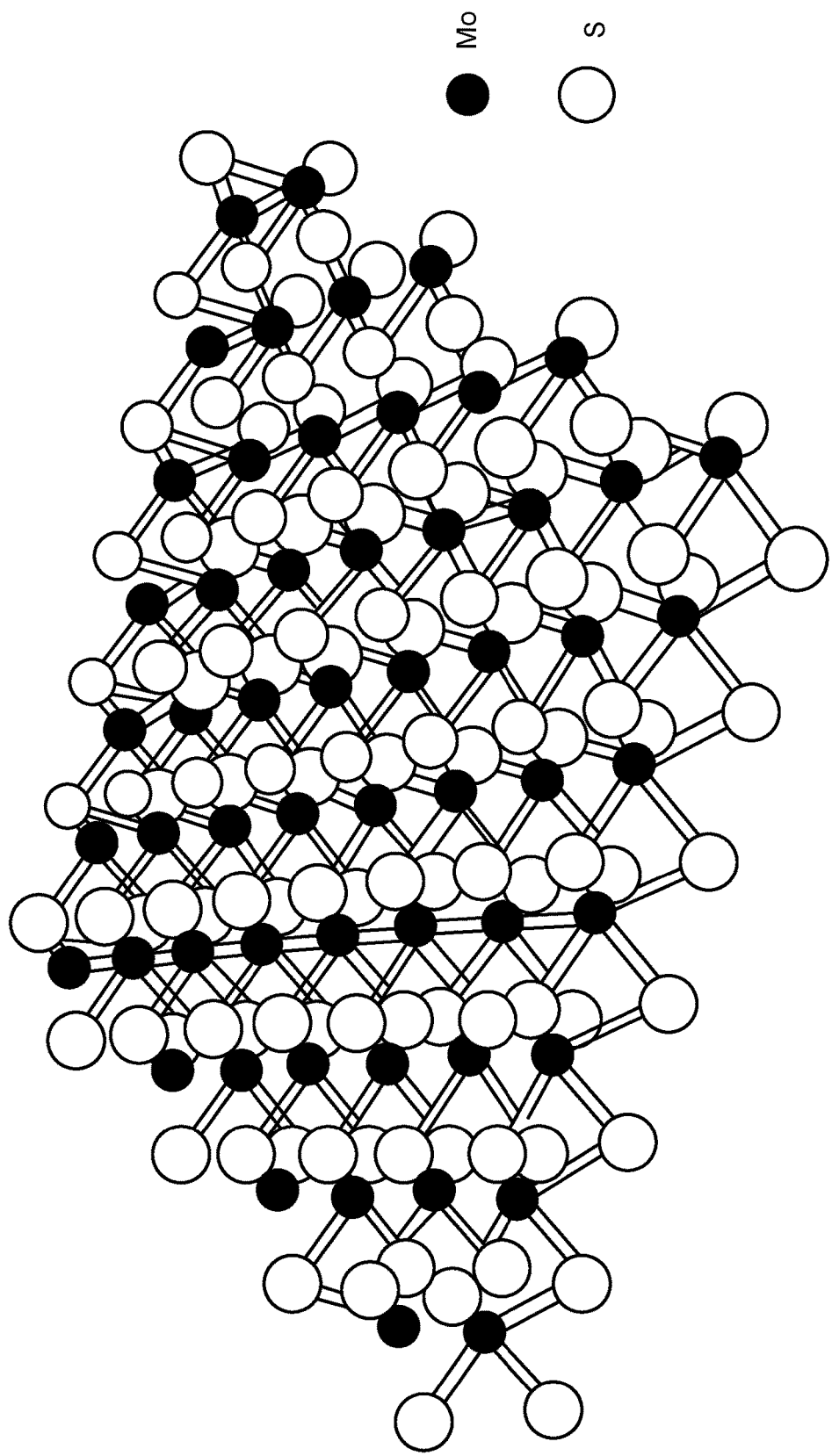

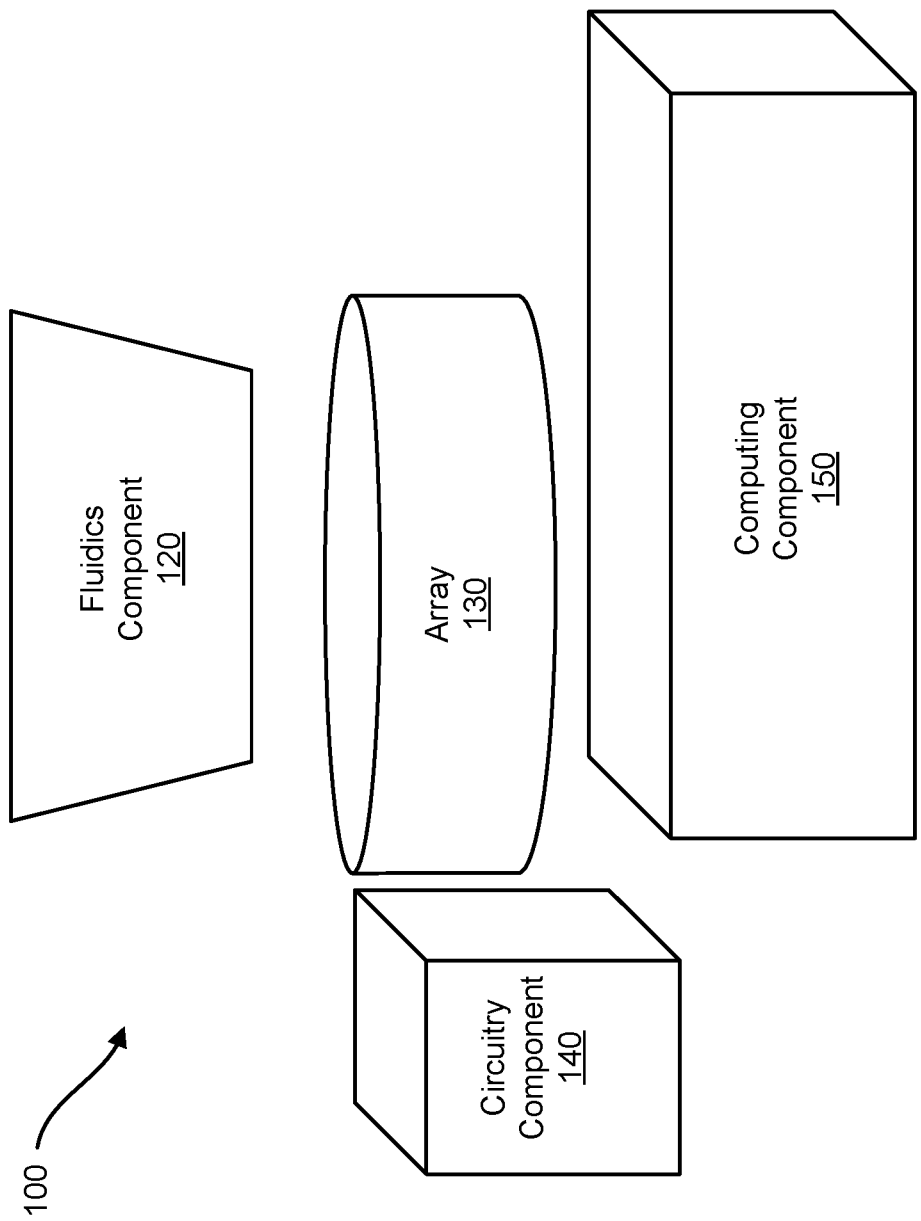

$$I1 = K + aV_g + bV_g^2 + cV_g^3...$$
$$I2 = K + xV_g + yV_g^2 + zV_g^3...$$

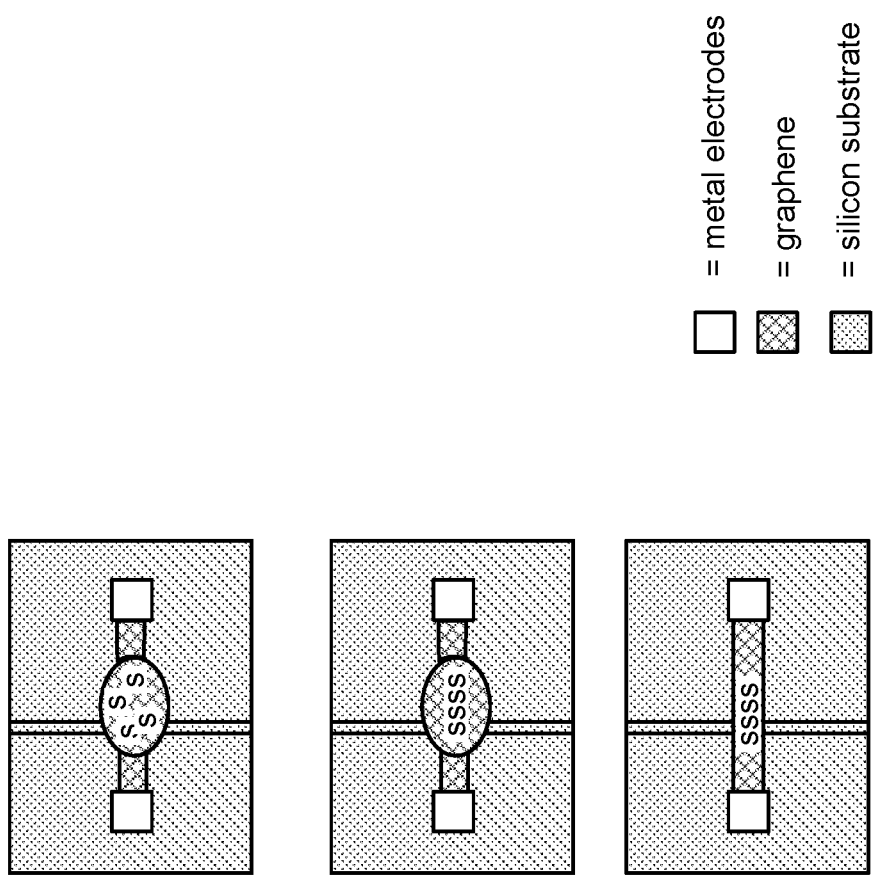

GRAPHENE FET DEVICES, SYSTEMS, AND METHODS OF USING THE SAME FOR SEQUENCING NUCLEIC ACIDS

CROSS-REFERENCE TO RELATED APPLICATIONS

This application is a continuation of U.S. application Ser. No. 15/483,983, filed on Apr. 10, 2017 which is a continuation of U.S. Non-Provisional application Ser. No. 15/065,744, filed on Mar. 9, 2016, now U.S. Pat. No. 9,618,474, which claims the benefit of priority to U.S. Provisional Application Ser. No. 62/130,621, filed on Mar. 10, 2015; U.S. Provisional Application Ser. No. 62/130,598, filed on Mar. 9, 2015; U.S. Provisional Application Ser. No. 62/130,594, filed on Mar. 9, 2015; U.S. Provisional Application No. 62/130,601, filed on Mar. 9, 2015; U.S. Provisional Application Ser. No. 62/094,016, filed on Dec. 18, 2014; and a continuation in part of U.S. application Ser. No. 14/963,253, filed on Dec. 9, 2015, which in turn claims benefit of U.S. Provisional Application Ser. No. 62/206,228, filed on Aug. 17, 2015; U.S. Provisional Application Ser. No. 62/199,987, filed on Aug. 1, 2015; U.S. Provisional Application Ser. No. 62/130,594 and U.S. Provisional Application Ser. No. 62/094,016, filed on Dec. 18, 2014.

FIELD OF THE DISCLOSURE

The present disclosure relates, generally, to field effect transistors, such as integrated field-effect devices, systems including the devices, and methods of using the same for the analysis of biological and/or chemical materials, such as for molecular, e.g., nucleic acid, analysis and/or sequencing. More specifically, the present disclosure relates to field effect transistors having a reaction layer that includes one or two-dimensional materials associated therewith.

BACKGROUND TO THE DISCLOSURE

The sequencing of Nucleic Acids, such as deoxyribonucleic acid (DNA) or Ribonucleic acid (RNA), is a fundamental part of biological discovery. Such sequencing and/or the detection of the same is useful for a variety of purposes and is often used in scientific research, as well as medical advancement. For instance, the genomics and bioinformatics fields are concerned with the application of information technology and computer science to the field of molecular biology. In particular, bioinformatics techniques can be applied to process and analyze various genomic data, such as from an individual so as to determine quantitative and qualitative information about that data that can then be used by various practitioners in the development of diagnostic, prophylactic, and/or therapeutic methods for detecting, preventing, or at least ameliorating diseased states, and thus, improving the safety, quality, and effectiveness of health care. The need for such diagnostic, therapeutic, and prophylactic advancements have led to a high demand for low-cost sequencing, which in turn has driven the development of high-throughput sequencing, termed as Next generation sequencing (NGS).

Generally, the approach to DNA and/or RNA analysis, such as for genetic diagnostics and/or sequencing, involves nucleic acid hybridization and detection. For example, various typical hybridization and detection approaches include the following steps. Particularly, for genetic analysis, a DNA or RNA sample of a subject to be analyzed may be isolated and immobilized on a substrate. In such instances, the immobilized genetic material acts as a template for new nucleic acid synthesis. A probe of a known sequence identity, e.g., a disease marker, may be labeled and washed across the substrate. If the disease marker is present, a binding event will occur, e.g., hybridization, and because the probe has been labeled the hybridization event may either be or not be detected thereby indicating the presence or absence of the disease marker in the subject's sample.

For DNA sequencing, first, an unknown nucleic acid sequence to be identified, e.g., a single-stranded sequence of DNA of a subject, composed of a combination of unknown nucleotides, e.g., As, Cs, Gs, and Ts, is isolated, amplified, and immobilized on the substrate. Next, a known nucleotide labeled with an identifiable tag is contacted with the unknown nucleic acid sequence in the presence of a polymerase. When hybridization occurs, the labeled nucleotide binds to its complementary base in the unknown sequence immobilized on the surface of the substrate. The binding event can then be detected, e.g., optically or electrically. These steps are then repeated until the entire DNA sample has been completely sequenced, e.g., sequencing by synthesis. Typically, these steps are performed by a Next Gen Sequencer wherein thousands to millions of sequences may concurrently be produced in the next-generation sequencing process.

For example, a central challenge in DNA sequencing is assembling full-length genomic sequence data, e.g., of chromosomal sequences, from a sample of genetic material obtained from a subject. Particularly, such assembling includes one or more genomic analysis protocols, such as employing a mapping and/or an aligning algorithm, and involves mapping and aligning a fragment of identified sample sequence to a reference genome, yielding sequence data in a format that can be compared to a reference genomic sequence, such as to determine the variants in the sampled full-length genomic sequences. In particular, the methods employed in sequencing protocols do not produce full-length chromosomal sequences of the sample DNA.

Rather, in a typical sequencing protocol, sequence fragments, typically from 100-1,000 nucleotides in length, are produced without any indication as to where in the genome they map and align. Therefore, in order to generate full-length chromosomal genomic constructs, or determine their variance with respect to a reference genomic sequence, these fragments of DNA sequences need to be mapped, aligned, merged, and/or compared to the reference genomic sequence. Through such processes the variants of the sample genomic sequences from the reference genomic sequences may be determined.

However, as the human genome is comprised of approximately 3.1 billion base pairs, and as each sequence fragment is typically only from about 100 to 500 to 1,000 nucleotides in length, the time and effort that goes into building such full length genomic sequences and determining the variants therein is quite extensive, often requiring the use of several different computer resources applying several different algorithms over prolonged periods of time. In a particular instance, thousands to millions of fragments or even billions of DNA sequences are generated, mapped, aligned, and merged in order to construct a genomic sequence that approximates a chromosome in length. A step in this process may include comparing the sequenced DNA fragments to a reference sequence so as to determine where in the genome the fragments align.

In such instances, the raw genetic material must be processed so as to derive usable genetic sequence data therefrom. This processing may be done manually or via an automated sequencer. Typically, such processing involves obtaining a biological sample from a subject, such as through venipuncture, hair, etc. and treating the sample to isolate the DNA therefrom. Once isolated the DNA may be denatured, strand separated, and/or portions of the DNA may then be multiplied, e.g., via polymerase chain reaction (PCR), so as to build a library of replicated strands that are now ready to be sequenced, e.g., read, such as by an automated sequencer, which sequencer is configured to "read" the replicate strands, e.g., by synthesis, and thereby determine the nucleotide sequences that makes up the DNA. Further, in various instances, such as in building the library of replicated strands, it may be useful to provide for over-coverage when preprocessing a given portion of the DNA. To perform this over-coverage, e.g., using PCR, may require increased sample preparation resources and time, and therefore be more expensive, but it often gives an enhanced probability of the end result being more accurate.

More particularly, once the library of replicated strands has been generated they may be injected into an automated sequencer that may then "read" the strands, such as by synthesis, so as to determine the nucleotide sequences thereof. For instance, the replicated single stranded DNA may be attached to a glass bead and inserted into a test vessel, e.g., an array. All the necessary components for replicating its complementary strand, including labeled nucleotides, are also added to the vessel but in a sequential fashion. For example, all labeled "A", "C", "G", and "T's" are added, either one at a time or all together to see which of the nucleotides is going to bind at position one. After each addition a light, e.g., a laser, is shone on the array. If the composition fluoresces then an image is produced indicating which nucleotide bound to the subject location. More particularly, where the nucleotides are added one at a time, if a binding event occurs, then its indicative fluorescence will be observed. If a binding event does not occur, the test vessel may be washed and the procedure repeated until the appropriate one of the four nucleotides binds to its complement at the subject location, and its indicative fluorescence is observed. Where all four nucleotides are added at the same time, each may be labeled with a different fluorescent indicator, and the nucleotide that binds to its complement at the subject position may be determined, such as by the color of its fluorescence. This greatly accelerates the synthesis process.

Once a binding event has occurred, the complex is then washed and the synthesis steps are repeated for position two. For example, a marked nucleotide "A" may be added to the mix to determine if the complement at the position is a "T", and if so, all the sequences having that complement will bind to the labeled "T" and will therefore fluoresce, and the samples will all be washed. Where the binding happened the bound nucleotide is not washed away, and then this will be repeated for all positions until all the over-sampled nucleic acid segments, e.g., reads, have been sequenced and the data collected. Alternatively, where all four nucleotides are added at the same time, each labeled with a different fluorescent indicator, only one nucleotide will bind to its complement at the subject position, and the others will be washed away, such that after the vessel has been washed, a laser may be shone on the vessel and which nucleotide bound to its complement may be determined, such as by the color of its fluorescence. This continues until the entire strand has been replicated in the vessel.

A typical length of a sequence replicated in this manner is from about 100 to about 500 base pairs, such as between 150 to about 400 base pairs, including from about 200 to about 350 base pairs, such as about 250 base pairs to about 300 base pairs dependent on the sequencing protocol being employed. Further, the length of these segments may be predetermined, e.g., engineered, to accord with any particular sequencing machinery and/or protocol by which it is run. The end result is a readout, or read, that is comprised of a replicated DNA segment, e.g., from about 100 to about 1,000 nucleotides in length, that has been labeled in such a manner that every nucleotide in the sequence, e.g., read, is known because of its label. Hence, since the human genome is comprised of about 3.1 billion base pairs, and various known sequencing protocols usually result in labeled replicated sequences, e.g., reads, from about 100 or 101 bases to about 250 or about 300 or about 400 bases, the total amount of segments that need to be sequenced, and consequently the total number of reads generated, can be anywhere from about 10,000,000 to about 40,000,000, such as about 15,000,000 to about 30,000,000, dependent on how long the label replicated sequences are. Therefore, the sequencer may typically generate about 30,000,000 reads, such as where the read length is 100 nucleotides in length, so as to cover the genome once.

However, in part, due to the need for the use of optically detectable, e.g., fluorescent, labels in the sequencing reactions being performed, the required instrumentation for performing such high throughput sequencing is bulky, costly, and not portable. For this reason, a number of new approaches for direct, label-free detection of DNA hybridization reactions have been proposed. For instance, among the new approaches are detection methods that are based on the use of various electronic analytic devices. Such direct electronic detection methods have several advantages over the typical NGS platform. For example, the detector may be incorporated in the substrate itself, such as employing a biosystem-on-a-chip device, such as a complementary metal oxide semiconductor device, "CMOS". More particularly, in using a CMOS device in genetic detection, the output signal representative of a hybridization event can be directly acquired and processed on a microchip. In such an instance, automatic recognition is theoretically achievable in real time and at a lower cost than is currently achievable using NGS processing. Moreover, standard CMOS devices may be employed for such electronic detection making the process simple, inexpensive, and portable.

However, in order for next-generation sequencing to become widely used as a diagnostic in the healthcare industry, sequencing instrumentation will need to be mass produced with a high degree of quality and economy. One way to achieve this is to recast DNA sequencing in a format that fully leverages the manufacturing base created for computer chips, such as complementary metaloxide semiconductor (CMOS) chip fabrication, which is the current pinnacle of large scale, high quality, low-cost manufacturing of high technology. To achieve this, ideally the entire sensory apparatus of the sequencer could be embodied in a standard semiconductor chip, manufactured in the same fab facilities used for logic and memory chips. Recently, such a sequencing chip, and the associated sequencing platform, has been developed and commercialized by Ion Torrent, a division of Thermo-Fisher, Inc. The promise of this idea has not been realized commercially due to the fundamental limits of applying a metal oxide semiconductor field effect transistor, or MOSFET, as a biosensor. When a MOSFET is used in solution as a biosensor, it is referred to as an ISFET. A particular limitation, however, includes a lack of sensor sensitivity and signal to noise characteristics as the semiconductor node scales down to lower geometries of the transistor (gate length).

More particularly, a field effect transistor, FET, typically includes a source electrode and a drain electrode together forming a gate, and further including a channel region connecting the source and drain electrodes. The FET may also include an insulating barrier separating the gate from the channel. The operation of a conventional FET relies on the control of the channel conductivity, and thus the drain current, by a voltage, VGS, applied between the gate and source. For high-speed applications, and for the purposes of increasing sensor sensitivity, FETs should respond quickly to variations in VGS. However, this requires short gates and fast carriers in the channel.

Unfortunately, FETs with short gates frequently suffer from degraded electrostatics and other problems (collectively known as short channel effects), such as threshold-voltage roll-off, drain-induced barrier lowering, and impaired drain-current saturation, results in a decrease in sensor sensitivity. However, scaling theory predicts that a FET with a thin barrier and a thin gate-controlled region (measured in the vertical direction) will be robust against short-channel effects down to very short gate lengths (measured in the horizontal direction). Nevertheless, these effects make the use of such technologies difficult to employ in sequencing reactions.

Accordingly, the possibility of having channels that are very thin in the vertical dimension would allow for high-speed transmission of carriers as well as for increased sensor sensitivity and accuracy. What is needed, therefore, is a FET device that is configured in such a manner as to include a shorter gate than is currently achievable in present FET applications, which will allow such technologies to be fully deployed in sequencing reactions. Hence, a solution that includes such a FET device designed for use in biological applications, such as for nucleic acid sequencing and/or genetic diagnostics would especially be beneficial.

SUMMARY OF THE DISCLOSURE

Provided herein are devices, systems, and methods of employing the same for the performance of genomics and/or bioinformatics analysis. The devices, systems, and methods of the disclosure are directed in part to field effect transistor (FET) sensors, integrated circuits, and arrays employing the same for analyte measurements. The present FET sensors, arrays, and integrated circuits may be fabricated using conventional CMOS processing techniques based on improved FET sensor and array designs that increase measurement sensitivity and accuracy, and at the same time facilitate significantly small sensor sizes and dense gFET sensor based arrays. Particularly, improved fabrication techniques, as well as improved sensor devices, and their use, employing 1D or 2D reaction layers, provide for rapid data acquisition from small sensors to large, including dense arrays of sensors.

Such arrays may be employed to detect the presence of an analyte, changes in analyte concentration, and/or the identity of various analyte types in a wide variety of chemical and/or biological processes, including DNA hybridization and/or sequencing reactions. More particularly, presented herein are FET based sensor arrays that have been configured to facilitate DNA hybridization and sequencing techniques, as well as the resultant detection of the same, which take place proximate a reaction zone that has been adapted to include a 1D or 2D surface element. Specifically, in various embodiments, complementary metaloxide semiconductor (CMOS) field effect transistor (FET) devices are provided, where the devices include a plurality of reaction zones that have been adapted to have a 1D or 2D surface characteristic associated therewith so as to decrease sensor length at the same time as increasing sensor sensitivity. In such instances, the devices may include a number of reaction zones that have been configured to receive a solution containing one or more reactants that when conditions are such to favor a reaction result in a detectable product.

Accordingly, presented herein are improved bio-chemical sensor devices that are configured for detecting changes in a solution that result from the occurrence of a binding event between two reactants proximate a reaction zone of the device. In particular instances, the detectable changes may be based on monitoring fluctuations in hydrogen ion concentration (pH), variations in analyte concentration, and/or binding events associated with chemical processes relating to DNA synthesis, such as within a gated reaction chamber of a 1D or 2D based biosensor chip. More specifically, the present disclosure is at least in part directed to a chemically-sensitive field-effect transistor for analysis of biological or chemical materials that solves many of the current problems associated with nucleic acid sequencing and genetic diagnostics. Methods of fabricating such devices as well as their use in the performance of biochemical reactions are also provided.

For instance, in one aspect of the present disclosure, a chemically-sensitive transistor, such as a field effect transistor (FET) that is fabricated on a primary structure, such as a wafer, e.g., a silicon wafer, is provided. In various instances, the primary structure may include one or more additional structures, for instance, in a stacked configuration, such as including at least an insulator material layer. For example, the primary structure may include a secondary structure, such as an insulator material, which may be included on top of, or otherwise be associated with, the primary structure, and may be an inorganic material, such as a silicon oxide, e.g., a silicon dioxide, or a silicon nitride, or an organic material, such as a polyimide, BCB, or other like material.

The secondary structure and/or insulator layer may include a further structure containing one or more of a conductive source and/or a conductive drain, such as separated one from another by a space, and embedded in the primary and/or secondary structure materials and/or may be planar with a top surface of the insulator. In various instances, the structures may further include a processor, such as for processing generated data, such as sensor-derived data. Accordingly, the structures may be configured as, or otherwise include, an integrated circuit, and/or may be an ASIC, a structured ASIC, or an FPGA. In particular instances, the structures may be configured as a complementary metal-oxide semiconductor (CMOS), which in turn may be configured as a chemically-sensitive FET containing one or more of a conductive source, a conductive drain, a gate, and/or a processor. For instance, the FET may include a CMOS configuration having an integrated circuit that is fabricated on a silicon wafer, which may further be adapted to include an insulator layer. In such an instance, the insulator layer may include the conductive source and drain such as where the source and drain are composed of metal, such as a damascene copper source and a damascene copper drain.

In various instances, one or more of the structures may include a surface, e.g., a top surface, which surface may include a channel, such as where the surface and/or channel may be configured to extend from the conductive source to the conductive drain. An exemplary length of the surface and/or channel from the source to the drain may range from about 0.001 microns to about 10 microns, such as from about 0.01 microns to about 5 microns, for instance, from about 0.05 micron to 3 microns, including about 0.1 or about 0.5 microns to about 1 or about 1.5 or about 2 microns in the horizontal and/or vertical directions. An exemplary width of the surface and/or channel from side to side may range from about 0.001 microns to about 10 microns, such as from about 0.01 microns to about 5 microns, for instance, from about 0.05 microns to 3 microns, including about 0.1 or 0.5 microns to about 1 or about 1.5 or about 2 microns.

In certain instances, the surface and/or channel may include a one-dimensional transistor material, a two-dimensional transistor material, a three-dimensional transistor material, and/or the like. In various instances, a one-dimensional (1D) transistor material may be included, which 1D material may be composed of a carbon nanotube or a semiconductor nanowire. In various instances, a two-dimensional (2D) transistor material may be included, which 2D material may be composed of a graphene layer, silicene, molybdenum disulfide, black phosphorous, and/or metal dichalcogenides. In various instances, the surface and/or channel may further include a dielectric layer. In particular instances, the surface and/or channel may include a graphene layer.

Additionally, in various instances, a reaction layer, e.g., an oxide layer, may be disposed on the surface and/or channel, such as layered or otherwise deposited on the 1D, 2D, e.g., graphene, or 3D layer, or the dielectric layer. Such an oxide layer may be an aluminum oxide or a silicon oxide, such as silicon dioxide. In some embodiments, the oxide layer may have a thickness of about 20 nanometers, such as about 15 nanometers, such as 10 or 9 or 7 or 5 nanometers or less. In various instances, a passivation layer may be disposed on the surface and/or channel, such as layered or otherwise deposited on the 1D, 2D, or 3D layer and/or on an associated reaction layer on the surface and/or channel. Such a passivation layer may have a thickness of about 0.5 microns or less, such as about 0.1 microns or about 50 nanometers or about 20 nanometers, such as about 15 nanometers, such as 10 or 9 or 7 or 5 nanometers or less.

In particular instances, the primary and/or secondary structures may be fabricated or otherwise configured so as to include a chamber or well structure in and/or on the surface. For instance, a well structure may be positioned on a portion of a surface, e.g., an exterior surface, of the primary and/or secondary structures. In some instances, the well structure may be formed on top of, or may otherwise include, at least a portion of the 1D, 2D, and/or 3D material, and/or may additionally include the reaction, e.g., oxide, and/or passivation layers. In various instances, the chamber and/or well structure may define an opening, such as an opening that allows access to an interior of the chamber, such as allowing direct contact with the 1D, e.g., carbon nanotube or nanowire, 2D, e.g., graphene, surface and/or channel. In such instances, the FET device may be configured as a solution gated sensor device.

Accordingly, a further aspect of the present disclosure is a bio-sensor. The bio-sensor includes a CMOS structure that may include a metal containing source, e.g., a damascene copper source, as well as a metal containing drain, e.g., a damascene copper drain, a 1D or 2D layered, e.g., a graphene layered, surface or channel extending from the source to the drain, and a well or chamber structure that may be positioned on a portion of an exterior surface of the 1D or 2D layered well. In particular instances, the well structure may be configured so as to define an opening that allows for direct, fluidic contact with the 1D, e.g., nanotube, nanowire, and/or 2D, e.g., graphene, well or chamber surface. In various instances, an oxide and/or passivation layer may be disposed in or on the chamber surfaces. Hence, in certain instances, a chemically-sensitive transistor, such as a field effect transistor (FET) including one or more nano- or micro-wells may be provided.

In some embodiments, the chemically-sensitive field effect transistor may include a plurality of wells and may be configured as an array, e.g., a sensor array. Such an array or arrays may be employed such as to detect a presence and/or concentration change of various analyte types in a wide variety of chemical and/or biological processes, including DNA hybridization and/or DNA or RNA sequencing reactions. For instance, the devices herein described and/or systems including the same may be employed in a method for the analysis of biological or chemical materials, such as for whole genome analysis, genome typing analysis, microarray analysis, panels analysis, exome analysis, micro-biome analysis, and/or clinical analysis, such as cancer analysis, NIPT analysis, and/or UCS analysis. In a particular embodiment, one or more surfaces within the wells of the field effect transistor may be configured as a reaction zone, which reaction zone may include an additional structure, such as a graphene layer, and hence, the FET may be a graphene FET (gFET) array.

Such FET sensors as herein described may be employed to facilitate DNA hybridization and/or sequencing techniques, such as based on monitoring changes in hydrogen ion concentration (pH), changes in other analyte concentrations, and/or binding events associated with chemical processes (e.g., relating to DNA synthesis), such as within a gated reaction chamber or well of the gFET based sensor, such as proximate the reaction zone(s). For example, the chemically-sensitive field effect transistor may be configured as a CMOS biosensor and/or may be adapted to increase the measurement sensitivity and/or accuracy of the sensor and/or associated array(s), such as by including one or more surfaces or wells having a surface layered with a 1D and/or 2D and/or 3D material, a dielectric or reaction layer, a passivation layer, and the like. In particular instances, the increased sensitivity of the sensors may, in part, be due to the presence of the presence of the 1D or 2D material, and/or further enhanced by its relationship to one or more of the reaction and/or passivation layers, which in turn allows for smaller sensor configurations, therefore smaller channels and/or gates, and thus a greater density of sensors and/or arrays.

For instance, in a particular embodiment, a chemically-sensitive graphene containing field effect transistor (gFET), such as a gFET having a CMOS structure is provided, where the gFET sensor, e.g., biosensor, may include an oxide and/or passivation layer, such as a layer that is disposed on the surface of the well or chamber so as to increase the measurement sensitivity and/or accuracy of the sensor and/or associated array(s). The oxide layer, when present, may be composed of an aluminum oxide, a silicon oxide, a silicon dioxide, and the like. More particularly, the oxide and/or passivation layers may have a suitable thickness such as of from about 100 nm to about 75 nm, such as from about 50 nm to about 30 nm, from about 40 nm to about 25 nm, such as from about 20 nm to about 10 nm or 9 nm or less, respectively.

In another aspect, the present FET integrated circuits, sensors, and/or arrays of the disclosure may be fabricated such as using any suitable complementary metal-oxide semiconductor (CMOS) processing techniques known in the art. In certain instances, such a CMOS processing technique may be configured to increase the measurement sensitivity and/or accuracy of the sensor and/or array, and at the same time facilitate significantly small gates having relatively smaller sensor sizes and more dense FET chamber sensor regions. Particularly, in various embodiments, the improved fabrication techniques herein described result in sensor devices containing reaction zones employing a 1D, 2D, 3D layers, and may further be manufactured and/or otherwise treated so as to contain one or more additional reaction layers, such as an oxide and/or passivation layers, which structures, along or in combination provide for rapid data acquisition, such as from small sensors to large and dense arrays of sensors. In certain embodiments, one or more of such layers may be fabricated along with the manufacture of the array, such as via one or more chemical vapor deposition techniques. Additionally, in particular embodiments, an ion-selective permeable membrane may be included, such as where the membrane layer may include a polymer, such as a perfluorosulphonic material, a perfluorocarboxylic material, PEEK, PBI, Nafion, and/or PTFE. In some embodiments, the ion-selective permeable membrane may include an inorganic material, such as an oxide or a glass. In more particular embodiments, one or more of the various layers, e.g., the reaction, passivation, and/or permeable membrane layers may be fabricated or otherwise applied by a spin-coating, anodization, PVD, and/or sol gel method.

In a further aspect, a system is provided, such as a system configured for running one or more reactions so as to detect a presence and/or concentration change of various analyte types in a wide variety of chemical and/or biological processes, including DNA hybridization and/or sequencing reactions. As such, the system may include an array including one or more, e.g., a plurality of sensors, such as where each of the sensors includes a chemically-sensitive field-effect transistor having a conductive source, a conductive drain, and a reaction surface or channel extending from the conductive source to the conductive drain. In particular instances, the array may include one or more wells configured as one or more reaction chambers having the reaction surface or channel positioned therein. In some instances, the surface and/or channel of the chamber may include a one-dimensional (1D) or two-dimensional (2D) transistor material, a dielectric or reaction layer, a passivation layer, and/or the like.

The system may further include one or more of a fluidic component, such as for performing the reaction, a circuitry component, such as for running the reaction processes, and/or a computing component, such as for controlling and/or processing the same. For instance, a fluidics component may be included where the fluidic component is configured to control one or more flows of reagents over the array and/or one or more chambers thereof. Particularly, in various embodiments, the system includes a plurality of reaction locations, such as surfaces or wells, which in turn includes a plurality of sensors and/or a plurality of channels, and further includes one or more fluid sources containing a fluid having a plurality of reagents and/or analytes for delivery to the one or more surfaces and/or wells for the performance of one or more reactions therein. In certain instances, a mechanism for generating one or more electric and/or magnetic fields is also included.

The system may additionally include a circuitry component, such as where the circuitry component may include a sample and hold circuit, an address decoder, a bias circuitry, and/or at least one analog-to-digital converter. For instance, the sample and hold circuit may be configured to hold an analog value of a voltage to be applied to or on a selected column and/or row line of an array of a device of the disclosure, such as during a read interval. Additionally, the address decoder may be configured to create column and/or row select signals for a column and/or row of the array, so as to access a sensor with a given address within the array. The bias circuitry may be coupled to one or more surfaces and/or chambers of the array and include a biasing component such as may be adapted to apply a read and/or bias voltage to selected chemically-sensitive field-effect transistors of the array, e.g., to a gate terminal of the transistor. The analog to digital converter may be configured to convert an analog value to a digital value A computing component may also be included, such as where the computing component may include one or more processors, such as a signal processor; a base calling module, configured for determining one or more bases of one or more reads of a sequenced nucleic acid; a mapping module, configured for generating one or more seeds from the one or more reads of sequenced data and for performing a mapping function on the one or more seeds and/or reads; an alignment module, configured for performing an alignment function on the one or more mapped reads; a sorting module, configured for performing a sorting function on the one or more mapped and/or aligned reads; and/or a variant calling module, configured for performing a variant call function on the one or more mapped, aligned, and/or sorted reads. In particular instances, the base caller of the base calling module may be configured to correct a plurality of signals, such as for phase and signal loss, to normalize to a key, and/or to a generate a plurality of corrected base calls for each flow in each sensor to produce a plurality of sequencing reads. In various instances, the device and/or system may include at least one reference electrode.

Particularly, the system may be configured for performing a sequencing reaction. In such an instance, the FET sequencing device may include an array of sensors having one or more chemically-sensitive field-effect transistors associated therewith. Such transistors may include a cascode transistor having one or more of a source terminal, a drain terminal, and or a gate terminal, such as composed of a damascene copper. In such an instance, the source terminal of the transistor may be directly or indirectly connected to the drain terminal of the chemically-sensitive field-effect transistor. In some instances, a one or two dimensional channel or other suitably configured surface element may be included and may extend from the source terminal to the drain terminal, such as where the 1D channel material may be a carbon nanotube or nanowire, and the two-dimensional channel material may be composed of graphene, silicene, a phosphorene, a molybdenum disulfide, and a metal dichalcogenide. The device may further be configured to include a plurality of column and row lines coupled to the sensors in the array of sensors. In such an instance, each column line in the plurality of column lines may be directly or indirectly connected to or otherwise coupled to the drain terminals of the transistors, e.g., cascode transistors, of a corresponding plurality of sensors and/or pixels in the array, and likewise each row line in the plurality of row lines may be directly or indirectly connected to or otherwise coupled with the source terminals of the transistors, e.g., cascode transistors, of a corresponding plurality of sensors in the array.

In some instances, a plurality of source and drain terminals having a plurality of reaction surfaces, e.g., channel members, extended there between may be included, such as where each channel member includes a one or two or even three dimensional material. In such an instance, a plurality of first and/or second conductive lines, and so forth, may be coupled to the first and second source/drain terminals of the chemically-sensitive field-effect transistors in respective columns and rows in the array, and so forth. Additionally, control circuitry may be provided and coupled to the plurality of column and row lines such as for reading a selected sensor connected to a selected column line and/or a selected row line. The circuitry may also include a biasing component having a bias circuitry such as is configured to apply a read voltage, while the sample and hold circuit may be configured to hold an analog value of a voltage on a selected column line of the array during a read interval. Particularly, the bias circuitry may be configured for applying a read voltage to the selected row line, and/or to apply a bias voltage such as to the gate terminal of a transistor, such as FET and/or cascode transistor of the selected sensor. In a particular embodiment, the bias circuitry may be coupled to one or more chambers of the array and be configured to apply a read bias to selected chemically-sensitive field-effect transistors via the conductive column and/or row lines. Particularly, the bias circuitry may be configured to apply a read voltage to the selected row line, and/or to apply a bias voltage to the gate terminal of the transistor, e.g., cascode transistor, such as during a read interval.

A sense circuitry may also be included and coupled to the array so as to sense a charge coupled to one or more of the gate configurations of a selected chemically-sensitive field-effect transistor. The sense circuitry may be configured to read the selected sensor based on a sampled voltage level on the selected row and/or column line. In such an instance, the sense circuitry may include one or more of a pre-charge circuit, such as to pre-charge the selected column line to a pre-charge voltage level prior to the read interval; and a sample circuit such as to sample a voltage level at the drain terminal of the selected transistor, such as during the read interval. A sample circuit may further be included and contain a sample and hold circuit configured to hold an analog value of a voltage on the selected column line during the read interval, and may further include an analog to digital converter to convert the analog value to a digital value.

In particular embodiments, the computer component of the FET, e.g., CMOS, structure may include a processor configured for controlling the performance of one or more reactions involving a biological or chemical material so as to obtain reaction results, and for analyzing those results, for instance, based on detecting and/or measuring changes in a voltage (V) potential, current (I), or capacitance occurring on the chemically-sensitive field effect transistor. Particularly, the processor, such as a signal processor, may be configured so as to generate one or more current (I) vs. voltage (V) curves, such as where the current I of the I-V curve is the current applied between the source and drain of the chemically sensitive field effect transistor and/or where the gate voltage (Vg) of the I-Vg curve is a gate or channel voltage applied to the chemically-sensitive field effect transistor. In such an instance, the gate voltage Vg of the I-Vg curve is a top and/or a back gate voltage that may be applied to the chemically sensitive field effect transistor through a top (or front) and/or back of the device, respectively. Hence, a suitably configured device of the disclosure may be adapted as a front and/or back-gated device, which may further be configured as a solution gate. Accordingly, in various embodiments, a device of the disclosure may be a field-effect transistor that includes a chamber adapted for measuring ion concentrations in a solution; such as where, when the ion concentration (such as $H^+$ or $OH^-$ in a pH scale) within the chamber changes, the current through the transistor, e.g., a gate region thereof, will change accordingly. In such an instance, the solution, when added to the chamber forms, or otherwise serves as, a gate electrode.

Hence, in specific embodiments, the gate voltage Vg of the I-Vg curve may be a solution gate voltage such as applied to the chemically sensitive field effect transistor through a solution flowed over a portion, e.g., a chamber, of the device. In some embodiments, the reference I-Vg curve and/or a chemical reaction I-Vg curve may be generated in response to the biological material and/or chemical reaction that is to be detected and/or occurs over or near the chemically-sensitive field effect transistor, such as within a chamber or well of the FET structure. In various embodiments, the processor may be configured to determine differences in relationships between a generated reference I-Vg curve and/or chemical reaction I-Vg curve. In certain instances, the circuitry component may include at least one analog-to-digital converter that is configured for converting analog signals, such as obtained as a result of the performance of the reaction(s) within the reaction well, or array of wells, into digital signals.

Accordingly, in another aspect, a chemically-sensitive field effect transistor device may be provided, wherein the device may include a structure having a conductive source and drain as well as having a surface or channel or other functionally equivalent surface structure extending from the conductive source to the conductive drain, such as where the surface or channel may include a one-, two-, or three-dimensional transistor material. The device may also include a processor such as where the processor is configured for generating a reference I-Vg curve and/or generating a chemical reaction I-Vg curve, in response to the chemical reaction occurring within a chamber of the chemically-sensitive field effect transistor, and may be configured to determine a difference between the reference I-Vg curve and the chemical reaction I-Vg curve.

In some instances, the difference between the reference I-Vg curve measurement and the chemical reaction I-Vg curve measurement is a shift in a minimum current point of the Vg value of the chemical reaction I-Vg curve relative to a minimum current point of the Vg value of the reference I-Vg curve. In other instances, the difference between the reference I-Vg curve and the chemical reaction I-Vg curve is a shift in an Ion value of the chemical reaction I-Vg curve relative to an Ion value of the reference I-Vg curve, for instance, where the Ion values are taken from a p-type or n-type section of the I-Vg curve. For example, the measurements of the slopes may be taken from the steepest and/or flattest sections on the p-type and/or n-type portions of the I-Vg curves. In particular instances, the difference between the reference I-Vg curve and the chemical reaction I-Vg curve is a shift in an Ioff value of the chemical reaction I-Vg curve relative to an Ioff value of the reference I-Vg curve. In one embodiment, the difference between the reference I-Vg curve and the chemical reaction I-Vg curve is a change in the slope of the chemical reaction I-Vg curve relative to a change in the slope of the reference I-V g curve. In another embodiment, the difference between the reference I-Vg curve and the chemical reaction I-Vg curve is an overall change in shape of the chemical reaction I-Vg curve relative to an overall change in shape of the reference I-Vg curve. In other embodiments, the difference in overall shape of the I-Vg curves is determined by first fitting a polynomial or other fitting line to each of the I-Vg curves and then comparing the coefficients of those fitting lines. In other embodiments, the difference between a reference I-Vg curve and the chemical reaction I-Vg curve is based on more than one chemical reaction I-V g curve.

Accordingly, in particular embodiments, the FET and/or processor may be configured to respond to a shift in the I-V or I-Vg curve, such as where the curve is shifted in response to the detection of a biological compound and/or the result of a reaction taking place in or on a surface of the FET device. In some instances, the I-V/I-Vg curve may be produced and/or shifted in response to a chemical reaction occurring on a reaction layer and/or the surface of a 1D or 2D, e.g., graphene, surface of the field effect transistor, such as resulting from the detection of a biological compound or reaction occurring within the well structure of the device. Hence, the FET and/or processor may be configured so as to shift the I-V curve or I-Vg curve such as in response to the chemical reaction. In various embodiments, one or more elements and/or methods, as herein described, may be used to shift a reference I-V or I-Vg curve and/or a chemical reaction I-Vg curve so that the difference between the reference I-Vg curve and a chemical reaction I-Vg is more pronounced. For instance, the device may include a structure, such as a membrane, other surface layer, and/or other element configured for enhancing the ability of the processor to determine the difference between various I-V and/or I-Vg curves.

Hence, in a further aspect, a chemically-sensitive FET transistor that is fabricated on a primary structure having a stacked configuration including an inorganic base layer, e.g., a silicon layer; a dielectric and/or an organic or inorganic insulator layer, such as a silicon dioxide layer; a 1D, 2D, or 3D material layer, such as a carbon nanotube, nanowire, or graphene layer; a reaction, e.g., oxidation, and/or passivation layer; and further having a conductive source and drain embedded in one or more of the layers, such as between and/or forming a gate structure, e.g., a solution gate region, may be provided. In various embodiments, the gate region may be configured so as to form a chamber or well and the 1D or 2D material and/or oxidation layers may be positioned between the conductive source and drain in such a manner as to form a bottom surface of the chamber. The structures may further include or otherwise be associated with an integrated circuit and/or a processor, such as for generating and/or processing generated data, such as sensor derived data.

Accordingly, in particular embodiments, a further structured layer, e.g., a secondary or tertiary structure, may also be provided, such as where the further structured layer may be included and/or present within the well or chamber, such as to enhance the ability of the processor to determine the difference between the current and/or voltages as well as their respective associated curves. More particularly, the additional structure may include an ion-selective permeable membrane, such as an ion-selective permeable membrane that allows ions of interest to pass through the membrane while blocking other ions, such as to enhance the ability of the processor to determine the difference between the reference I-V or I-Vg curve and the chemical reaction I-V or I-Vg curve, and thus enhance the ability of the processor to detect a desired chemical reaction. In various instances, the FET may be configured such that the I-V or I-Vg curve(s) may be shifted so as to better respond to, detect, and/or otherwise determine a biological compound and/or a chemical reaction, such as a biological compound and/or a chemical reaction occurring on the 1D or 2D, e.g., graphene, surface of the chemically-sensitive field effect transistor. In particular instances, the ion-selective permeable membrane may include a 2D transistor material, e.g., graphene, which may or may not be electrically connected to the source and/or drain layer and/or channel.

Accordingly, in various instances, the ion-selective permeable membrane may be positioned within the well and/or over a passivation layer, an ion sensitive or reaction layer, a 1D and/or a 2D transistor material layer, and/or a dielectric layer that itself may be positioned over and/or otherwise form a part of the chamber or channel. In certain embodiments, the membrane layer may be or otherwise be associated with an ion getter material, such as an ion getter material that traps ions that may or may not be relevant to the biological species and/or chemical reaction to be sensed and/or determined, such as to enhance the ability of the processor to determine the difference between the reference I-V or I-Vg curve and/or the chemical reaction I-V or I-Vg curve, e.g., because there are fewer interfering ions, thus enhancing the ability of the processor to detect the desired biological species and/or results of the chemical reactions. Particularly, the ion getter material may be arranged within proximity to the chamber and/or surface thereof so that the action of gettering the unwanted ions improves the detection capability of the chemically-sensitive field effect transistor. In some instances, one or more of the various layers herein, such as the ion getter material may be placed over one or more of the other layers, such as the dielectric layer, oxide layer, or 1D or 2D or 3D layers, positioned in proximity to one or more of the chambers, channels, or surfaces of the FET device.

In particular instances, an additional material, e.g., HMDS, may be included so as to manage the interaction of the chamber and/or channel and/or associated oxide layer and/or underlying 1D or 2D or 3D transistor layer. For instance, a chemically-sensitive field effect transistor of the disclosure may include a secondary or tertiary structure that includes a 2D transistor channel or surface which may include an ion-sensitive material over the channel or surface. In such an instance, the material may be sensitive to ions that are different from the ions associated with the biological molecule or chemical reaction that is to be detected. Particularly, in some instances, the action of sensing ions that are different from the ions associated with the biologics and/or chemical reactions that are to be detected allows the processor to filter out the signal from the unwanted ions from the signal of the ions of interest.

In a further aspect of the present disclosure, a system having a chemically-sensitive transistor, such as a field effect transistor (FET) including one or more chambers, e.g., a plurality of chambers having a well structure(s) formed therein is provided. In such an instance, the well(s) may be structured as a reaction location, wherein one or more chemical reactions may take place. In such an embodiment, the system may include a fluidics component having a fluid source, e.g., a reservoir, containing one or more fluids therein and configured for delivering the fluid from the reservoir to the reaction chamber, such as for the detection of a biologic and/or the performance of one or more chemical and/or biological reactions, such as a nucleic acid sequencing reaction. Hence, the fluidics component, e.g., the fluid source, may be in fluidic communication with the FET device configured for biological and/or chemical analysis.

Accordingly, in certain instances, the fluid may include one or more reactants, such as one or more analytes necessary for performing a sequencing reaction, as herein described. In a particular embodiment, the fluid may include one or more, e.g., a plurality of microbeads, having a nucleic acid template attached thereto, for instance, where the template is a DNA or RNA molecule to be sequenced, and the fluid containing the microbead is to be delivered to the well such as for carrying out the sequencing reaction. In such an embodiment, one or more of, e.g., each, of the plurality of microbeads may be configured so as to have electric charge and/or paramagnetic properties. The device may additionally include an electric and/or magnetic field component, e.g., having an electric and/or magnetic field generator, such as where the electric and/or magnetic field component is configured to generate an electric and/or magnetic field so as to interact with the electric and/or magnetic charge properties of each of the plurality of microbeads to attract the microbeads into a reaction location, such as a reaction surface, a channel, a well, a chamber, and/or a sensor of the FET device, such as by using electrophoresis and/or magnetism.

Hence, one or more, e.g., a plurality of microbeads, may be drawn onto or into a reaction location of the plurality of reaction locations, which locations may be formed as wells, e.g., one or more thin wells. The microbeads may include an analyte such as a biological material or a chemical material, e.g., one or more nucleotide sequences. Particularly, a fluid containing the analyte containing microbeads may be introduced into the wells, such as by a fluidics component of the disclosure. As the analyte may be a nucleic acid sequence having negative charge properties, an electric and/or magnetic field may be applied individually or collectively to the wells, so as to draw an analyte containing microbead onto each reaction location, e.g., into each well or sensor containing channel. In various instances, the electric and/or magnetic field component generates an electric and/or magnetic field so as to interact with the electric charge properties of the microbead thereby drawing it to the reaction location. In certain instances, the microbead itself may be charged and/or may have electric and/or magnetic properties, and thereby may be drawn to the reaction location using electrophoresis and/or magnetism.

The use of electrophoresis and/or magnetism allows for thinner reaction location structures. In particular instances, therefore, an electric and/or magnetic field generator may be configured for drawing and/or positioning a microbead within the well structure, such as in proximity to a channel or chamber of the device, and in other instances, the electric and/or magnetic field generator may be configured for reversing the electrical and/or magnetic field so as to repulse the microbead from the reaction location, channel, and/or chamber. In various instances, an array of reaction locations may be provided each having a magnet that allows for selective filling of the reaction locations with different numbers and/or types of microbeads, such as at select reaction locations. In such an instance, multiple electric and/or magnetic field generators for selective filling of reaction locations, e.g., wells.

Accordingly, one aspect of the present disclosure is a system and/or a method for positioning one or more, e.g., a plurality, of microbeads, e.g., containing one or more DNA and/or RNA templates attached thereto, within a reaction or plurality of reaction locations for biological or chemical analysis, such as for nucleic acid sequencing. The system may include a CMOS FET device having an integrated circuit structure configured for performing a biological or chemical analysis, such as within a plurality of nano- or micro-reaction wells, as described above, having a fluidic component, a circuitry component, and/or a computing component, and the method may include one or more of the following steps.

For instance, the method may include the fluidic component introducing a fluid to be in contact with the device, such as where the fluidics component is configured to control a flow a fluid of reagents over the array, and the fluid may include one or more microbeads that may have electric charge and/or paramagnetic properties. In such an instance, the device may include an integrated circuit structure, a plurality of reaction locations having one or more wells, a plurality of sensors and/or a plurality of channels, and/or an electric and/or magnetic field component. The electric field and/or magnetic field component may be configured to activate the electronic and/or magnetic field, and the method may also include activating an electric and/or magnetic field so as to interact with the electric and/or paramagnetic properties of each of the microbeads. The method may additionally include drawing the one or more microbeads into a reaction location of the plurality of reaction locations using electrophoresis and/or magnetism. In certain instances, the method may include positioning the one or more microbeads within the one or more reaction locations for biological or chemical analysis.

In particular instances, the electric and/or magnetic fields may be generated by the plurality of electric and/or magnetic field generators, e.g., included in the integrated circuit structure, in all or only a subset of the plurality of reaction locations so as to only attract a plurality of microbeads to the subset of reaction locations, such as for selectively filling the plurality of reaction locations with the plurality of microbeads. In such an instance, different types of microbeads may be attracted to different reaction locations, such as by pulsing the voltage and/or magnetic generators and/or keeping the same constant. Particularly, where an electric field generator is provided the voltage applied to the device may be variable or constant and may be less than about 10V, such as about less than 8V, or less than about 6V, including less than about 4V or about 2V or 1V. The voltage may be applied between a location above the fluid and a location on or below the reaction location, such as above the package lid and/or below the metal plate below the package. In certain instances, the location below the reaction location may be a metal or conductive layer such as within the package or package substrate. The method may also include the step of reversing the electric or magnetic field so as to eject the plurality of beads from the plurality of wells, sensors, and/or channels, either entirely or selectively.

Further, as indicated, each or a subset of the plurality of reaction locations may be utilized to generate electric fields to attract a microbead thereby allowing for programmability to each or a subset of reaction locations, for instance, 99% or 95% or 90% or 85%, or 80% or less of the plurality of wells are occupied with a microbead. Hence, the electric and/or magnetic field may be generated in only a subset of the plurality of wells, sensors or channels to only attract a plurality of microbeads to the subset. Likewise, a plurality of electric and/or magnetic field generators for selective filling the plurality of wells, sensors or channels with the plurality of microbeads, and/or ejecting the plurality of beads from the plurality of wells, sensors or channels. In such an instance, the electric and/or magnetic field generator may be an electric source, a permanent magnet and/or an electromagnet. As indicated, the plurality of magnetic field generators is configured to reverse the magnetic field to eject the plurality of microbeads from the plurality of reaction locations or a subset thereof.

Additionally, in one aspect of the present disclosure, a device, system, and/or method for verifying well occupancy for a plurality of wells for analysis of biological or chemical materials may be provided. For instance, a device of the system may include a plurality of wells having a plurality of sensors, such as where each well includes a graphene layer, and each sensor is configured as a field effect transistor. In such instances, the system may include a device for receiving a fluid containing the plurality of microbeads. Particularly, the device may include a processor, a CMOS structure having an integrated circuit, a plurality of wells, and a plurality of sensors within the CMOS structure. Each of plurality of wells may be configured to receive a microbead of the plurality of microbeads, and the CMOS structure may include a mechanism for drawing and/or ejecting the beads into or out of the wells. Hence, the method may include the step of flowing the plurality of microbeads over and/or into the plurality of reaction locations and/or wells and/or may include determining, e.g., through electrical and/or magnetic sensing if a reaction location and/or well is occupied or unoccupied and/or if a well contains one or multiple microbeads.

Consequently, the processor may be configured to determine if a well is unoccupied and/or if the well contains one or more, e.g., multiple microbeads. In certain instances, the processor may also be configured to eliminate or modify one or more of the measurements, such as based on the number of wells occupied or unoccupied, e.g., the number of wells containing none, one or multiple microbeads. For instance, the processor may be configured to eliminate from the measurement the number of wells unoccupied and the number of wells containing multiple microbeads, or compensate in the measurement for the number of wells unoccupied and the number of wells containing multiple microbeads, and the like.

In such instances, the measurement may be a shift in an I-V or I-Vg curve. In particular instances, the processor may be configured to eliminate from the measurement the number of wells unoccupied and the number of wells containing one or multiple microbeads and/or to compensate in the measurement for the number of wells unoccupied and the number of wells containing one or multiple microbeads. Accordingly, in some embodiments, the measurement may be a shift in an I-V or I-Vg curve, such as one or more of: generating a plurality of I-V or I-Vg curves so as to determine a shift in response to a chemical reaction occurring on or near the chemically-sensitive field effect transistor; generating a chemically-sensitive field-effect transistor I-V or I-Vg curve in response to a chemical reaction occurring on or near the chemically-sensitive field-effect transistor so as to detect a change in the slope of the I-V curve; and/or to sense shifts in a capacitance as a function of a gate voltage.

Having briefly described the present technology, the above and further objects, features and advantages thereof will be recognized by those skilled in the pertinent art from the following detailed description of the invention when taken in conjunction with the accompanying drawings.

BRIEF DESCRIPTION OF THE FIGURES

FIG. 1C is an illustration of molybdenum disulfide.

FIG. 3A is a block diagram of a system for analysis of biological or chemical materials.

FIG. 9B is an illustration of electrophoresis for biomolecule attachment.

Figure 1A:
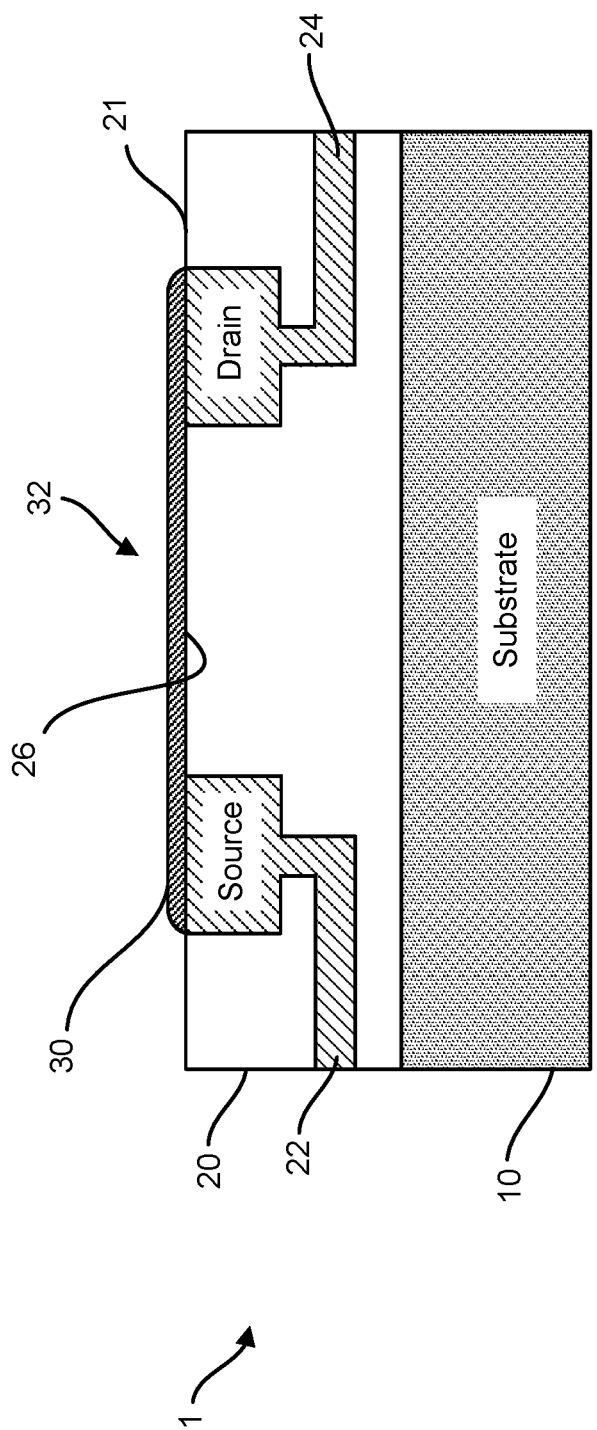
FIG. 1A is an illustration of a substrate for use in a chemically-sensitive field-effect transistor, such as for a system for analysis of biological and/or chemical materials. In this instance, the substrate includes an insulating layer having a source and a drain, and further includes a reaction zone having a graphene layer associated therewith.
Figure 1B:
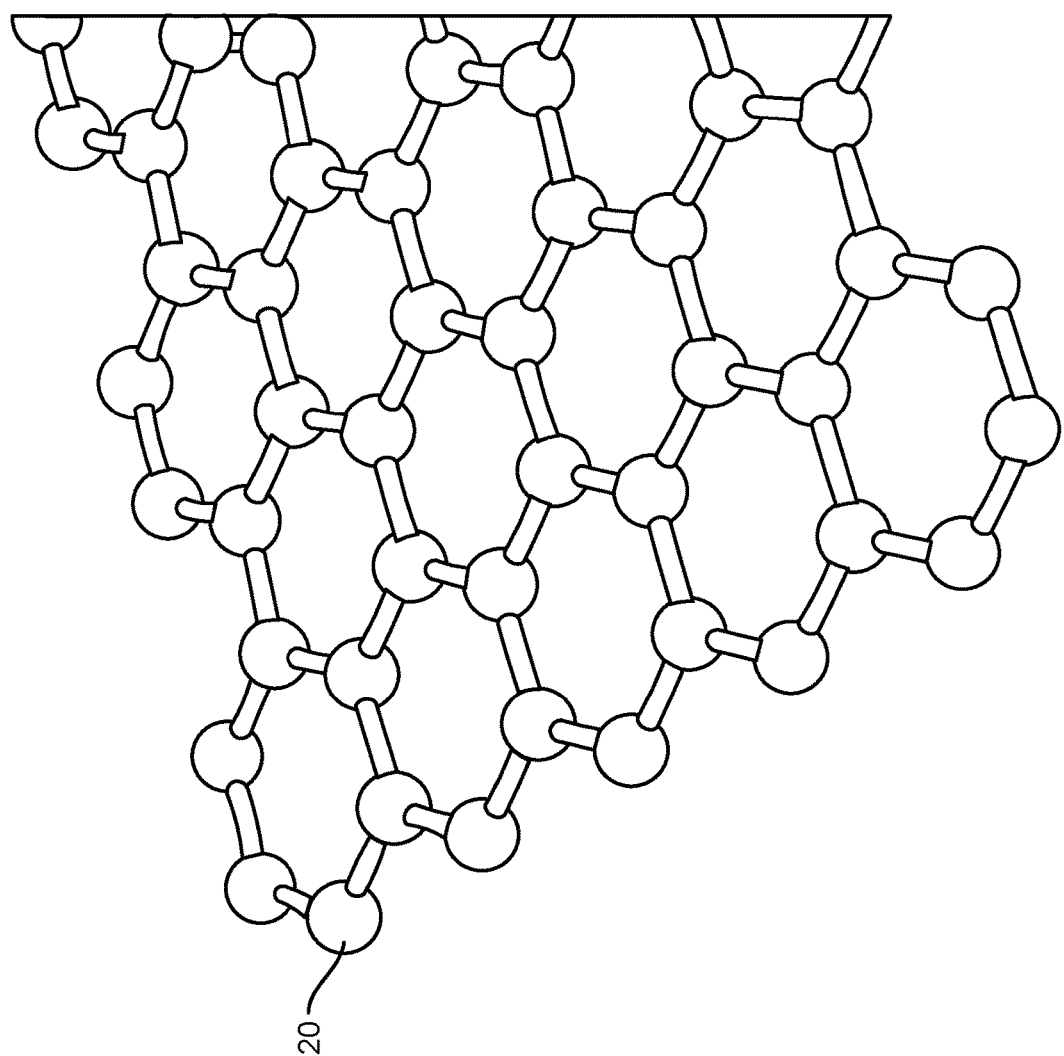
FIG. 1B is an illustration of a graphene layer, such as for use in the substrate of FIG. 1A.

Having briefly described the present technology, the above and further objects, features and advantages thereof will be recognized by those skilled in the pertinent art from the following detailed description of the invention when taken in conjunction with the accompanying drawings.

DETAILED DESCRIPTION OF THE DISCLOSURE

Accordingly, provided herein are devices, systems, and methods of employing the same for the performance of one or more chemical and/or bioinformatics analysis operations. Particularly, the devices, systems, and methods of the disclosure are directed in part to 1D, 2D, or 3D field effect transistor (FET) sensors, integrated circuits, and arrays employing the same for analyte measurements. The present FET sensors, arrays, and integrated circuits may be fabricated using conventional CMOS processing techniques based on improved 1D, 2D, or 3D FET sensor and array designs that increase measurement sensitivity and accuracy, and at the same time facilitate significantly small sensor sizes and dense sensor array designs.

More particularly, such improved fabrication techniques employing 1D, 2D, e.g., graphene, or 3D materials as a reaction layer provide for rapid data acquisition from small sensors to large and dense arrays of sensors. Such arrays may be employed to detect the presence and/or concentration changes of various analyte types in a wide variety of chemical and/or biological processes, including DNA hybridization, and/or nucleotide and/or protein sequencing reactions. Accordingly, in particular examples, graphene Field Effect Transistor (gFET) arrays facilitate genetic and/or protein sequencing techniques based on monitoring changes in various reactants within a zone associated with the array, such as changes in ion concentration, e.g., changes in hydrogen ion concentration (pH), or changes in other analyte concentrations, and/or binding events associated with chemical processes relating to sequencing synthesis, such as within a gated reaction chamber of the gFET based sensor. Particularly, the present disclosure is a chemically-sensitive graphene layered field-effect transistor for analysis of biological and/or chemical materials that solves many of the current problems associated with nucleic acid sequencing, genetic, and/or bioinformatics diagnostics.

Accordingly, provided herein is a system for analysis of biological and/or chemical materials. In various embodiments, the system includes a substrate, where the substrate includes one or more chamber and/or channel arrangements therein, such as where the chamber and/or a channel thereof may be associated with one or more sensors. In particular instances, a solution gated well structure is provided, such as where the well structure may be configured such that a biological and/or chemical reaction may take place within the well, such as proximate a channel structure therein. In various instances, the well is positioned on a portion of the substrate so as to align with an exterior surface of the channel of each sensor, such as where the well structure defines an opening allowing for direct fluid contact with the channel.

In various instances, the length of the interior surface, e.g., the channel, of the well, such as from the source to the drain may range from 0.05 micron to 3 microns, and a width of the surface and/or channel may range from 0.5 micron to 2 microns. In particular instances, the well structure may be configured to include or otherwise be associated with a nucleic acid template, such as a nucleic acid that may be directly or indirectly immobilized on a surface of the well. For instance, in certain instances, the nucleic acid template may be bound to an interior surface of the well chamber, such as on the substrate itself, or a layer associated therewith, e.g., a layer composed of a one- or two-dimensional transistor material. In various embodiments, the nucleic acid template may be bound to a secondary substrate, such as a bead positioned within the well, such as proximate the graphene layer.

In particular instances, the sensor substrate may be configured as a chemically-sensitive field-effect transistor. In such an instance, the transistor may include a conductive source and a conductive drain forming the channel structure, which channel structure extends from the conductive source to the conductive drain. In such an instance, the opening of the well is positioned in relation to the channel so that the opening aligns with the positioning of the source and drain, and more particularly with the associated sensor. As indicated, in various embodiments, a bounding surface of the well includes a one-dimensional (1D) transistor material, such as a carbon nanotube or a semiconductor nanowire, or a two-dimensional (2D) transistor material, such as composed of graphene, molybdenum disulfide, other metal dichalcogenides, and black phosphorous. In various instances, the 1D and/or 2D layer may further be associated with an insulator material. For instance, the insulator material for the well structure may be an organic material, such as a polyimide or BCB, and/or may be an inorganic material, such as silicon oxide or silicon nitride. Alternatively, the channel is composed of a silicene. Additional alternative materials for the channel include borophene, WS2, boron nitride, stanene (2D tin), germanane, nickel HITP, and Mxenes (Ti2C, (Ti0.5, Nb0.5), V2C, Nb2C, Ti3C2, Ti3CN, Nb4C3 and Ta4C3), and the like.

In particular instances, a reaction layer may be provided, such as a layer associated with the 1D or 2D, e.g., graphene, layer. For instance, in one embodiment, a thin (0.01 micron) passivation or etch stop layer may be placed over the graphene layer, such as in the case where a well etch process affects the graphene layer. In various instances, an oxide layer may be included, such as disposed within the chamber and/or channel thereof. In such instances, the oxide layer prevents the bead from contacting the 1D or 2D material or other reaction layer of the channel directly. The oxide layer may be composed of an aluminum oxide or a silicon oxide. In various instances, the oxide layer may have a thickness of 9 nanometers or less. The chemically-sensitive field-effect transistor can read through the oxide layer. In particular instances, the well structure may include a permeable membrane associated with the graphene layer.

In one aspect of the present disclosure is a chemically-sensitive transistor, such as a field effect transistor (FET) that is fabricated in a stacked configuration including a primary structure, such as a wafer, e.g., a silicon wafer, as well as one or more additional structures. For instance, an insulator material layer may also be included on top of the primary structure, and may be an inorganic material. The first and second structures may include a further structure containing one or more of a conductive source and/or a conductive drain, such as separated one from another by a space, and embedded in the primary and/or secondary structures and/or may be planar with a top surface of the secondary structure or a further layer or structure associated therewith. In various instances, the structures may further include a processor, such as for processing generated data, such as sensor-derived data. Accordingly, the structures may be configured as, or otherwise include, an integrated circuit, and/or may be an ASIC, a structured ASIC, or an FPGA.

For instance, as can be seen with respect to FIGS. 1A-1D, a graphene layered substrate 1 for a chemically-sensitive field-effect transistor, such as for a system for the analysis of chemical and/or biological materials is provided. The substrate 10 includes a primary base structure, such as composed of silicon. In various instances, the silicon based primary structure 10 may be configured as a complementary metal-oxide semiconductor (CMOS). The primary structure may include one or more additional structures such as an insulator material layer 20. For example, the substrate may be in a stacked configuration such as where a secondary structure 10, e.g., including an insulator material 20, is deposited or otherwise fabricated on top of the primary structure 10.

The structured primary 10 and/or insulator layers 20 may further include a reaction layer 26. For instance, the stacked structured layers may be configured to include a further structure, such as a channel structure, which in turn may be adapted as the reaction layer 26. Particularly, in certain instances, the insulator layer 20 may include a channel 26, such as containing one or more of a conductive source 22 and/or a conductive drain 22, such as separated one from another by a space 26, and embedded in the primary structure 10 and/or insulator material 20, and/or may be planar with a top surface 21 of the insulator layer 20. The source 22 and drain 24 may be composed of metal, such as damascene. In various instances, the insulator material for the channel structure 26 may be an organic or an inorganic material. In a particular instance, the organic material may be a polymer, polyimide, BCB or other like material. In another instance, the inorganic material may be a silicon oxide, e.g., a silicon dioxide, or a silicon nitride or other metal oxide or nitride.

In particular instances, the structures may be configured as a complementary metal-oxide semiconductor (CMOS) 1, which in turn may be configured as a chemically-sensitive FET containing one or more of a conductive metal source 22, a conductive metal drain 24, a channel or other reaction zone 26, and/or a processor. For instance, the FET 1 may include a CMOS structure having an integrated circuit that is fabricated on a silicon wafer 10, which further includes a silicon dioxide insulator layer 20, including a conductive damascene copper source 22 and a conductive damascene copper drain 24, which may be embedded in at least the insulator layer 20. In various instances, the structures may include a surface 21, e.g., a top surface, which surface may include the channel 26, such as where the surface and/or channel may be configured as a reaction zone 26 that extends from the conductive source 22 to the conductive drain 24. An exemplary length of the surface and/or channel 26 from the source to the drain may range from about 0.001 microns to about 10 microns, such as from about 0.01 microns to about 5 microns, for instance, from about 0.05 micron to 3 microns, including about 0.1 or about 0.5 microns to about 1 or about 1.5 or about 2 microns. An exemplary width of the surface and/or channel from side to side may range from about 0.001 microns to about 10 microns, such as from about 0.01 microns to about 5 microns, for instance, from about 0.05 microns to 3 microns, including about 0.1 or 0.5 microns to about 1 or about 1.5 or about 2 microns.

In certain instances, the surface and/or channel region may form a reaction layer 26 that may include a material layer 30, which material layer may be a one-dimensional (1D) transistor material, a two-dimensional (2D) transistor material, a three-dimensional (3D) transistor material, and/or the like. Accordingly, in various instances, a 1D transistor material may be included, which 1D material may be composed of a carbon nanotube or a semiconductor nanowire. In other instances, a 2D transistor material may be included, which 2D material may include a graphene layer, silicene, molybdenum disulfide, black phosphorous, and/or metal dichalcogenides. In various instances, a 3D material may also be provided.

For instance, in various embodiments, the material layer may be a single layer, 2D material, such as a graphene layer 30. Particularly, as can be seen with respect to FIG. 1B, graphene is a two-dimensional, monolayer of carbon atoms that are arranged as a lattice structure. This lattice structure forms regular hexagons with a carbon atom at each vertex. In such an instance, the bond length between adjacent carbon atoms may be about 1.42 Å and the lattice constant may be about 2.46 Å. This molecular structure is very unique in that each carbon atom shares one of its four free valence electrons with three of its adjacent and planar carbon atoms such that each of the three planar carbon atoms is orientated at about a 120° with respect to the other three carbon atoms. Such an orientation gives graphene it's honeycomb, lattice structure. Additionally, the fourth valence electron forms a pi bond, perpendicular to the three planar signma-bonded carbon atoms, which is responsible for the unique electronic characteristics of graphene.

Particularly, the single-layer, two-dimensional structure of graphene gives it at least three important characteristics with respect to its use herein: it creates the presence of a bandgap, it makes the graphene layer a seimimetal, and it promotes rapid charge transport (mobility and high-field transport) at room temperature. Hence, in various instances, a graphene FET, as herein described performs better as a biological sensor than a typical CMOS-FET device not having such a reaction layer. For instance, with respect to hybridization detection and/or sequencing, a traditional MOSFET transistor may have fundamental limitations in its sensitivity (due to channel thickness and intervening insulating layers), whereas the present gFET with its single atom thickness can be employed to form a solution gated reaction zone and/or channel, wherein the graphene layer may be in direct contact with the chemical reaction zone. Specifically, the reaction layers may include a 1D, 2D, and/or 3D structure 30 may be configured so as to have a much higher carrier mobility than the typical doped silicon commonly used in MOSFET or ISFET devices. This gives the herein disclosed 1D, 2D, and/or 3D FET sensor devices increased sensitivity to and faster detection of chemical reactions. Further, in various instances, the surface and/or channel 26 may include or make up a dielectric layer, such as for further increasing sensor sensitivity and/or functioning.

Figure 1D:
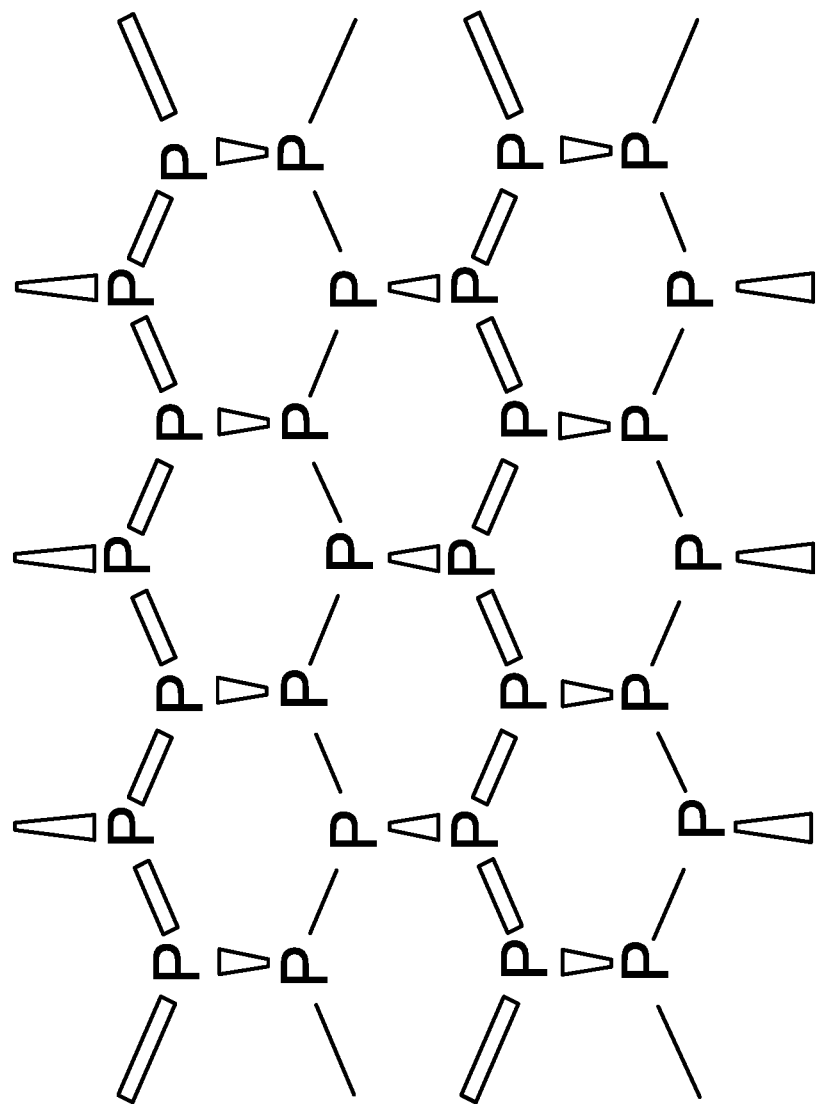
FIG. 1D is an illustration of black phosphorous.
Figure 1E:
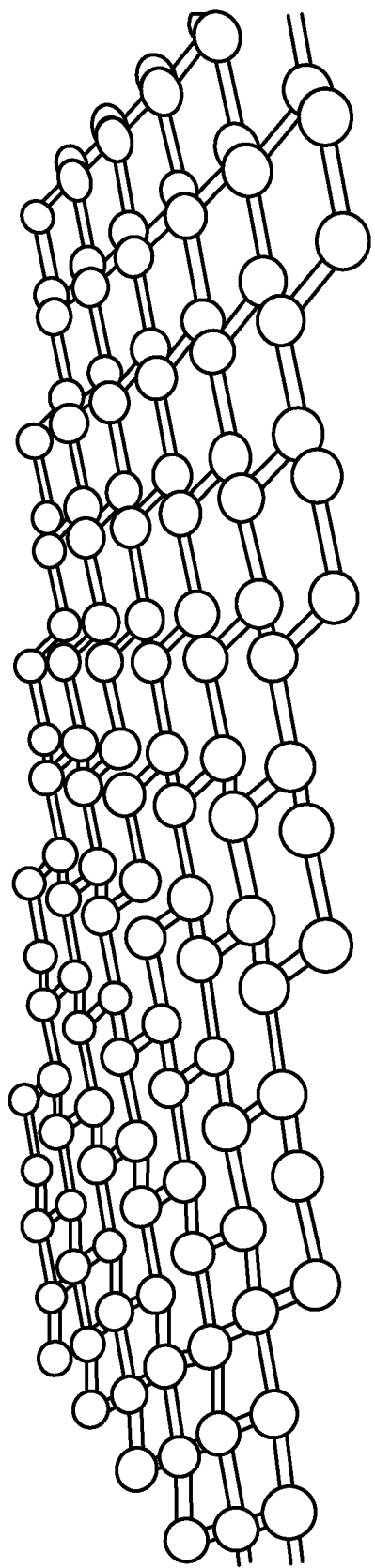
FIG. 1E is an illustration of silicone.
Figure 1F:
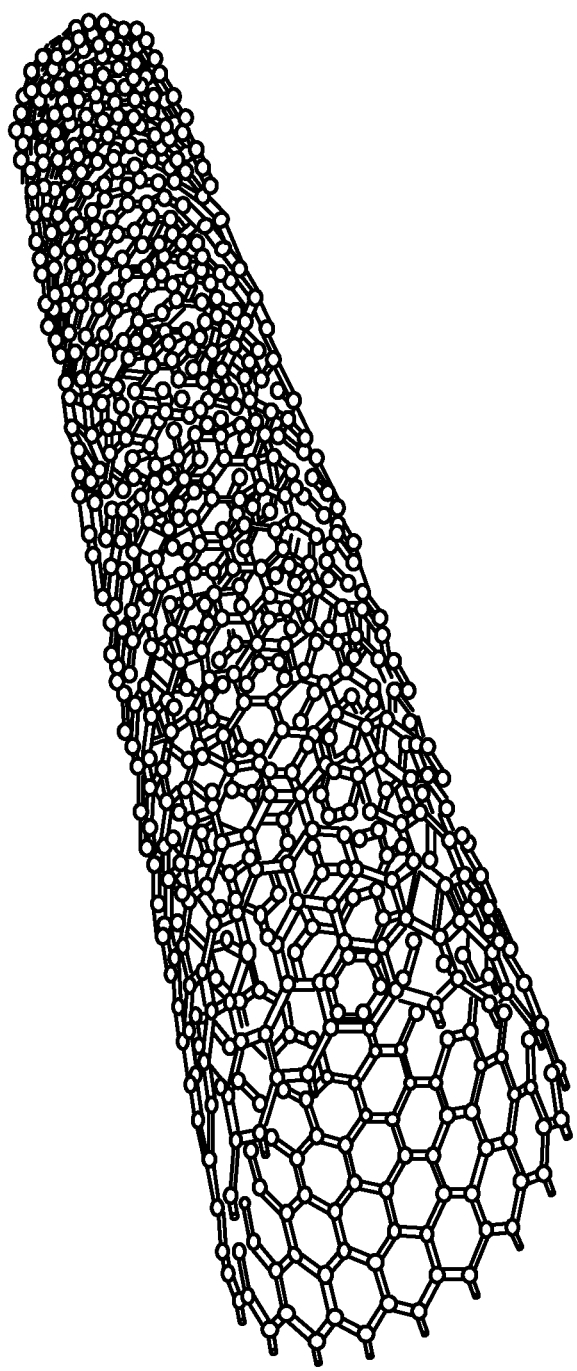
FIG. 1F is an illustration of a nanotube.
Figure 1G:
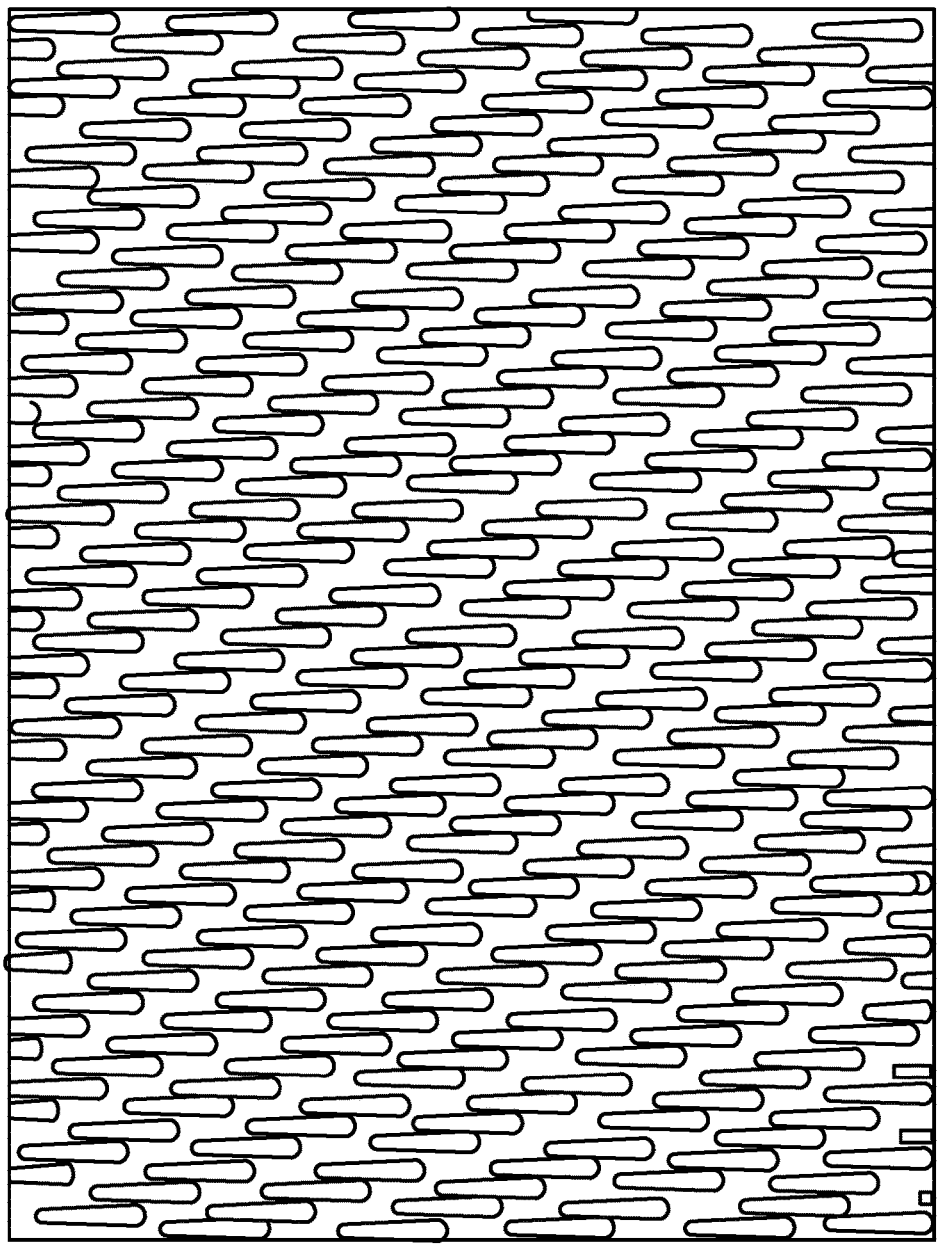
FIG. 1G is an illustration of a semiconductor nanowire structure.

Additionally, FIG. 1C depicts an alternative 2D material layer 30 that may be employed so as to increase sensitivity of the sensor so as to better enable the FET 1 to determine the presence and/or identity of one or more reactants and/or products thereof that results from the occurrence of a chemical and/or biological reaction that takes place proximate a reaction zone 26 of the FET device. As can be seen with respect to FIG. 1C, the 2D material layer in this instance is a molybdenum disulfide. Further 2D materials, as presented herein to increase sensitivity of the sensors include a black phosphorous layer, as depicted in FIG. 1D, and silicone as depicted in FIG. 1E. Alternatively, a 1D material, such as a carbon nanotube may be employed for these enhancement purposes, such as presented in FIG. 1F. A semiconductor nanowire structure, as depicted in FIG. 1G may also be used.

Figure 1H:
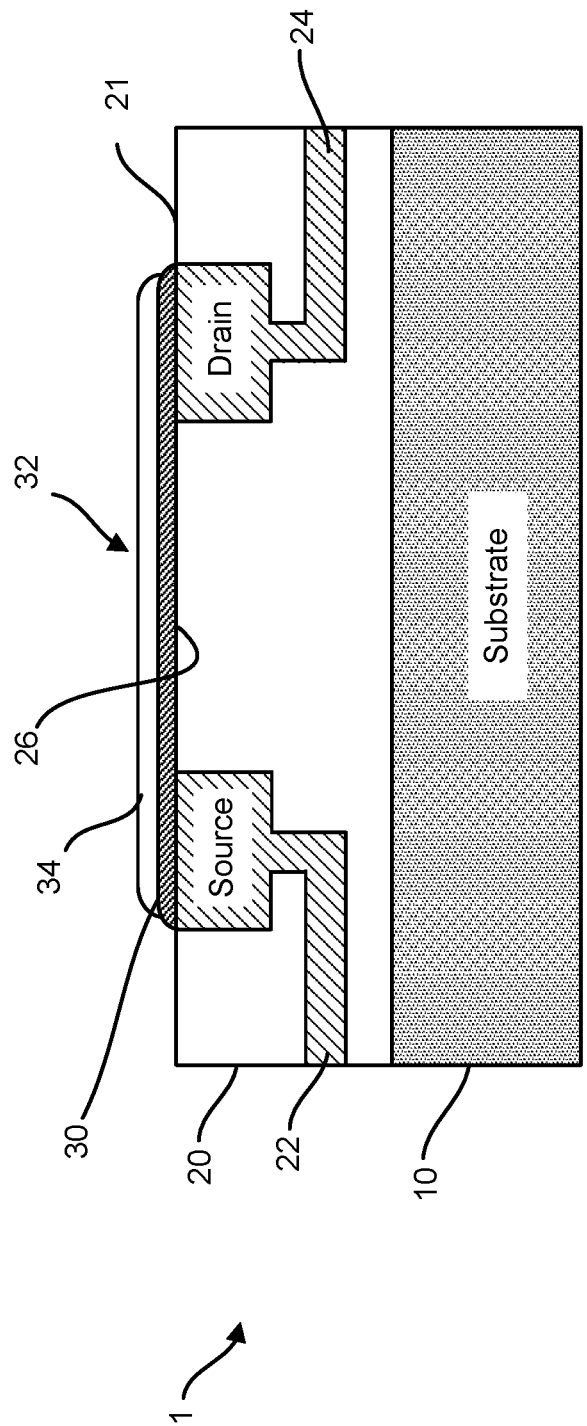
FIG. 1H is an illustration of a graphene layered substrate of FIG. 1A configured as a chemically-sensitive field-effect transistor having a reaction layer associated with the graphene layer, such as for use in a system for analysis of biological and/or chemical materials.

In various instances, as can be seen with respect to FIG. 1H, a reaction layer 34, e.g., an oxide layer, may be disposed on the surface and/or channel 26, such as layered or otherwise deposited on the 1D, 2D, e.g., graphene, or 3D layer 30. Such an oxide layer 34 may be an aluminum oxide or a silicon oxide, such as silicon dioxide. In some embodiments, the oxide layer may have a thickness of about 20 nanometers, such as about 15 nanometers, such as 10 or 9 or 7 or 5 nanometers or less. Particularly, the oxide layer 34, when present, may be composed of an aluminum oxide, a silicon oxide, a silicon dioxide, and the like.

In various instances, a passivation layer 36 may be disposed or otherwise be included on the surface and/or channel 26, such as layered or otherwise deposited on the 1D, 2D, e.g., graphene, or 3D layer 30 and/or on an associated reaction or oxidation layer 34 on the surface and/or channel 26. More particularly, the oxide and/or passivation layers may have a suitable thickness such as of from about 100 nm or about 75 nm to about 10 nm or 9 nm or less, such as about 0.5 microns or about 0.1 microns or about 50 nanometers or less to about 20 nanometers, such as about 15 nanometers, such as about 7 or about 5 nanometers or less, respectively.

Figure 1I:
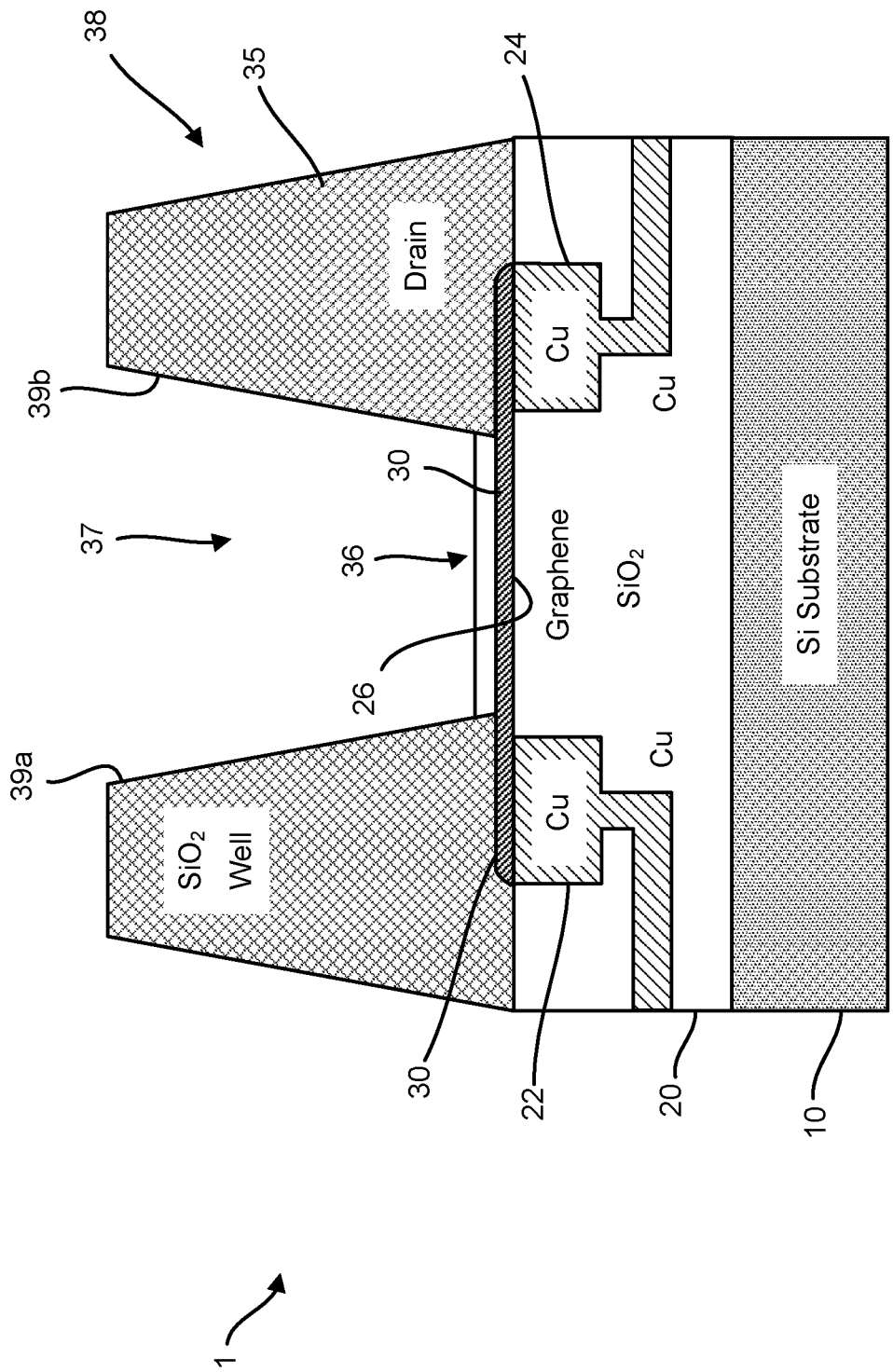
FIG. 1I is an illustration of a chemically-sensitive field-effect transistor of FIG. 1A having a silicon dioxide layer positioned over the substrate and insulating layers, and further having a well structure etched into the silicon dioxide layer so as to form a chamber proximate the graphene layered reaction zone. In this instance, the chamber includes a passivation layer or etch stop layer placed over the reaction layer.

As can be seen with respect to FIG. 1I, in particular instances, the primary 10 and/or secondary 20 structures may be fabricated to include or otherwise be associated with a tertiary structure 35, such as may be comprised of a silicon dioxide material. In various instances, the tertiary layer may be fabricated or otherwise configured so as to include a chamber or well assembly 38 in and/or on the surface 21. For instance, FIG. 1I depicts a field effect transistor in a stacked configuration and having a well structure 38, which well structure may be positioned on a portion of a surface, e.g., an exterior surface, e.g., 21, of a primary 10 and/or secondary structures 20. In some instances, the well structure 38 may have a plurality of walls or bounding members 39a and 39b set apart from each other by a distance that may be coincident with the space 26 so as to form the vertical boundaries of the chamber 38, e.g., with the space 26 forming the horizontal, bottom boundary. In particular instances, the horizontal surface of the space 26 may be configured as a reaction zone so as to form a reaction region within the well 38. Particularly, boundaries 39a and 39b may be formed on top of, or may otherwise include at least a portion of the 1D, 2D, e.g., graphene, and/or 3D material 30, and/or may additionally include the reaction 34, e.g., oxide, and/or passivation layers 36 (See FIG. 2B). In various instances, the chamber and/or well structure 38 may define an opening 37, such as an opening that allows access, e.g., fluidic access, to an interior of the chamber 38, such as allowing direct contact with the 1D, e.g., carbon nanotube or nanowire, 2D, e.g., graphene, or other 3D structure associated with the surface and/or channel 26.

Figure 2A:
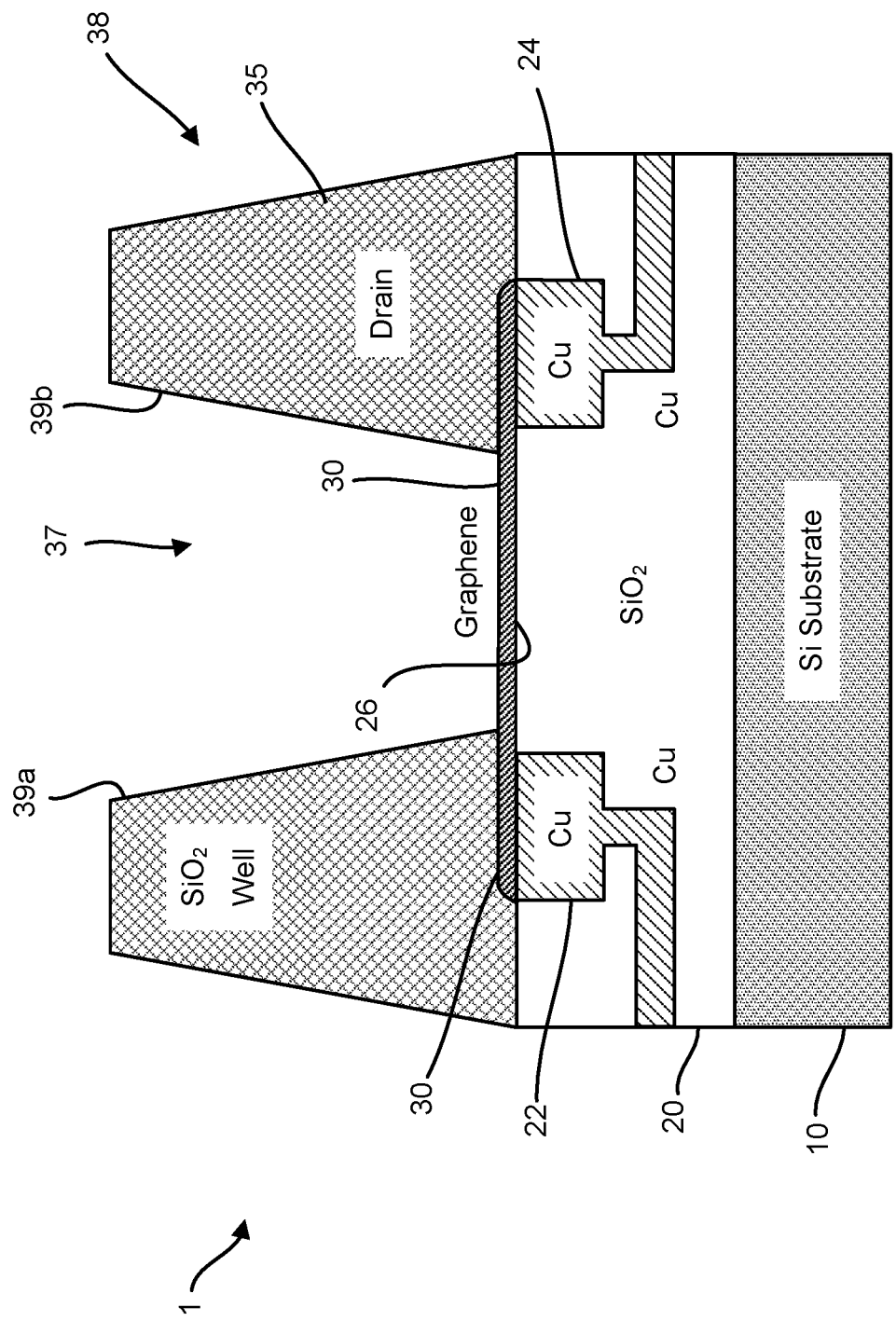
FIG. 2A is an illustration of a chemically-sensitive field-effect transistor having a graphene layered well structure, such as for a system for analysis of biological and/or chemical materials.

Accordingly, as presented with respect to FIG. 2A, a further aspect of the present disclosure is a bio-sensor 1. The bio-sensor includes a CMOS structure 10 that may include a metal containing source 22, e.g., a damascene copper source, as well as a metal containing drain 24, e.g., a damascene copper drain, such as embedded within an insulating and/or dielectric layer 20, e.g., positioned on top of the structure 10. The insulating layer may be an inorganic material, such as a silicon oxide, e.g., a silicon dioxide, or a silicon nitride, or an organic material, such as a polyimide, BCB, or other like material. The bio-sensor may also include a 1D or 2D or 3D layered, e.g., a graphene layered, surface or channel 26 extending horizontally from the source 22 to the drain 24, so as to at least be proximate therewith and thereby form a reaction zone 26.

In this instance, the surface structure 26 completely overlaps the source 22 and drain 24 regions. A further layer of material 35 may be positioned over the surface and/or channel region 26, which layer of material may further be etched or otherwise configured to include a well or chamber structure 38 having a bottom surface that may be positioned on or proximate a portion of an exterior surface of the 1D or 2D or 3D layer, such as to be coincident with the channel region 26. In such an instance, the well structure 38 may be a layered structure and may include a plurality of surfaces, such as first 39a and second 39b wall structures, such as extending from or otherwise being coincident with the surface of the reaction zone 26. For instance, the wall structures 29a and 29b may partially overlap the surface structure 26. Accordingly, FIG. 2A is an illustration of a chemically-sensitive field-effect transistor having a graphene layered well structure 38, such as for a system for analysis of biological and/or chemical materials.

Figure 2B:
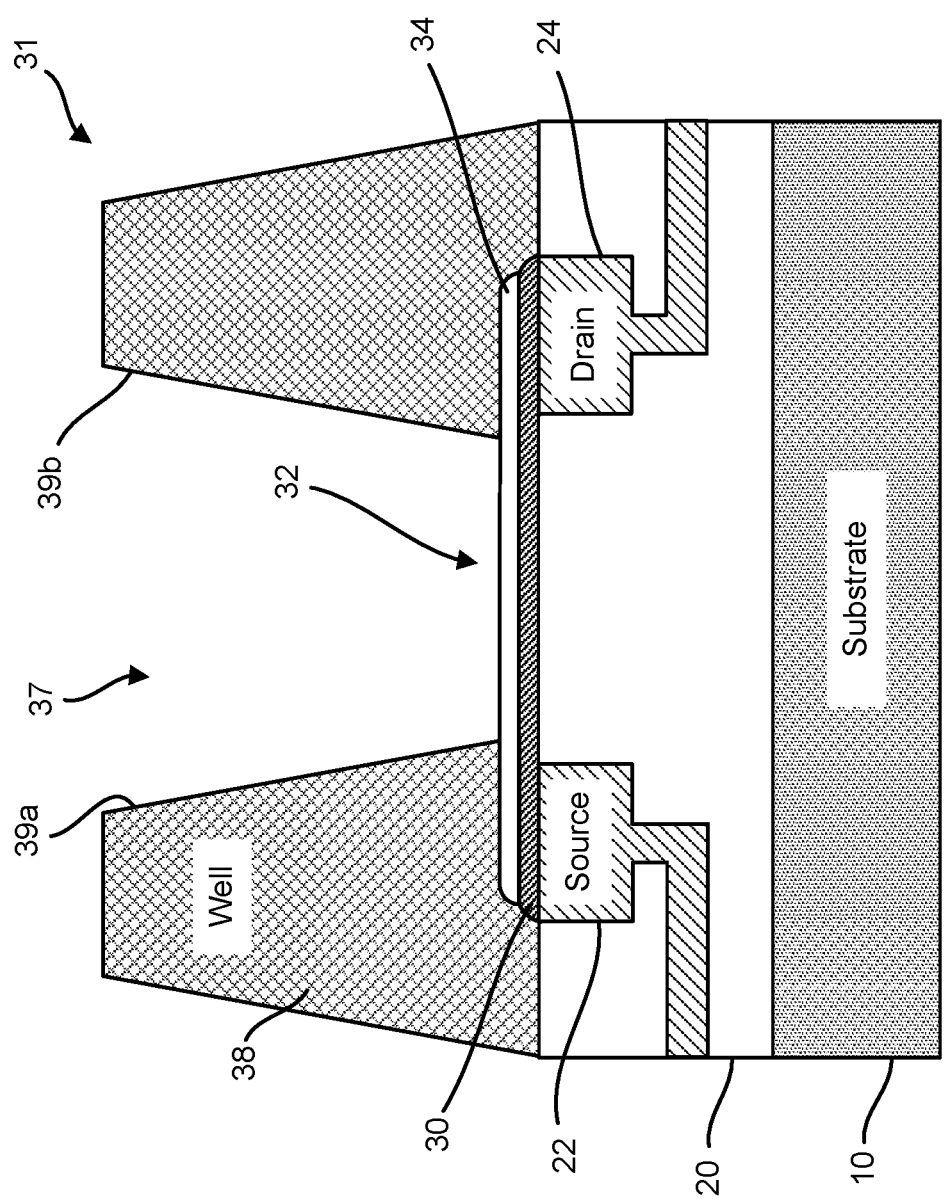
FIG. 2B is an illustration of a chemically-sensitive field-effect transistor of FIG. 2A, having a graphene layered well structure that further includes a reaction layer associated with the graphene layer, such as for a system for analysis of biological and/or chemical materials.

In particular instances, the well structure 38 may be configured so as to define an opening 37 that allows for direct contact with the surface 26, and thereby contact with the 1D, e.g., nanotube, nanowire, and/or 2D, graphene, layer. Hence, in various embodiments, the cavitated FET device may be configured so as to include a plurality of graphene wells or other chamber surfaces. In various instances, the FET device may be configured as a CMOS biosensor having a well structure 38 that further includes an oxide and/or passivation layer 34, as shown in FIG. 2B, which passivation layer 34 may be disposed in or on one or more of the chamber surfaces 39. The CMOS structure 10 may additionally include the componentry typical of a CMOS semiconductor and/or transistor such as used and/or manufactured as a microchip. Hence, in certain instances, as illustrated in FIG. 2B, the CMOS field effect transistor 1 may be configured as a chemically-sensitive transistor, and may be adapted to include one or more structures, such as nano- or micro-wells 38, that are formed as a reaction chamber, into which a solution, e.g., a solution containing one or more reactants, may be deposited, such as for the performance of one or more biochemical reactions, such as a nucleic acid hybridization and/or sequencing reaction. In particular instances, the chamber 38 may include a layered surface 26 having a 1D, 2D, or 3D material, and/or one or more reaction 34 and/or passivation layers 36 deposited therein. In such instances, the chamber of the CMOS device may be configured as a solution gate and therefore the FET may be adapted so as to be an ISFET, such as configured for receiving the reactants necessary for performing an analysis of biological and/or chemical materials, for instance, a hybridization and/or sequencing reaction.

Figure 2C:
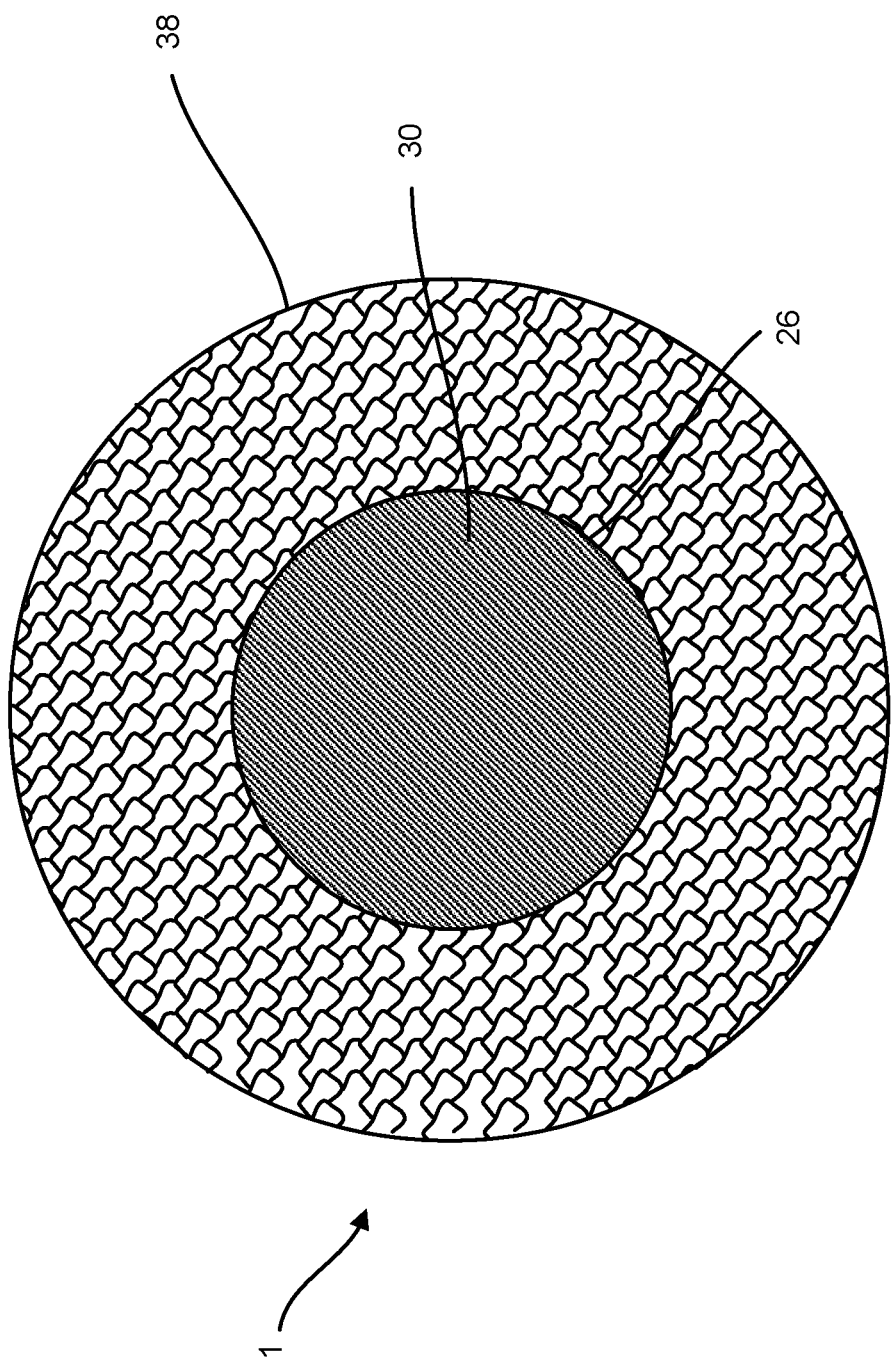
FIG. 2C is a top plan view of a chemically-sensitive field-effect transistor with a well structure.
Figure 2D:
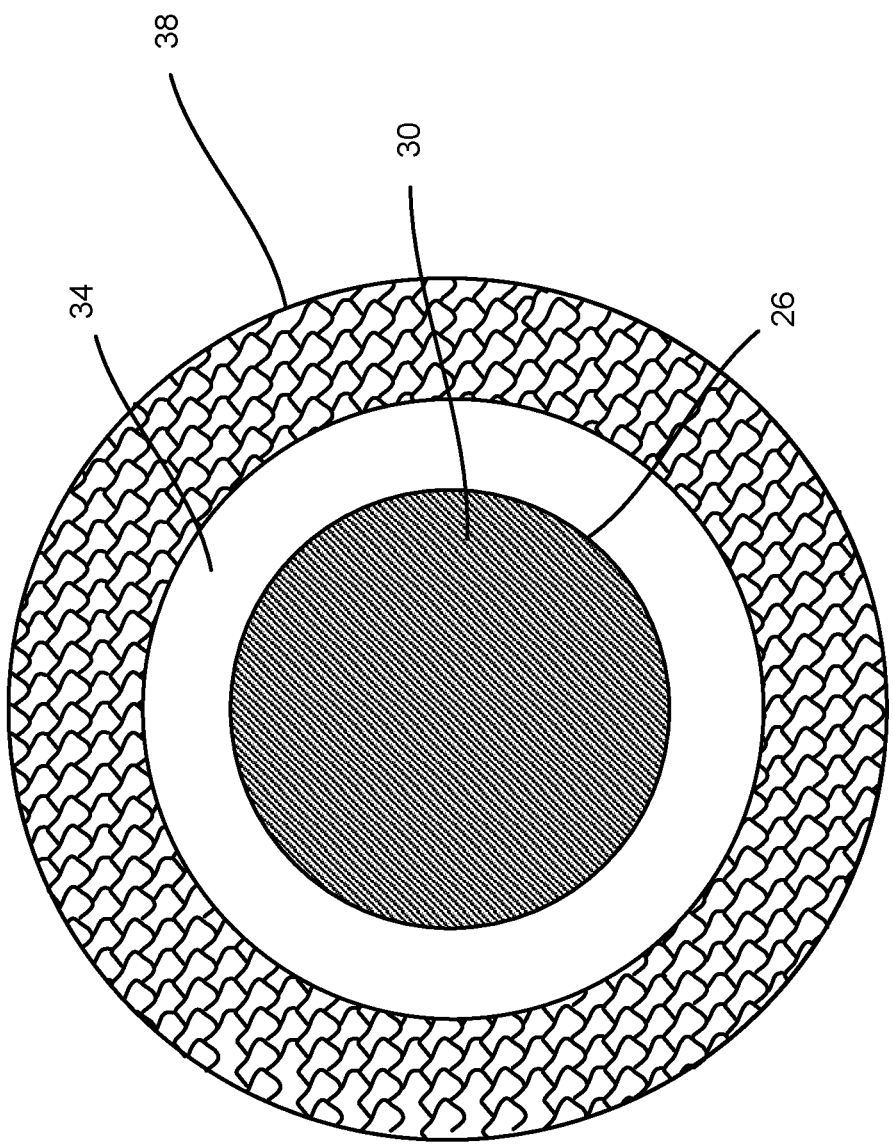
FIG. 2D is a top plan view of a chemically-sensitive field-effect transistor with another configuration of a well structure.
Figure 2E:
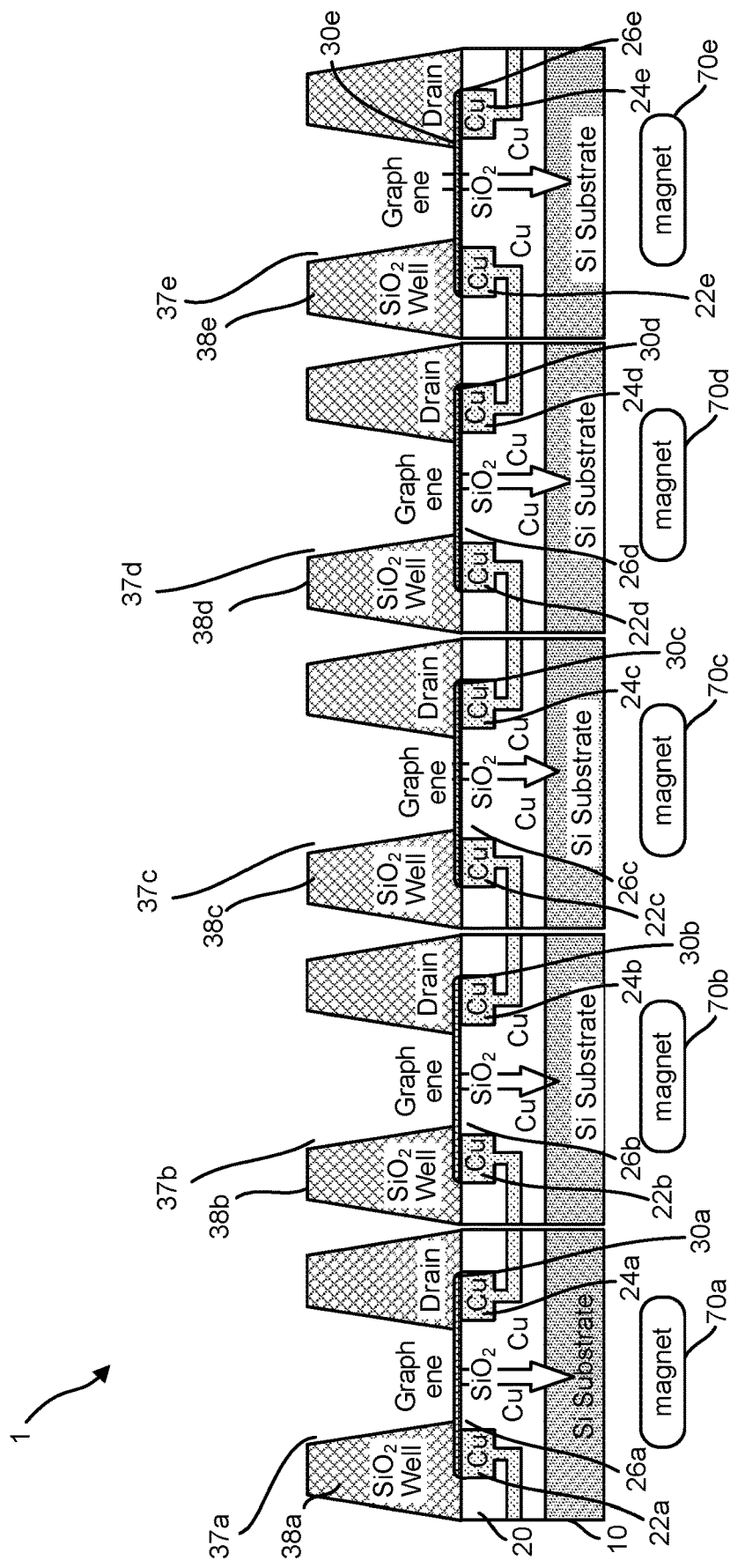
FIG. 2E is a top plan view of an array for a system for analysis of biological or chemical materials, where the array includes multiple chemically-sensitive field-effect transistors.

In some embodiments, as can be seen with respect to FIGS. 2E and 2F, the chemically-sensitive field effect transistor 1 may include a plurality of wells 38a-38e, having a plurality of openings 37a-e, where each well 38 is associated with one or more sensors, and may thus be configured as an array, e.g., a sensor array. Such an array or arrays may be employed to detect the presence and/or a change in concentration of various analyte types, such as within the wells 38, in a wide variety of chemical and/or biological processes, including DNA hybridization and/or sequencing reactions. For instance, the devices herein described and/or systems including the same may be employed in a method for the analysis of biological or chemical materials, such as for whole genome analysis, genome typing analysis, microarray analysis, panels analysis, exome analysis, micro-biome analysis, and/or clinical analysis, such as cancer analysis, NIPT analysis, and/or UCS analysis.

In a particular embodiment, a multiplicity of the wells 38 of the chemically-sensitive device may include a reaction zone 26 containing a graphene layer 30 so as to form a graphene FET (gFET) array 1. As herein described, the gFET array 1 may be employed to facilitate DNA sequencing techniques, such as based on monitoring changes in hydrogen ion concentration (pH), changes in other analyte concentrations, and/or binding events associated with chemical processes relating to DNA synthesis and/or hybridization reactions, such as within the gated reaction chamber or well 38 of the gFET based sensor 1. For example, the chemically-sensitive field effect transistor 1 may be configured as an array of CMOS biosensors and/or may be adapted to increase the measurement sensitivity and/or accuracy of the sensor(s) and/or associated array(s), such as by including one or more surfaces 26a-e or wells 38a-e having a surface layered with a 1D and/or 2D and/or 3D material 30, such as graphene, a dielectric or reaction layer 34, a passivation layer 36, and the like.

For instance, in a particular embodiment, illustrated in FIGS. 2E and 2F, a chemically-sensitive graphene field effect transistor (gFET) 1, such as a gFET having a CMOS structure is provided, where the gFET sensor, e.g., biosensor, may be configured as a microchip, having a plurality of wells 38 configured therein. In such an instance, the microchip 1 may include a silicon base layer 10 within which the circuit components of the transistor may be embedded. A dielectric layer 20, which may be a silicon dioxide layer, may be included, such as where the silicon dioxide layer is embedded with a plurality of conductive sources 22a-e and conductive drains 24a-e that are separated from one another so as to form a plurality of gate regions 26a-e. In particular instances, the gate regions are configured as a plurality of reaction zones 26a-e, where each reaction zone may be contained within a well structure 38. In such an instance, the microchip 1 may include a plurality of gate regions 26a-e that are configured as a plurality of solution gates 37a-e.

Particularly, in various embodiments, each sensor of the plurality of sensors includes a graphene field effect transistor. For instance, FIG. 2C depicts a top plane view of a first embodiment of a field effect transistor 1 having a channel structure 26 that is surrounded by a well structure 38, wherein a graphene layer 30 is deposited or otherwise positioned over the channel structure 26. FIG. 2D depicts a top plane view of another embodiment of the field effect transistor 1 having a channel structure 26 that is surrounded by a well structure 38, wherein an oxide layer 34 is deposited or otherwise positioned over the graphene layer 30, which in turn is positioned over the channel structure 26. Likewise, FIG. 2E depicts a top plan view of an array for a system for analysis of biological or chemical materials. In various instances, the array may include a plurality of sensors and one or more reference electrodes, such as a platinum or Ag/AGCl reference electrode. FIG. 2F depicts a portion of the wells of the array of FIG. 2E, in greater detail.

In various embodiments, one or more of the solution gates may include a graphene layered surface 30a-e, which in various instances may further include one or more oxide 34 and/or passivation 36 layers, such as layers that are disposed on the surface(s) of the bounding members of the wells or chambers 37 so as to increase the measurement sensitivity and/or accuracy of the sensors and/or associated array(s). Like above, in such instances, the solution gated chambers 37 of the arrays of the CMOS device may be configured as an ISFET, and be adapted for receiving the reactants necessary for performing various analyses of biological and/or chemical materials, for instance, one or more hybridization and/or sequencing reactions.

Accordingly, in one aspect, a system is provided, such as a system configured for running one or more reactions on biological and/or chemical materials so as to detect a presence and/or concentration change of various analyte types in a wide variety of chemical and/or biological processes. For instance, in some instances, the biological material may be a nucleic acid or other biological molecule, such as a protein, or the like. Hence, in particular instances, the system may be adapted for performing a DNA hybridization and/or sequencing reaction. In other instances, the analysis to be performed is for whole genome analysis, genome typing analysis, genomic panels, exome analysis, micro-biome analysis, and clinical analysis. In further analysis procedures, one or more clinical analysis may be performed such as a cancer analysis, NIPT analysis, and/or UCS analysis.

As such, the system may include an array 130 including one or more, e.g., a plurality of sensors, such as where each of the sensors includes or is otherwise associated with a chemically-sensitive field-effect transistor having a conductive source, a conductive drain, and a reaction surface or channel extending from the conductive source to the conductive drain. In particular instances, the array 130 may include one or more wells configured as one or more reaction chambers having the reaction surface or channel positioned therein. In some instances, the surface and/or channel of the chamber may include a one-dimensional (1D), or two-dimensional (2D), or three-dimensional (3D) transistor material, a dielectric or reaction layer, a passivation layer, and/or the like.

As can be seen with respect to FIG. 3A, the system may include a fluidics subsystem 100 for directing and controlling the flow of various fluids throughout the system 1. The fluidics system 100 may in turn include one or more of a fluidics component 120, such as for use in performing the reaction, e.g., delivering one or more analyte containing solutions to the array 130 for the performance of the reaction thereby, a circuitry component 140, such as for running the reaction and/or detection processes, and/or a computing component 150, such as for controlling and/or processing the same. For instance, a fluidics component 120 may be included where the fluidic component is configured to control one or more flows of analytes and/or reagents over the array 130 and/or one or more chambers thereof. Particularly, in various embodiments, the system 100 includes a plurality of reaction locations, such as surfaces $26_{a-n}$ and/or wells $35_{a-n}$, which in turn includes a plurality of sensors and/or a plurality of channels, and further includes one or more fluid sources 120, e.g., containing a fluid having a plurality of reagents and/or analytes therein, and fluid conduits, such as for delivery of the fluids from the source 120 to the one or more surfaces 26 and/or wells 35 of the array 130 for the performance of one or more reactions thereby. In certain instances, a mechanism for generating one or more electric and/or magnetic fields is also included.

Figure 3B:
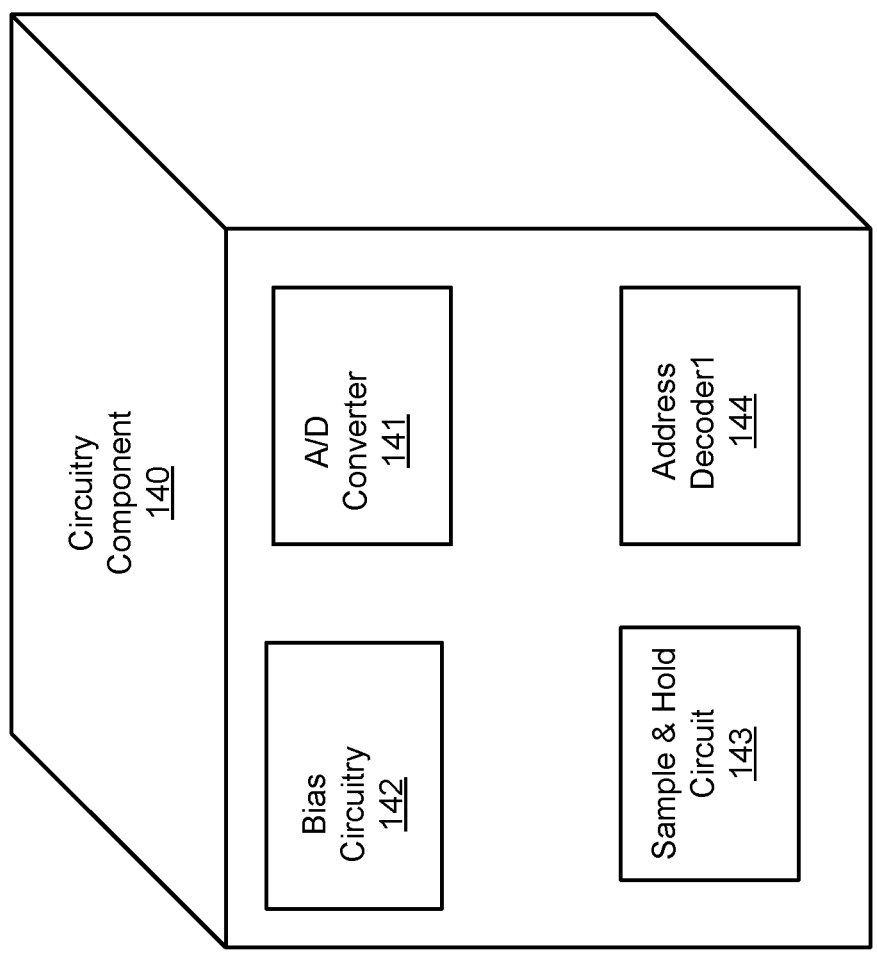
FIG. 3B is a block diagram of a circuitry component for a system for analysis of biological or chemical materials.
Figure 3C:
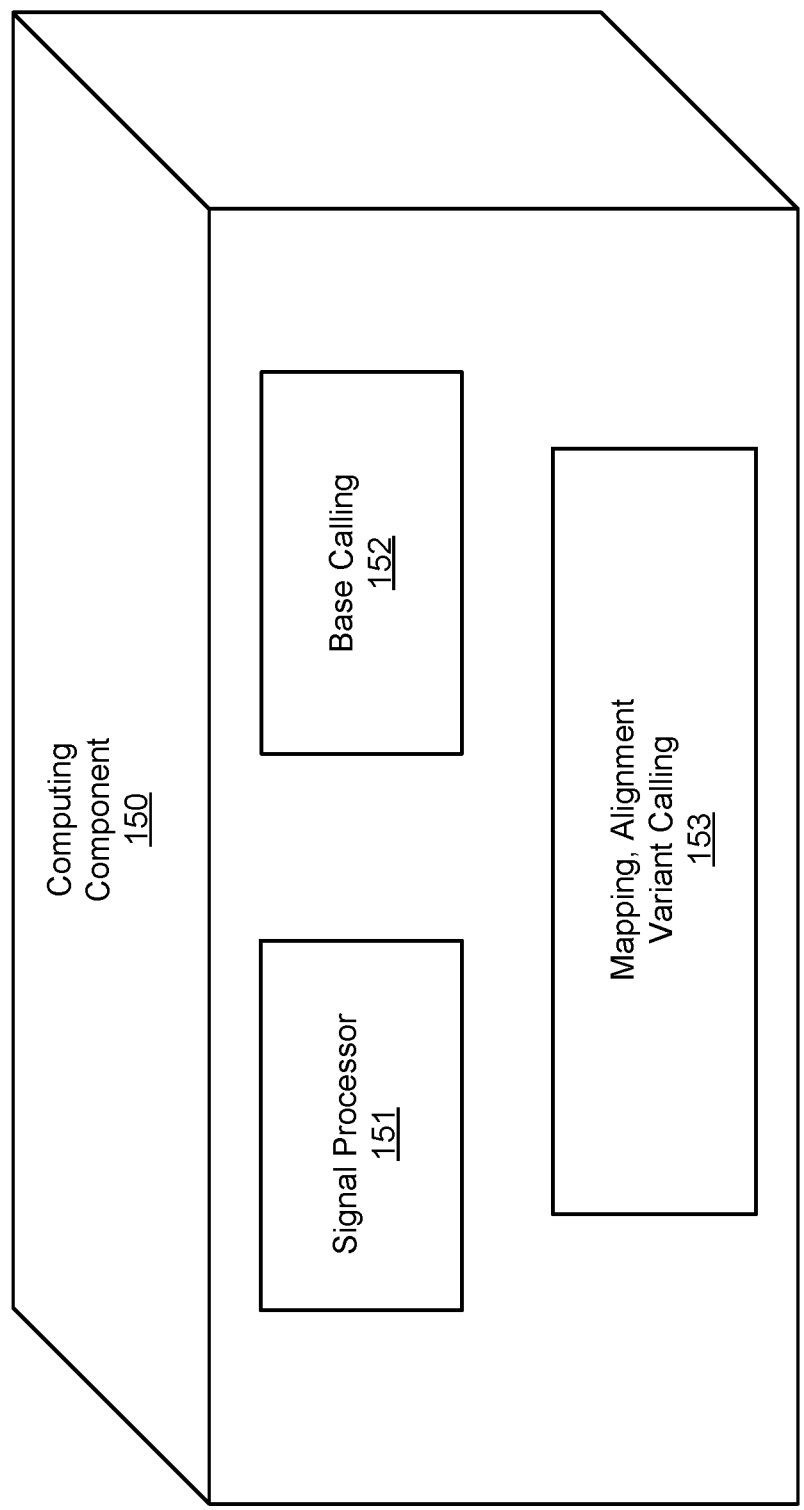
FIG. 3C is a block diagram of a computing component for a system for analysis of biological or chemical materials.

As can be seen with respect to FIG. 3B, the system 100 may additionally include a circuitry component 140, such as where the circuitry component may include an address decoder 144, a sample and/or hold circuit 143, a bias circuitry 142, and/or at least one analog-to-digital converter 141. For instance, the address decoder 144 may be configured to create a column and/or row address for each sensor of the array 130, such as by associating a unique identifier with each sensor, such as based upon its location within a given row and column within the array 130. It may also be configured for inputting or otherwise directing the various operations that rely upon the addressing of operations for a given well of the array. For instance, the address decoder 144 may target select signals to specific wells based on their column and/or row identifiers, so as to access a sensor and/or direct fluid flow to a given location, e.g., address within the array 130. The sample and hold circuit 143 may be configured to hold an analog value of a voltage to be applied to or on a selected well or column and/or row line of an array 130 of a device of the disclosure, such as during a read interval. Likewise, the bias circuitry 142 may be coupled to one or more surfaces and/or chambers of the array 130 and may include a biasing component such as may be adapted to apply a read and/or bias voltage to selected chemically-sensitive field-effect transistors of the array 130, e.g., such as to a gate terminal of the transistor. The analog to digital converter 141 may be configured to convert an analog value to a digital value 142, for instance, as a result and/or output of the reaction within an identified well 35 or selection of wells, e.g., a line of columns and rows.

A computing component 150 may also be included, such as where the computing component 150 may include one or more processors, such as a signal processor 151, a base calling module 52, and an analytics module 153. The signal processor 151 may be configured for determining one or more bases of one or more reads of a sequenced nucleic acid, such as results from a sequencing reaction. The base caller of the base calling module 152 may be configured to correct a plurality of signals, such as for phase and signal loss, to normalize to a key, and/or to a generate a plurality of corrected base calls for each flow in each sensor to produce a plurality of sequencing reads. The analytics module 153 may be configured for performing one or more analytics functions on the sequenced data, and may include one or more of a mapping module, configured for generating one or more seeds from the one or more reads of sequenced data and for performing a mapping function on the one or more seeds and/or reads; an alignment module, configured for performing an alignment function on the one or more mapped reads; a sorting module, configured for performing a sorting function on the one or more mapped and/or aligned reads; and/or an variant calling module, configured for performing a variant call function on the one or more mapped, aligned, and/or sorted reads. In various embodiments, the device and/or system may include at least one reference electrode.

Particularly, the system may be configured for performing a sequencing reaction. In such an instance, the device for performing the sequencing reaction may be adapted from a complementary metal-oxide semiconductor reformed to include one or more reaction chambers, e.g., micro or nano-wells, so as to form an array 130. The array 130 may be associated with one or more sensors having one or more chemically-sensitive field-effect transistors linked therewith. Such transistors may include a cascode transistor having one or more of a source terminal, a drain terminal, and or a gate terminal, such as forming a reaction zone. In such an instance, the source terminal of the transistor may be directly or indirectly connected to the drain terminal of the FET. In some instances, the gate terminal may be or may otherwise include a channel configuration, and may further include a one or two dimensional material associated with the gate. The 1D or 2D material may extend from the source terminal to the drain terminal, such as where the 1D channel material may be a carbon nanotube or nanowire, and the 2D channel material may be composed of graphene, silicene, a phosphorene, a molybdenum disulfide, and a metal dichalcogenide. The device may further be configured to include a plurality of arrays, such as arranged as one or more lines of columns and rows coupled to the sensors in the array of sensors. In such an instance, each column line in the plurality of column lines may be directly or indirectly connected to or otherwise be coupled with the drain terminals of the transistors, e.g., cascode transistors, of a corresponding plurality of sensors or pixels in the array, and likewise each row line in the plurality of row lines may be directly or indirectly connected to or otherwise coupled with the source terminals of the transistors, e.g., cascode transistors, of a corresponding plurality of sensors in the array.

In some instances, a plurality of source and drain terminals having a plurality of reaction surfaces, and/or associated channel members, extended there between may be included, such as where each channel member includes a one or two dimensional material. In such an instance, a plurality of first and/or second conductive lines may be coupled to the first and second source/drain terminals of the chemically-sensitive field-effect transistors in respective columns and rows in the array. Additionally, control circuitry 140 may be provided and coupled to the plurality of column and row lines such as for reading a selected sensor connected to a selected column line and/or a selected row line. The circuitry may also include a biasing component 142 such as may be configured for applying a read voltage to the selected row line, and/or to apply a bias voltage such as to the gate terminal of a transistor, such as FET and/or cascode transistor of the selected sensor. In a particular embodiment, the bias circuitry 142 may be coupled to one or more chambers of the array 130 and be configured to apply a read bias to selected chemically-sensitive field-effect transistors via the conductive column and/or row lines. Particularly, the bias circuitry 142 may be configured to apply a read voltage to the selected row line, and/or to apply a bias voltage to the gate terminal of the transistor, e.g., cascode transistor, such as during a read interval.

A sense circuitry may be included and coupled to the array so as to sense a charge coupled to one or more of the gate configurations of a selected chemically-sensitive field-effect transistor. Sense circuitry may also be configured to read the selected sensor based on a sampled voltage level on the selected row and/or column line. In such an instance, the sense circuitry may include one or more of a pre-charge circuit, such as to pre-charge the selected column line to a pre-charge voltage level prior to the read interval; and a sample circuit such as to sample a voltage level at the drain terminal of the selected transistor, e.g., cascode transistor, such as during the read interval. The sample circuit may also be included and contain a sample and hold circuit 143 configured to hold an analog value of a voltage on the selected column line during the read interval, and may further include an analog to digital converter 141 to convert the analog value to a digital value.

Figure 8A:
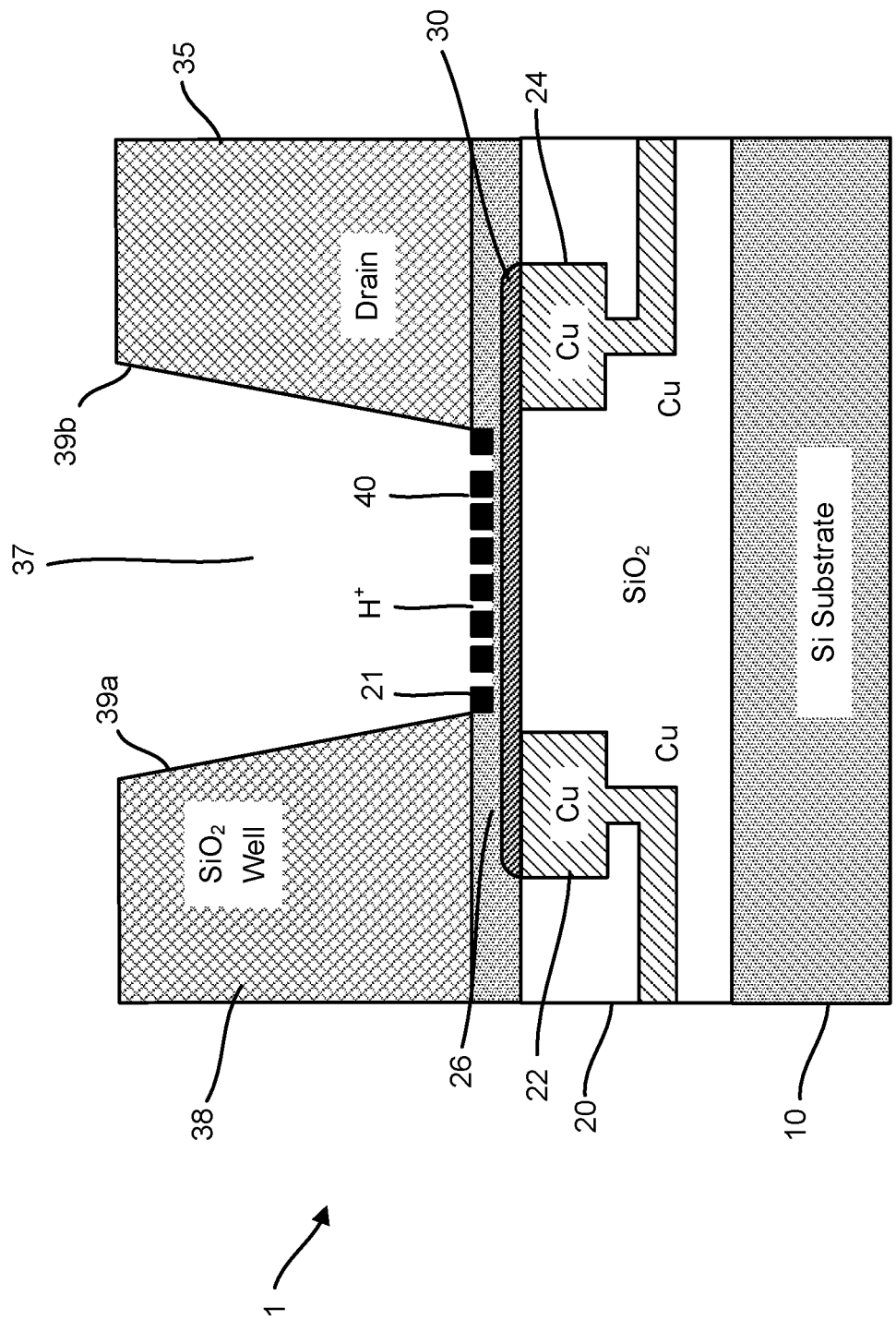
FIG. 8A is an illustration of a chemically-sensitive field-effect transistor with a graphene layered well structure and having a permeable membrane associated with the graphene layer.

In a further aspect, as seen with respect to FIG. 8A, a biologically and chemically-sensitive FET sensor 1 is provided wherein the sensor includes a stacked configuration having a plurality of layers and/or structures therein. For instance, a primary structure 10 includes an inorganic base layer, e.g., a silicon layer, which is fabricated to contain or may otherwise be configured as a CMOS FET. Accordingly, stacked on top of the base layer 10 may be a secondary structure 20 that may be configured as a dielectric layer and/or another inorganic or organic insulator layer, such as a silicon dioxide layer. The primary 10 and/or secondary 20 structures may additionally include or otherwise be configured to contain a conductive source 22 and drain 24 embedded in one or more of the structured layers, such as between and/or forming a gate structure 26. In particular embodiments, an additional structure or layer 35 may be positioned above the primary and secondary layers, which layer 35 may be etched to form one or more well structures 38, which well structure may be coincident with and/or proximate to the gate structure 26 so as to form a solution gate region therewith. In various embodiments, the solution gate region may include or otherwise be formed by the gate structured layer 26 as well as the bounding wall members 39a and 39b forming the well structure 38, such as by extending laterally upwards from the surface 21 and/or structured layer 26, and having opening 37 positioned therein so as to access the gate region 26.

The well structure 38 may further include one or more additional structures and/or layers, such as a 1D or 2D or 3D material 30 and/or an oxidation 34 and/or passivation 36 layers that may be positioned between the conductive source 22 and drain 24 and/or between wall members 39a and 39b in such a manner as to form a bottom surface and/or reaction zone 26 of the chamber 37. In various instances, one or more of the structures may further include or otherwise be associated with an integrated circuit and/or a processor, such as for generating and/or processing generated data, such as sensor derived data, e.g. indicative of a sequencing and/or hybridization reaction taking place within the well structure 38. In particular embodiments, a further structured layer 40, e.g., a secondary or tertiary or quarter structure, may also be provided, such as where the further structured layer may be included and/or present on a surface 26 or otherwise within the well or chamber 37, such as to enhance the ability of the sensor and/or the processor to determine the difference between a current and/or voltage applied across the source 22 and/or drain 24 of the transistor, as well as their respective associated charge curves, as described herein.

For instance, in the exemplary embodiment of FIG. 8A, a biologically and/or chemically-sensitive field-effect transistor 1 having a graphene layered 30 well structure 37 containing a further structured layer 40 configured for enhancing the sensitivity of an associated sensor. In this embodiment, the structured well layer 40 is configured as a permeable membrane that may be associated with the graphene 30 and/or reaction 34 layers. Particularly, the chemically-sensitive FET sensor 1 includes a surface 21, which surface may be within a well chamber 37, and be configured as a reaction region 26. The surface 21 of the reaction region 26 may be coupled to or otherwise include a 1D or 2D material such as a graphene layer 30 for detecting the presence of one or more chemical and/or biological events and/or elements resulting thereby. Accordingly, the surface 21 may be configured as a reaction region 26, and the well chamber 37 may be adapted such that a chemical and/or biological reaction may take place therein. The surface 26 and/or graphene structured layer 30 may be coupled with or otherwise include an additional structure, such as the permeable membrane 40, that is configured to enhance the ability of the graphene-based sensor 1 to detect the presence of a chemical and/or biological reaction. Particularly, the additional structure 40 may be an ion-selective permeable membrane that is positioned proximate to and/or over a reaction zone 26, which may be configured as a channel, and which membrane 40 may be adapted such that it only allows ions of interest to travel through the membrane 40, while excluding those ions that might cause interference with the sensing capabilities of the sensor 1.

For example, in particular instances, the membrane material 40 may be an organic or an inorganic material. A suitable membrane may be an inorganic material such as an oxide. An alternative material may be a separate layer, such as an additional 1D or 2D material, e.g., of graphene, which is not electrically connected to the FET or its component parts, e.g., the source 22 and drain 24. Another alternative material may be a polymer, such as Nafion, PEEK, a perfluorosulphonic, and/or a perfluorocarboxylic material. Alternatively, the material may be a HMDS or other siloxane, such as positioned under a graphene layer 30. Yet another alternative may be a getter material, such as containing a positive ion, e.g., NA$^+$, which may be positioned within the chamber 37, or may be positioned elsewhere on the sensor, such as a wall 39a and/or 39b thereof, and/or in a package that is adapted to attract unwanted ions. In another embodiment, the sensor enhancement material 40 may be an ion-selective functional layer(s) that is positioned over the sensor and adapted so as to detect contaminants, unwanted ions, or other impurities that may react with the reactants within the well 38 such that their interactions with the sensor 1 and thus the various determinations that the sensor 1 makes with respect to the reactions taking place therein, such as in relation to detecting the presence or absence of a desired ion, can be filtered out.

Accordingly, the chemically-sensitive field-effect transistors, as presented herein, for a system for analysis of biological and/or chemical materials, may be configured as solution gated field effect transistor devices having rows and columns of reaction chambers formed therein. In various instances, the field-effect transistors comprise a structure having or otherwise being associated with a channel and a processor. In such instances, the structure may include one or more of an insulating structure, a conductive source, a conductive drain, and/or a channel extending from the conductive source to the conductive drain, such as where the source and drain are embedded in the insulator and may be positioned therein so as to be planar with a top surface of the insulator. As indicated, in certain embodiments, the source and drain may each composed of a damascene copper material. Further, the channel may be composed of a one dimensional transistor material or a two-dimensional transistor material. And where desired, a reaction layer may be associated with the graphene layer, and in some instances, may include a passivation layer or etch stop layer that may be placed over the channel, such as between the two layers and/or above the graphene layer.

Figure 4A:
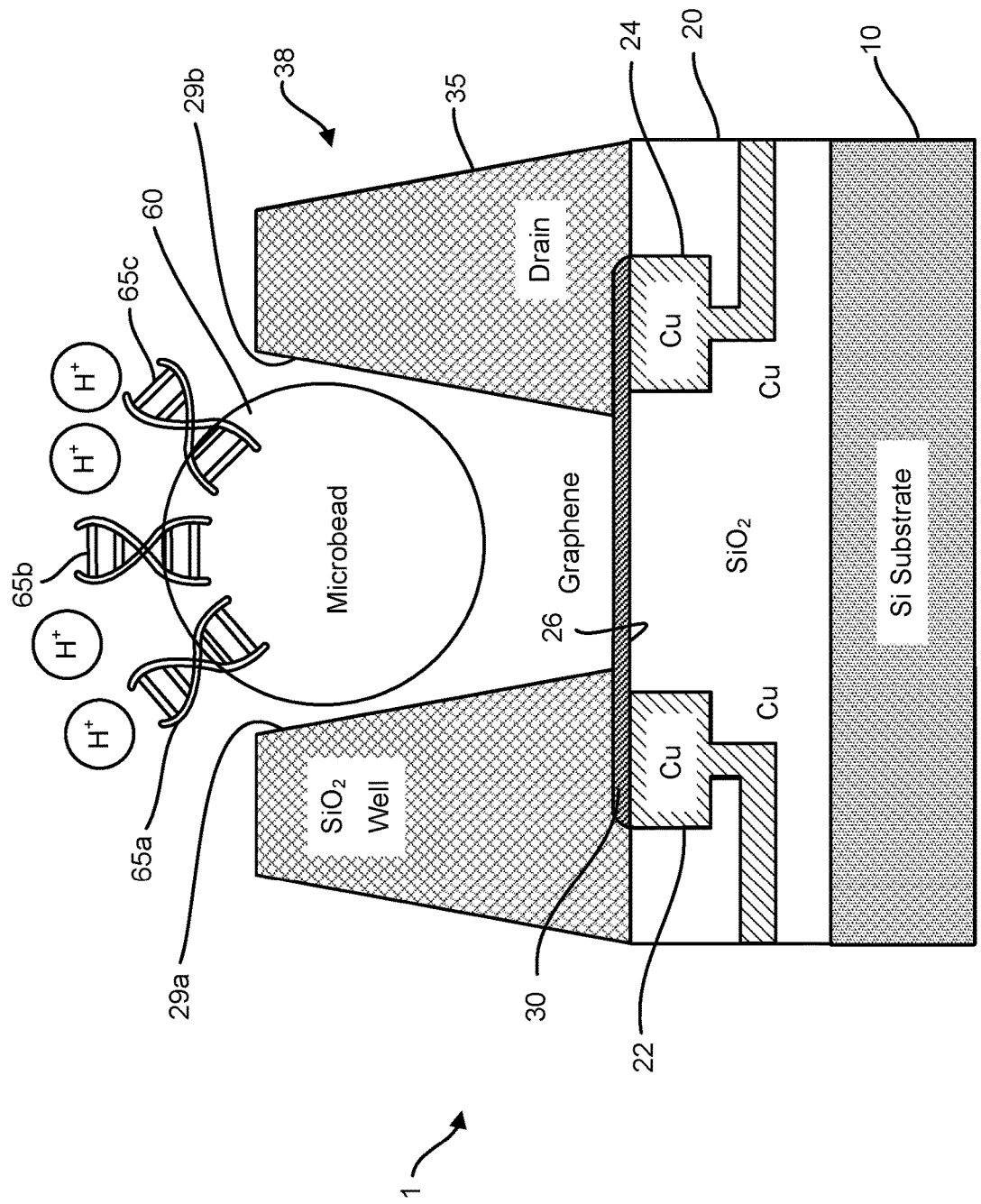
FIG. 4A is an illustration of a chemically-sensitive field-effect transistor of FIG. 2A, having a graphene layered well structure that includes a nano- or micro-bead therein.
Figure 4B:
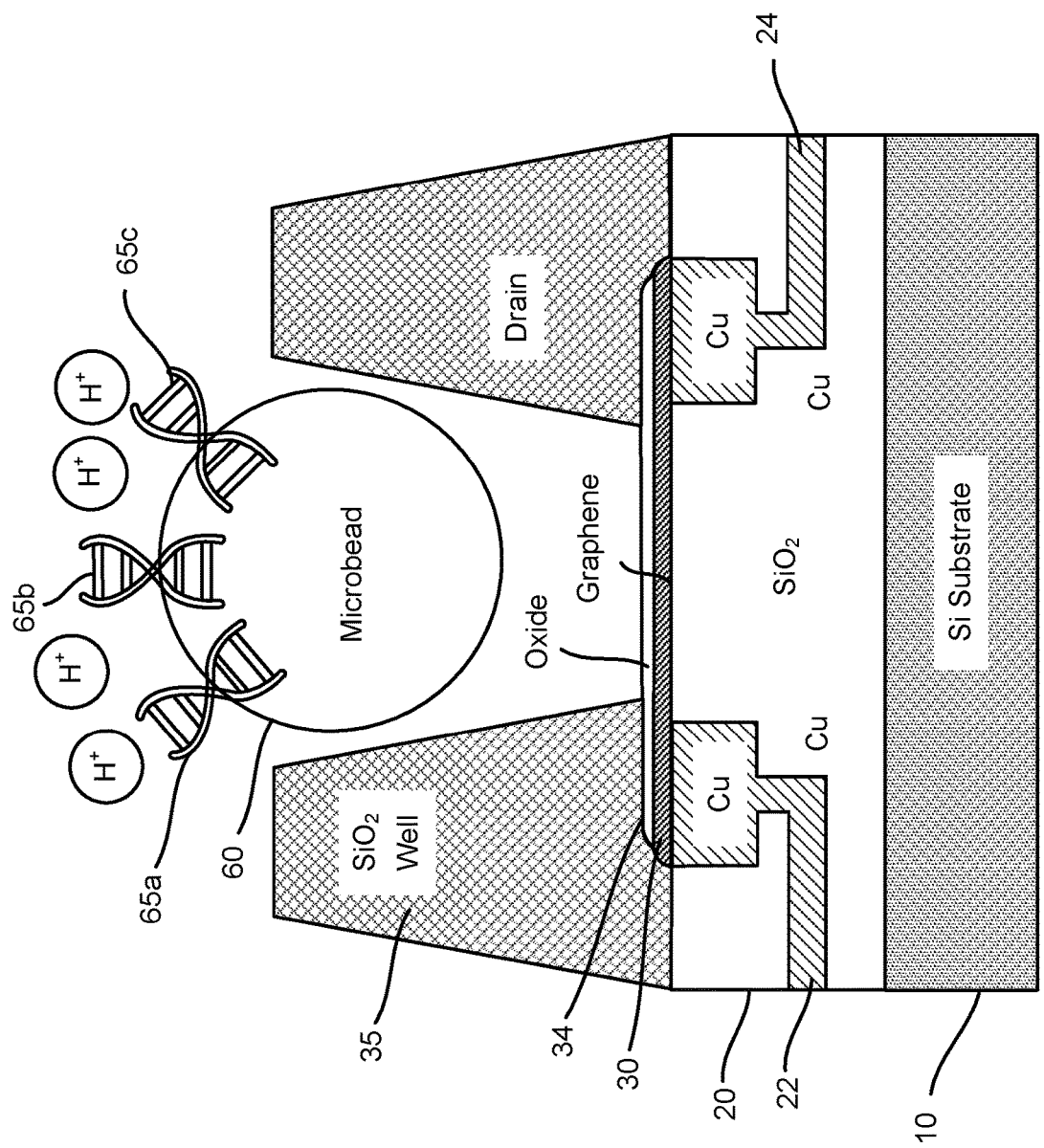
FIG. 4B is an illustration of a chemically-sensitive field-effect transistor of FIG. 4A, having a graphene layered well structure that includes a reaction layer associated with the graphene layer, which further includes a nano- or micro-bead therein.
Figure 4C:
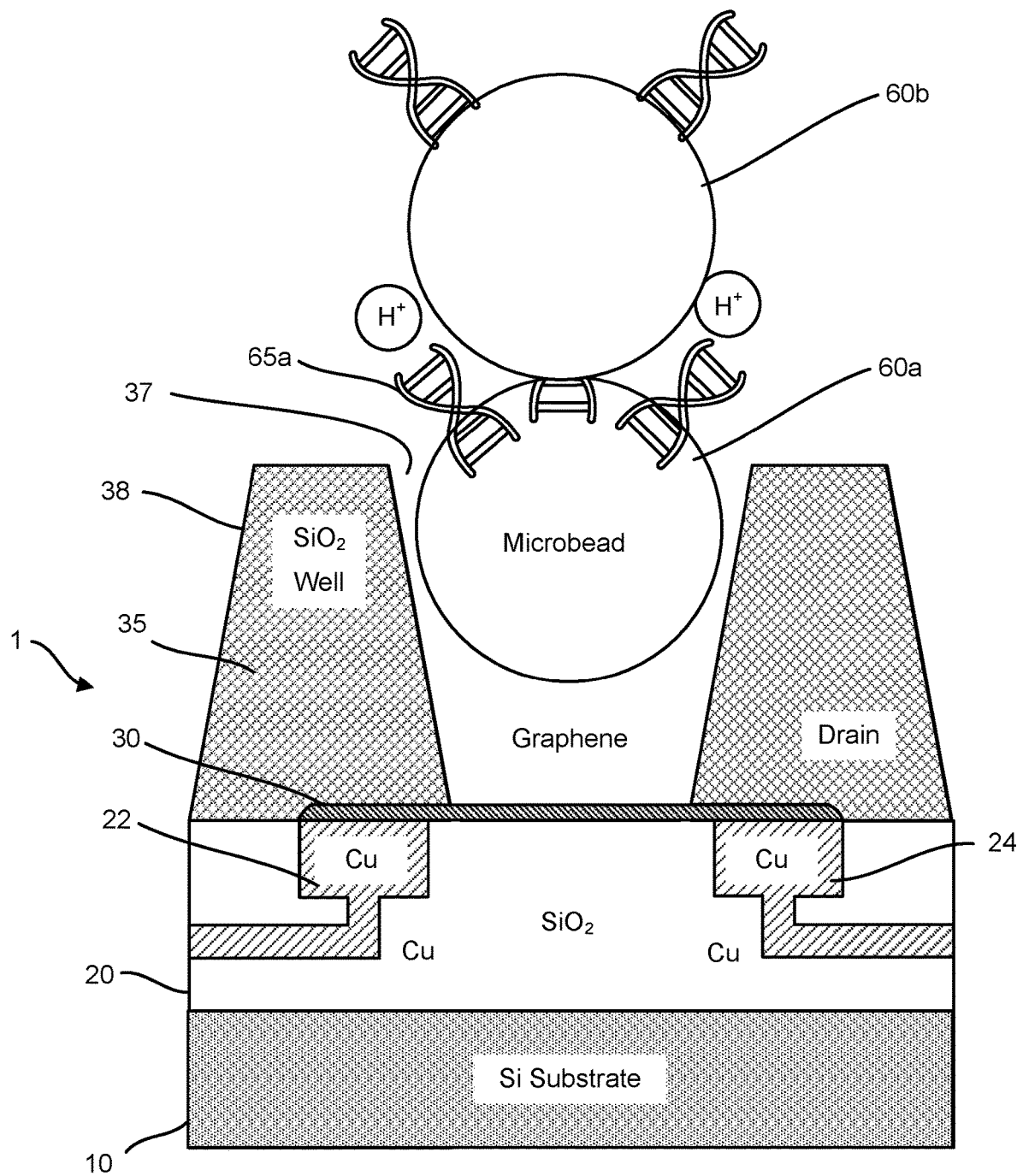
FIG. 4C is an illustration of a chemically-sensitive field-effect transistor of FIG. 4A, having a graphene layered well structure that includes a plurality of nano- or micro-beads therein.

As can be seen with respect to FIGS. 4A-4C, in various instances, a chemically-sensitive field-effect transistor 1 having a graphene layered micro- or nano-well structure 38 is provided. The FET 1 is configured as a microchip that includes a substrate layer 10 and an insulating layer 20 within which is embedded the various transistor components including a conductive source 22 and conductive drain 24 which may be adapted to form a gate region 26. In this instance, a graphene layer 30 may be positioned over the insulating layer 20 and positioned so as to contact at least a proximate portion of the source 22 and a proximate portion of the drain 24. In this instance, the substrate layer 10 is composed of silicon, the insulating layer 20 is composed of silicon dioxide, and the source 22 and drain 24 are composed of a conductive metal, such as copper.

The source 22 and the drain 24 are separated from one another and positioned relative to the graphene layer 30 so as to form a gate structure 26. In this embodiment, the gate structure 26 is further bounded by chamber walls 29a and 29b, which together form the well 28 into which a fluid may be delivered, such as for the performance of a bio-chemical reaction, and thus, forming a solution gate configuration. Particularly, an additional layer 35, which may also be composed of silicon dioxide, may be positioned above the first silicon dioxide layer 20, and be configured, e.g., via micro etching, to form a micro- or nano-well 38 so as to form a chamber 37, which chamber 37 may be adapted to receive a solution so as to form the solution gate region. The graphene layer 30 is disposed between the first 20 and second 35 silicon dioxide layers such as to form the bottom surface of the chamber 37. In this instance, the FET sensor is configured to detect a change in ion concentration, e.g., pH, which occurs within the well 38 such as when a solution containing reactants is added to the gate region within the chamber 37, and the reactants interact with an additional element contained within the chamber, such as a bound nucleic acid template.

Particularly, one or more solutions may be added to the chamber 37, such as in the performance of a bio-chemical reaction. For instance, a first solution including a nano- or micro-bead 60 may be added to the well 38. The nano- or micro-bead may be treated so as to be associated with one or more biopolymers, such as a DNA and/or RNA template 65. Once the nano- or micro-bead containing solution is added to the well 38, in such a manner that the bead 65 is retained therein, one or more additional solutions containing reactants, such as for the performance of a biological and/or chemical reaction, may then be added to the well 38. For example, where the biological and/or chemical reaction is a nucleotide synthesis reaction, the analyte containing solution to be added to the well 38 may include a nucleotide and/or polymerase composition that if the conditions are suitable within the chamber 37 will result in a binding event occurring between the template molecule 65 and the nucleotide reactant, thus resulting in the reaction taking place. Additionally, where the biological and/or chemical reaction is a hybridization reaction, the bound template molecule 65 may be configured as a probe, and the analyte containing solution to be added to the well 38 may include an additional DNA/RNA molecule of interest, which if the conditions within the chamber 37 are suitable will hybridize to the bound probe, thus resulting in the reaction taking place.

In either instance, the sensor 1 may be configured for detecting the occurrence of a reaction event taking place, such as by detecting a change in the ionic concentration within the solution within the chamber 37. Particularly, if the conditions are suitable for a reaction to take place, e.g., the appropriate reactants are present, a binding event will occur in such a manner that an ion, such as an H$^+$ ion, will be released into solution, such as within the chamber 37 and/or proximate the solution gate 26. In such an instance, the sensor 1 may be configured to sense the evolution of the ion, appreciate the change in pH, and detect that a reaction has taken place. In such a manner as this, a DNA/RNA molecule may be synthesized and/or a hybridization event determined.

Accordingly, as illustrated with respect to FIG. 4A, a chemically-sensitive field-effect transistor 1 is provided wherein the transistor 1 includes a graphene layered well structure 38 containing a nano- or micro-bead 60 therein, such as where the graphene layer 30 may be coincident with a channel region 26 so as to form a reaction zone therewith. Further, in various instances, such as illustrated in FIG. 4B, in addition to a graphene layer 30, the reaction zone 26 within the chamber 37 of the well 38 of the transistor 1 may further include a reaction layer 34, such as a reaction layer, e.g., an oxide layer, associated with the graphene layer 30. In addition to the reaction layer 34, the reaction zone 26 may additionally include a passivation or ESL layer 36. Furthermore, as can be seen with respect to FIG. 4C, in certain embodiments, the chemically-sensitive field-effect transistor 1 may include a plurality of nano- or micro-beads therein, such as within the chamber 37 of the well 38 of transistor 1, so as to allow a plurality of reactions to take place at the same time involving a plurality of substrates, 60a and 60b, within the well, which increases the surface area for reactions.

In some instances, it may be useful to provide a mechanism for assisting the targeting of the microbead(s) 60 to the reaction zone 26 of the FET 1. Particularly, as can be seen with respect to FIGS. 5A-E, a chemically-sensitive field-effect transistor 1 is provided. In this instance, the transistor 1 may be a multi-layered structure including a primary, e.g., a substrate layer 10, a secondary structure layer, e.g., an insulator layer 20, and may further include an additional layer 35, e.g. a silicon dioxide layer, which layer may be cavitated so as to include a divot 38, such as a divot on a surface 21 of the substrate, and sized to at least partially contain a nano- or micro-bead 60 therein. In certain instances, the surface of the divot 38 may be centered such that the bead 60 rests within the divot 38 so as to be proximate the reaction zone 26 and/or a channel structure associated therewith. In particular instances, the reaction zone 26 includes a graphene layer 30 positioned at least partially between the primary and tertiary layers, and in such instances, a silicon dioxide layer 34 may be positioned above the graphene layer within the reaction zone 26. In this instance, to draw and/or attach the bead(s) 60 to the reaction zone 26, an electromagnetic field may be employed. Hence, as shown in FIG. 5A, a microbead 60 is positioned on the transistor surface 21, within the reaction zone 26, and in proximity to a channel.

More particularly, the reaction zone 26 of the FET 1 may be configured to include a channel region that is formed to correspond to the region, e.g., point, of contact between the surface of the graphene layer 30 and the bead 60. Further, to facilitate this contact, the FET 1 may include an attracting mechanism 70 that is configured to attract or otherwise draw the bead 60 in to proximity of the reaction zone and/or channel 26. For instance, in particular instances, the nano- or micro-bead 60 may include a charged and/or metallic element, and the attracting mechanism 70 may be configured so as to generate an electric and/or magnetic field, such as for drawing the bead 60 to the reaction zone 26. For example, in some embodiments, the electric field generator 70 may be a pulse generator, and in other embodiments, such as illustrated in FIG. 5A, the magnetic field generator 70 may be a magnet.

Figure 5A:
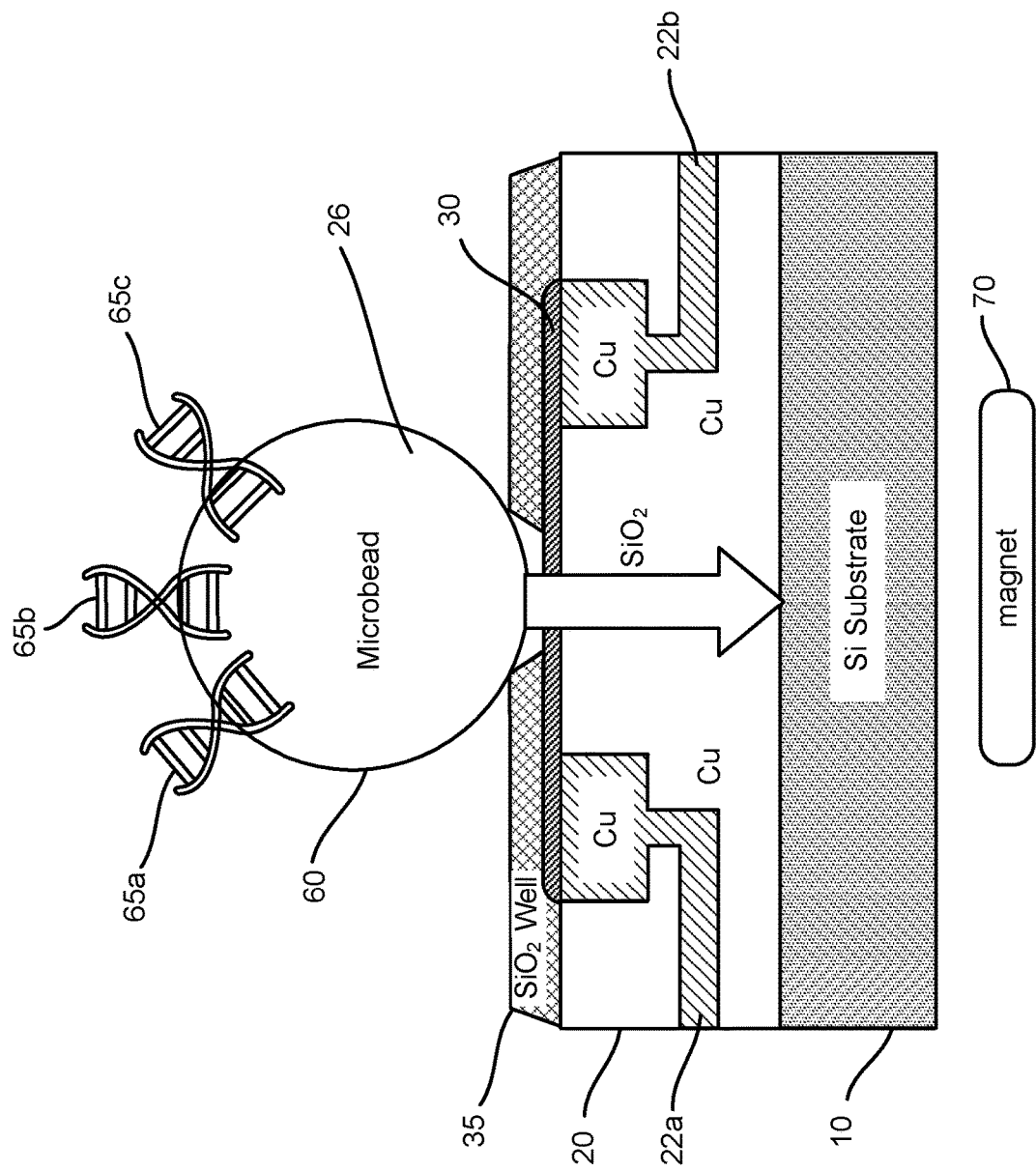
FIG. 5A is an illustration of the substrate of FIG. 1A, having a silicon dioxide layer positioned above a graphene layered reaction zone, and utilizing a magnetic field for the positioning of a nano- or micro-bead to be associated therewith.

Particularly, as shown in FIG. 5A, one or more nano- or micro-bead 60 of the disclosure may be configured for facilitating the performance of a bio-chemical reaction such as on a reaction surface 26 of the sensor device 1. For instance, in particular embodiments, each of the one or more microbeads may include a biological material or a chemical material, associated therewith. In such an instance, the bead 60 may be introduced to the surface 26 of the sensor device 1 of the system, such as for nucleic acid sequencing, in such a manner that it is drawn or otherwise attracted to the surface 26, such as by electro-magnetism. For instance, the bead 60 may be configured to include electric charge and/or paramagnetic properties so as to assist it in being drawn into proximity of a reaction location 26 positioned on a surface 21 of the device 1, such as where the nucleic acid sequencing reaction may take place. Hence, the device may include an electro-magnetic field generating component 70 that is configured to apply an electro-magnetic field that is focused within the reaction zone 26 so as to interact with the electric charge and/or paramagnetic properties of the bead 60 thereby drawing it into proximity of the surface 21 and/or in to the reaction zone 26, such as via electo-magnateism. In this instance, the layers and other components of the sensor device 1 are configured in such a manner that the reaction zone 26 need not include bounding members, or if included the bounding members may be thin, allowing for a higher density of wells on the array.

Figure 5B:
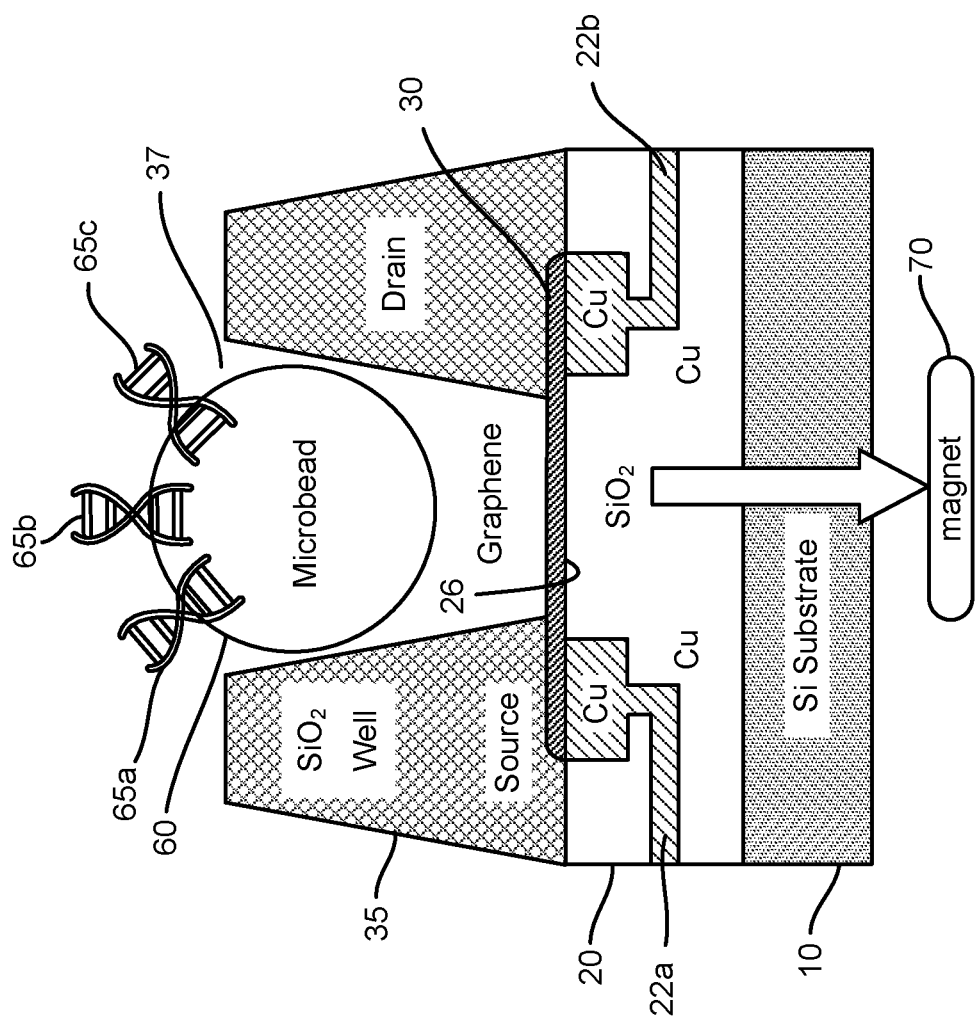
FIG. 5B is an illustration of the substrate of FIG. 1D, having a silicon dioxide layer positioned above a graphene layered reaction zone, and utilizing a magnetic field for the positioning of a nano- or micro-bead to be associated therewith.

Alternatively, in other embodiments, such as presented in FIG. 5B, the bio-chemical sensor device 1 may include a well structure 38 that is configured for receiving one or more nano- or micro-beads, such as for nucleic acid sequencing therein. For instance, each of the one or more microbeads includes an analyte and/or reactant, which is configured for participating in a reaction, such as a nucleic acid hybridization and/or sequencing reaction. Accordingly, the sensor device 1 may include a reaction location 26 that may be configured as a surface within a well 38 of the device 1, such as where the reaction location 26 is proximate a channel and/or sensor of the device 1. The nano- or micro-bead 60 may be configured for use in a system for analysis of biological and/or chemical materials such as on or within a reaction surface 26, such as within a well 38 of the sensor device 1. In this and other instances, the bead 60 may be introduced to the surface 26 of the sensor device 1 of the system in such a manner that it is drawn or otherwise attracted toward the reaction surface 26, e.g., of a well structure 38, where the nucleic acid sequencing reaction may take place, such as by electro-magnetism.

For example, the bead 60 may be configured to have an electric charge property and the bead attracting mechanism 60 may be configured to emit an electric field that is opposite in nature to the charge on the bead and is thereby adapted for draw the bead 60 into proximity of the reaction surface 26. In such an instance, an electric field component generates an electric field to interact with the electric charge properties of the microbead. Hence, the microbead may be drawn to the reaction location using electrophoresis. In other instances, the bead 60 may be configured to include paramagnetic properties so as to assist it in being drawn or otherwise attracted toward reaction surface 26, e.g., into the well 38, and into proximity of the reaction zone, where the reaction may take place. The device, therefore, may include a magnetic field generating component 70 that is configured to apply an electro-magnetic field that is focused within the chamber 38 so as to interact with the paramagnetic properties of the bead 60 thereby drawing it into the chamber 38 and/or proximate the reaction surface 26, such as via magnetism. Particularly, in various embodiments, the bead attracting mechanism 60 may be configured to emit a magnetic field that is opposite in polarity to the paramagnetic properties of the bead and is thereby adapted for draw the bead 60 into proximity of the reaction surface 26. In such an instance, a magnetic field component generates a magnetic field to interact with the polar properties of the microbead. The use of magnetism and/or electrophoresis allows for thinner reaction location structures.

Figure 5C:
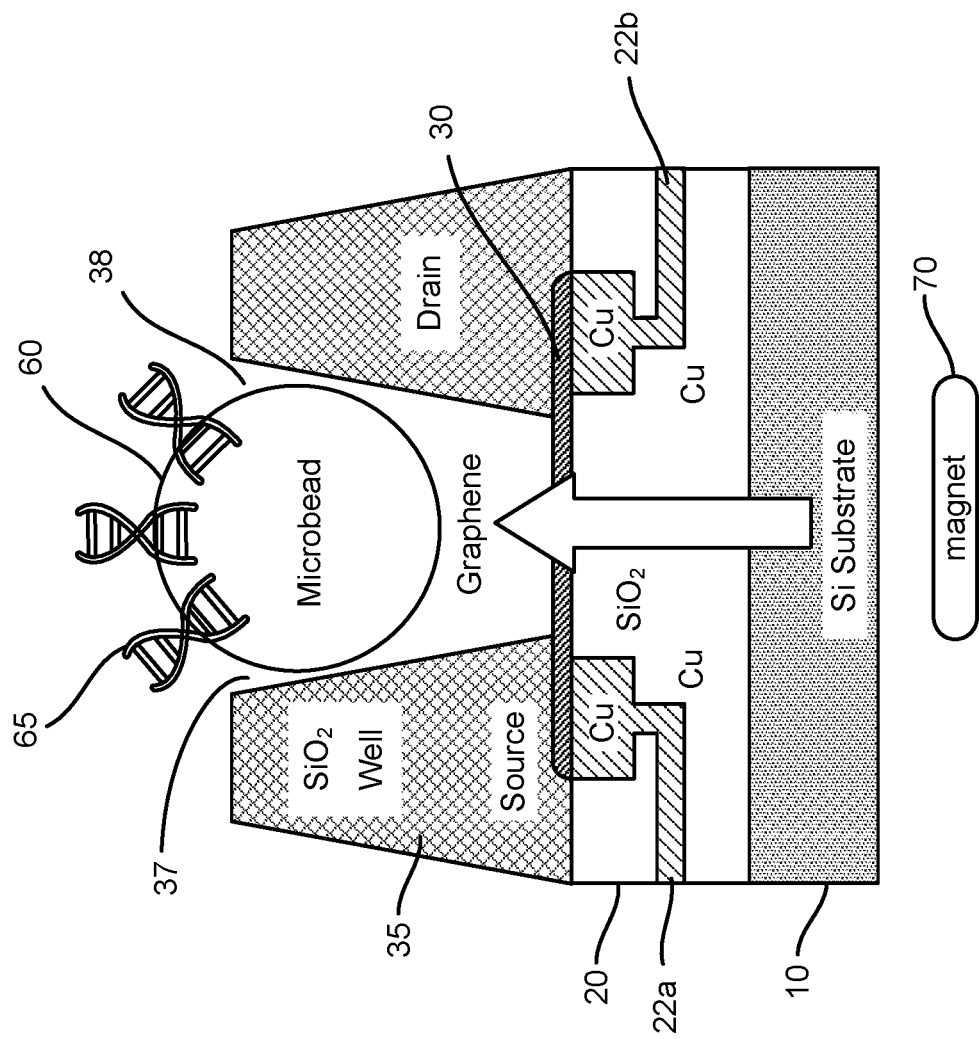
FIG. 5C is an illustration of the substrate of FIG. 5B, in an alternate configuration, such as utilizing a magnetic field reversal of a magnet to release a nano- or micro-bead.

Additionally, as illustrated in FIG. 5B, in some embodiments, the system and its components may be configured such that when the electro-magnetic field is generated it interacts with the bead 60 and/or a component associated therewith so as to pull the bead toward the reaction zone 26. In other embodiments, as illustrated in FIG. 5C, the system and its components may be configured such that when the electro-magnetic field is generated it interacts with the components of the bead 60 so as to push the bead away from the reaction zone 26. Accordingly, the electromagnetic fields can be generated and/or reversed so as to attract or repulse the nano-/micro-bead to or from the reaction location 26, such as to or away from a well 38, and thus utilizing an electronic and/or magnetic field, the nano- or micro-bead may be positioned within the device, such as within a well thereof.

Figure 5D:
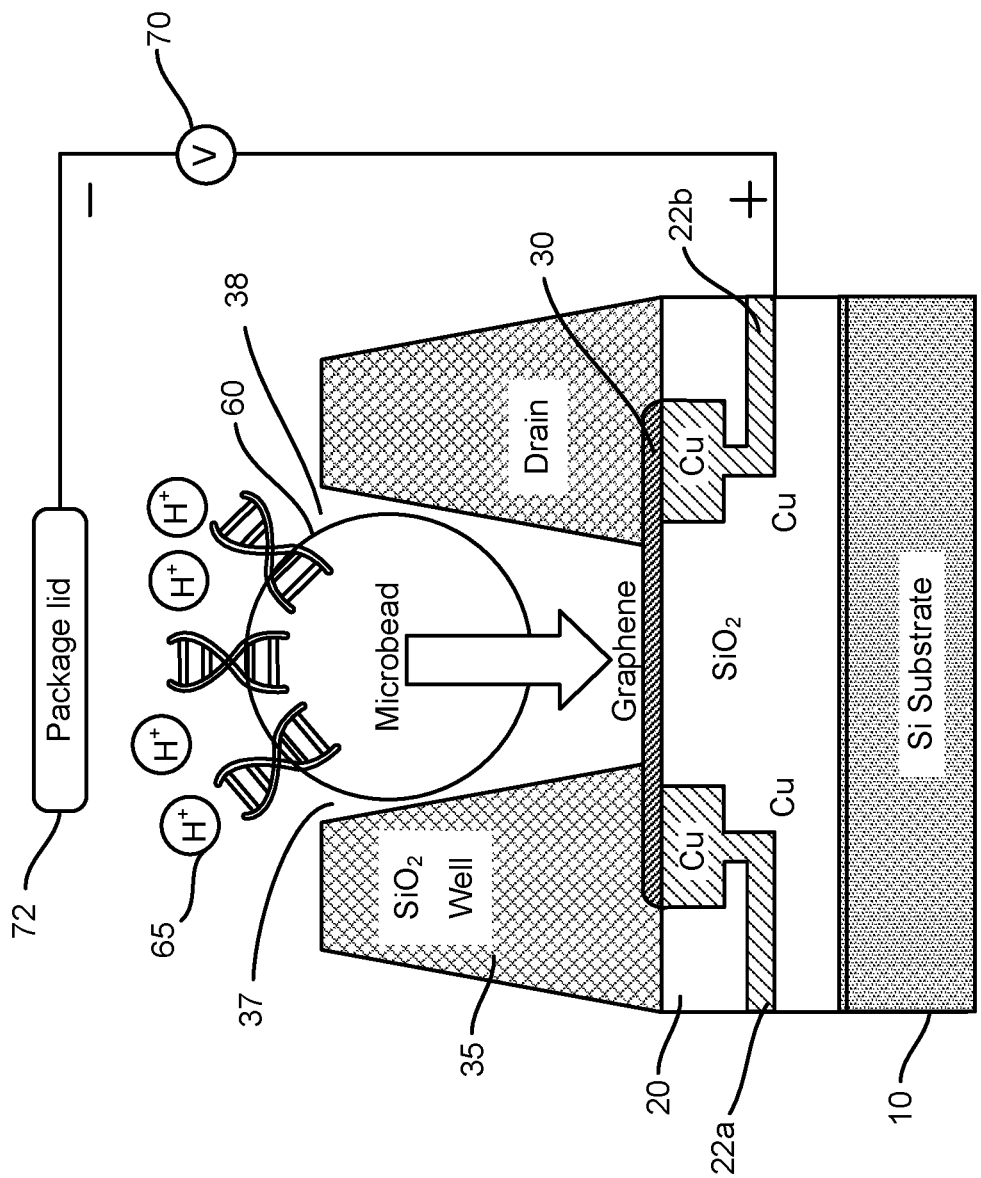
FIG. 5D is an illustration of the chemically-sensitive field-effect transistor of FIG. 4A, such as for a system for analysis of biological or chemical materials, utilizing an electric field for positioning of a nano- or micro-bead.

As illustrated in FIG. 5D a chemically-sensitive field-effect transistor 1 is provided, such as for a system for analysis of biological and/or chemical materials, such as by utilizing an electric and/or magnetic field generating mechanism such as for positioning of a nano- or micro-bead 60 in relation to the reaction surface 26. For instance, in particular instances, a voltage may be applied between a location above the solution of the solution gate 37 and a location on or below the reaction location 26, such as above the package lid 72 and/or below a metal component, e.g., a plate, below the package 72. In certain instances, the location below the reaction location 26 may include a metal or other conductive layer such as within the package or package substrate. Hence, in various instances, the field generating mechanism 70 may be employed to generate and/or reverse an electric or magnetic field so as to insert or eject one or more beads from one or more wells, sensors, and/or channels associated therewith, either entirely or selectively.

Figure 5E:
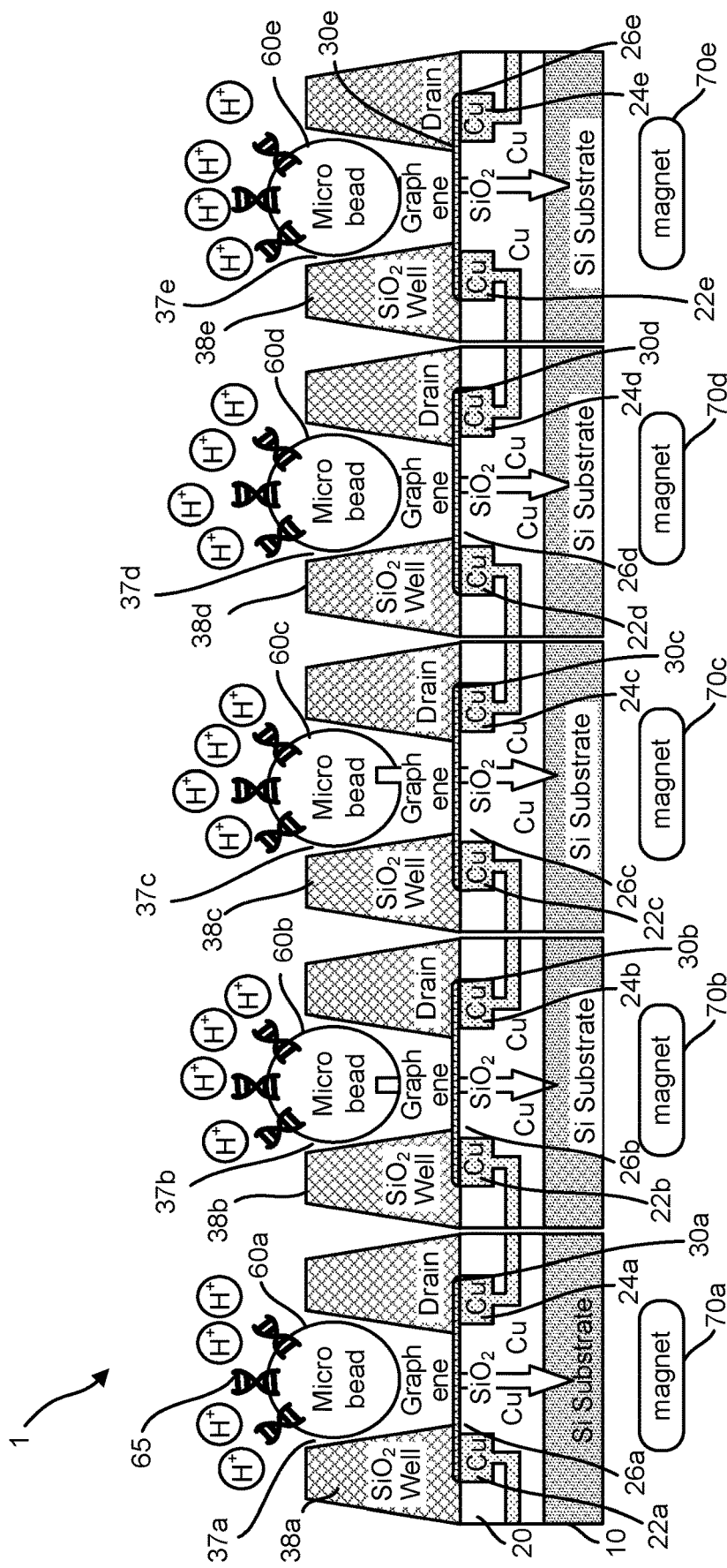
FIG. 5E is an illustration of an array of chemically-sensitive field-effect transistors for a system for analysis of biological or chemical materials utilizing multiple magnets for generating a plurality of magnetic fields for positioning of nano- or microbeads within the wells.

Particularly, as set forth in FIG. 5E, an array 1 of chemically-sensitive field-effect transistors for a system for analysis of biological or chemical materials is provided. The array 1 includes a multiplicity of wells 38a-e each forming a reaction location 26a-e whereon a bio-chemical reaction may take place. Additionally, each reaction location 26 is associated with a field generator 70a-e, e.g., a magnet, which is configured so as allow for the selective filling of the reaction locations 26 with one or more types of nano- or microbeads 60a-e. Accordingly, by utilizing multiple field generators 70a-70e, e.g., multiple magnets, for generating a plurality of electro-magnetic fields, the nano- or micro-beads 60a-e may be positioned within the plurality wells 38a-e. Such positioning may be selective such as by selecting which generators will be on, off, or reversed, so as to fill or not fill their respective wells 38a-e, as desired. In various embodiments, the electromagnetic fields for any given well 38 may be reversed so as to expel a bead 60 from the well 38 and/or reaction zone 26.

Particularly, in a further aspect of the present disclosure, a system having an array of chemically-sensitive transistors, such as field effect transistors (FET) including a plurality of chambers 37a-e having well structures formed therein is provided. In such an instance, the wells 38a-e may be structured as or may otherwise include reaction locations, 26a-e, wherein one or more chemical reactions may take place. In such an embodiment, the system may include one or more fluidics components having one or more fluid sources, e.g., reservoirs, containing one or more fluids therein and configured for delivering the fluid from the reservoir to the reaction chamber, such as for the detection of a biologic and/or the performance of one or more chemical and/or biological reactions, such as a nucleic acid sequencing reaction. Accordingly, the fluidics component, e.g., the fluid source, may be in fluidic communication with the FET device configured for biological and/or chemical analysis, and may be configured for controlling a flow of reagents over the array.

Accordingly, in certain instances, the fluid may include one or more reactants, such as one or more analytes necessary for performing a sequencing reaction, as herein described. In a particular embodiment, the fluid may include one or more, e.g., a plurality of microbeads 60, having a nucleic acid template 65 attached thereto, for instance, where the template is a DNA or RNA molecule to be sequenced, and the fluid containing the microbead 60 is to be delivered to the well 38 such as for carrying out the sequencing reaction. In such an embodiment, one or more of, e.g., each, of the plurality of microbeads may be configured so as to have electric charge and/or paramagnetic properties. The device may additionally include an electric and/or magnetic field component, e.g., having an electric and/or magnetic field generator, such as where the electric and/or magnetic field component is configured to generate an electric and/or magnetic field so as to interact with the electric and/or magnetic charge properties of each of the plurality of microbeads to attract the microbeads into a reaction location, such as a reaction surface, a channel, a well, a chamber, and/or a sensor of the FET device, such as by using electrophoresis and/or magnetism.

Hence, one or more, e.g., a plurality of microbeads 60a-e, may be drawn onto or into a reaction location of the plurality of reaction locations 37a-e, which locations may be formed as wells, e.g., one or more thin wells. The use of magnetism or electrophoresis allows for thinner reaction location structures. In particular instances, electric and/or magnetic field generator may be configured for drawing and/or positioning the microbeads within the well structure 37, such as in proximity to a channel or chamber of the device, and in other instances, the electric and/or magnetic field generator may be configured for reversing the electrical and/or magnetic field so as to repulse the microbead(s) 60 from the reaction location, channel, and/or chamber 37. In various instances, an array of reaction locations may be provided each having a magnet 70a-e that allows for selective filling of the reaction locations with different numbers and/or types of microbeads 60, such as at select reaction locations 37a-e. In such an instance, multiple electric and/or magnetic field generators for selective filling of reaction locations, e.g., wells.

Accordingly, one aspect of the present disclosure is a system and/or a method for positioning one or more, e.g., a plurality, of microbeads 60 within a reaction or plurality of reaction locations 37 for biological or chemical analysis, such as for nucleic acid sequencing. The system may include a CMOS FET device having an integrated circuit structure configured for performing a biological or chemical analysis, such as within a plurality of nano- or micro-reaction wells, as described above, having a fluidic component 120, a circuitry component 140, and/or a computing component 150, and the method may include one or more of the following steps. For instance, the method may include the fluidic component 120 introducing a fluid to be in contact with the device 1, such as where the fluidics component is configured to control a flow a fluid of reagents over the array 1, and the fluid may include one or more microbeads 60 that may have electric charge and/or paramagnetic properties. In such an instance, the device may include an integrated circuit structure, a plurality of reaction locations 37 having one or more wells, a plurality of sensors and/or a plurality of channels, and/or an electric and/or magnetic field component 70. The electric field and/or magnetic field component 70 may be configured to activate the electronic and/or magnetic field, and the method may also include activating an electric and/or magnetic field so as to interact with the electric and/or paramagnetic properties of each of the microbeads 60. The method may additionally include drawing the one or more microbeads 60 into proximity with a reaction zone 26 of the plurality of reaction locations 37 using electrophoresis and/or magnetism. In certain instances, the method may include positioning the one or more microbeads within the one or more reaction locations for biological or chemical analysis.

In particular instances, the electric and/or magnetic fields may be generated by the plurality of electric and/or magnetic field generators 70, e.g., included in the integrated circuit structure, in all or only a subset of the plurality of reaction locations 37 so as to only attract a plurality of microbeads 60 to the subset of reaction locations, such as for selectively filling the plurality of reaction locations 37 with the plurality of microbeads. In such an instance, different types of microbeads may be attracted to different reaction locations, such as by pulsing the voltage and/or magnetic generators and/or keeping the same constant. Particularly, where an electric field generator 70 is provided the voltage applied to the device 1 may be variable or constant and may be less than about 10V, such as about less than 8V, or less than about 6V, including less than about 4V or about 2V or 1V. The voltage may be applied between a location above the fluid 72 and a location on or below the reaction zone 26, such as above the package lid and/or below the metal plate below the package. In certain instances, the location below the reaction location may be a metal or conductive layer such as within the package or package substrate. The method may also include the step of reversing the electric or magnetic field so as to eject the plurality of beads from the plurality of wells, sensors, and/or channels, either entirely or selectively.

Further, as indicated, each or a subset of the plurality of reaction locations may be utilized to generate electric fields to attract a microbead thereby allowing for programmability to each or a subset of reaction locations, for instance, 99% or 95% or 90% or 85%, or 80% or less of the plurality of wells are occupied with a microbead. Hence, the electric and/or magnetic field may be generated in only a subset of the plurality of wells 38a-e, sensors or channels to only attract a plurality of microbeads 60a-e to the subset. Likewise, a plurality of electric and/or magnetic field generators 70a-e for selective filling the plurality of wells 38, sensors or channels with the plurality of microbeads, and/or ejecting the plurality of beads 60 from the plurality of wells 38, sensors or channels. In such an instance, the electric and/or magnetic field generator may be an electric source, a permanent magnet and/or an electromagnet. As indicated, the plurality of magnetic field generators is configured to reverse the magnetic field to eject the plurality of microbeads 60 from the plurality of reaction locations 37 or a subset thereof.

Additionally, in one aspect of the present disclosure, a device, system, and/or method for verifying well occupancy for a plurality of wells 38a-e for analysis of biological or chemical materials may be provided. The system may include a device for receiving a fluid containing the plurality of microbeads 60. Particularly, the device may include a processor, a CMOS structure having an integrated circuit, a plurality of wells 38, and a plurality of sensors within the CMOS structure. Each of plurality of wells 38 may be configured to receive a microbead 60 of the plurality of microbeads, and the CMOS structure may include a mechanism 70 for drawing and/or ejecting the beads into or out of the wells. Hence, the method may include the step of flowing the plurality of microbeads 60 over and/or into the plurality of reaction locations 26/37 and/or wells 38 and/or may include determining, e.g., through electrical and/or magnetic sensing if a reaction location 26/37 and/or well 38 is occupied or unoccupied and/or if a location 26/37 contains one or multiple microbeads 60.

Consequently, the processor 140 may be configured to determine if a well is unoccupied and/or if the well contains one or more, e.g., multiple microbeads. In certain instances, the processor 140 may also be configured to eliminate or modify one or more of the measurements, such as based on the number of wells occupied or unoccupied, e.g., the number of wells containing none, one or multiple microbeads. For instance, the processor 140 may be configured to eliminate from the measurement the number of wells unoccupied and the number of wells containing multiple microbeads, or compensate in the measurement for the number of wells unoccupied and the number of wells containing multiple microbeads, and the like. In such instances, the measurement may be a shift in an I-V or I-Vg curve, as explained below. In particular instances, the processor 140 may be configured to eliminate from the measurement the number of wells unoccupied and the number of wells containing one or multiple microbeads and/or to compensate in the measurement for the number of wells unoccupied and the number of wells containing one or multiple microbeads. Accordingly, in some embodiments, the measurement may be a shift in an I-V or I-Vg curve, such as one or more of: generating a plurality of I-V or I-Vg curves so as to determine a shift in response to a chemical reaction occurring on or near the chemically-sensitive field effect transistor; generating a chemically-sensitive field-effect transistor I-V or I-Vg curve in response to a chemical reaction occurring on or near the chemically-sensitive field-effect transistor so as to detect a change in the slope of the I-V curve; and/or to sense shifts in a capacitance as a function of a gate voltage.

As indicated above, in particular embodiments, the field effect transistor may be configured as a complementary oxide semiconductor that is further adapted so as to be cavitated, so as to include one or more reaction chambers that are positioned so as to align with a gate region of the FET. In such instances, the FET may be in contact with a fluidic source so as to form an ISFET. Accordingly, the CMOS-ISFET may be configured to run one or more chemical and/or biological reactions within its various chambers, such as a DNA sequencing reaction, and the like, such as proximate a solution gated reaction zone. For these purposes, the ISFET may include a processor configured for controlling the performance of the one or more reactions, e.g., involving a biological or chemical material, so as to obtain reaction results, and for analyzing those results, for instance, based on detecting and/or measuring changes in a voltage (V) potential, current (I), or capacitance occurring within the gate region on the chemically-sensitive field effect transistor.

Figure 6A:
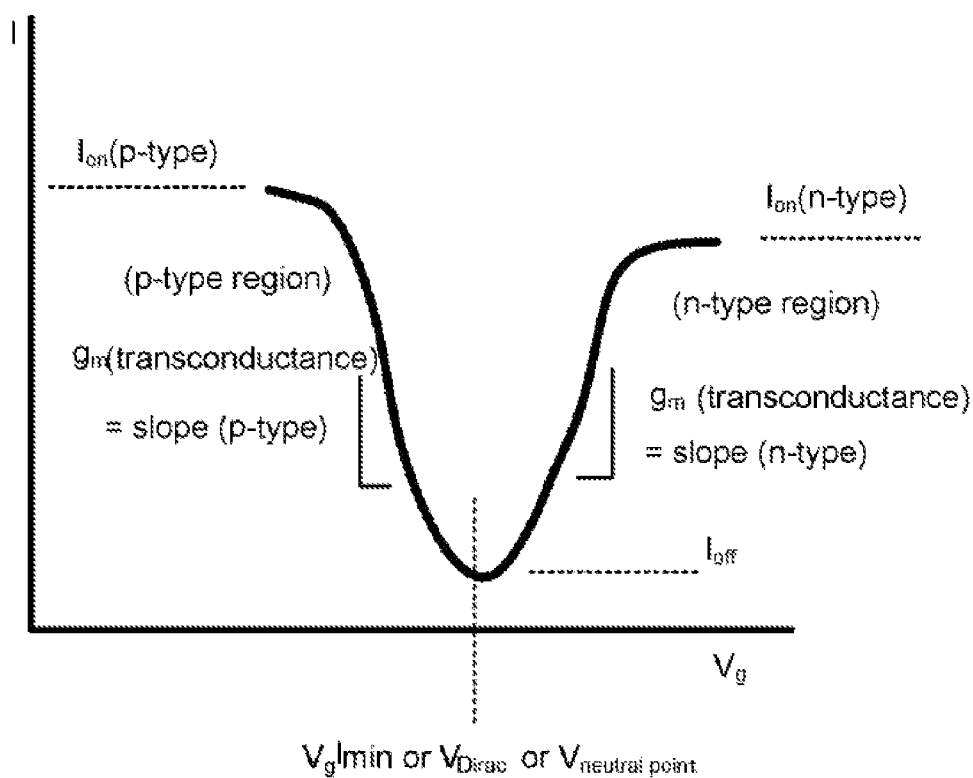
FIG. 6A is a graph of an I-Vg curve with characteristics that are used to categorize I-V g curves.

Particularly, as can be seen with respect to FIG. 6A, the processor, such as a signal processor 151, may be configured so as to generate one or more current (I) vs. voltage (V) curves, such as where the current I of the I-V curve is the current applied between the source 22 and drain 24 of the chemically sensitive solution gated field effect transistor and/or where the gate voltage (Vg) of the I-Vg curve is a gate 26/37 voltage applied to the chemically-sensitive field effect transistor 1. In such an instance, the gate voltage Vg of the I-Vg curve may be a top and/or a back gate voltage that may be applied to the chemically sensitive field effect transistor 1 through a top (or front) and/or back of the device, respectively. In particular embodiments, the gate voltage Vg of the I-Vg curve may be a solution gate voltage such as applied to the chemically sensitive field effect transistor through a solution flowed over a portion, e.g., a chamber 38, of the device 1. In some embodiments, the reference I-Vg curve and/or a chemical reaction I-Vg curve may be generated in response to the biological material and/or chemical reaction that is to be detected and/or occurs over or near the chemically-sensitive field effect transistor, such as within a chamber or well 38 of the FET structure. In various embodiments, the processor 150 may be configured to determine differences in relationships between a generated reference I-Vg curve and/or chemical reaction I-Vg curve. In certain instances, a circuitry component 140 may be included where the circuitry component may include at least one analog-to-digital converter 141 that is configured for converting analog signals, such as obtained as a result of the performance of the reaction(s) within the reaction well 38, or array of wells, into digital signals, such as may be sent back to the computing component 150 for further processing.

Accordingly, in another aspect of the disclosure, a chemically-sensitive field effect transistor device 1 may be provided, wherein the device may include a structure having a conductive source 22 and drain 24 as well as having a surface or channel 26 extending from the conductive source to the conductive drain, such as where the surface or channel may include a one-, two-, or three-dimensional transistor material 30. The device 1 may also include a computing component 150 having or otherwise being associated with a processor such as where the processor is configured for generating a reference I-Vg curve and/or generating a chemical reaction I-Vg curve, in response to the chemical reaction occurring within a chamber 37 of the chemically-sensitive field effect transistor 1, and may be configured to determine a difference between the reference I-Vg curve and the chemical reaction I-Vg curve. Specifically, FIG. 6A depicts a graph illustrating an I-Vg curve calling out the various characteristics that may be used to categorize I-V g curves, and FIG. 6B depicts a graph of an I-Vg curve illustrating the results of a single difference and that of multiple differences.

Figure 6B:
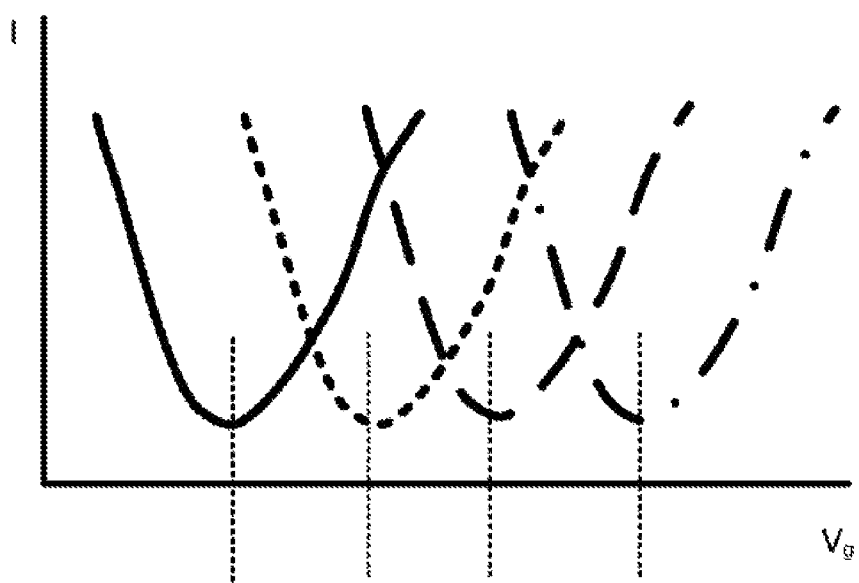
FIG. 6B is a graph of an I-Vg curve illustrating a single difference or multiple differences.
Figure 6C:
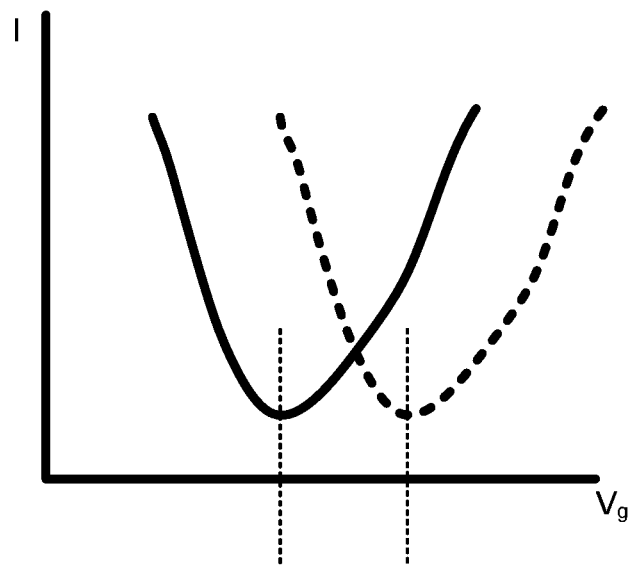
FIG. 6C is a graph of an I-Vg curve illustrating a shift in the I-Vg curve.
Figure 6D:
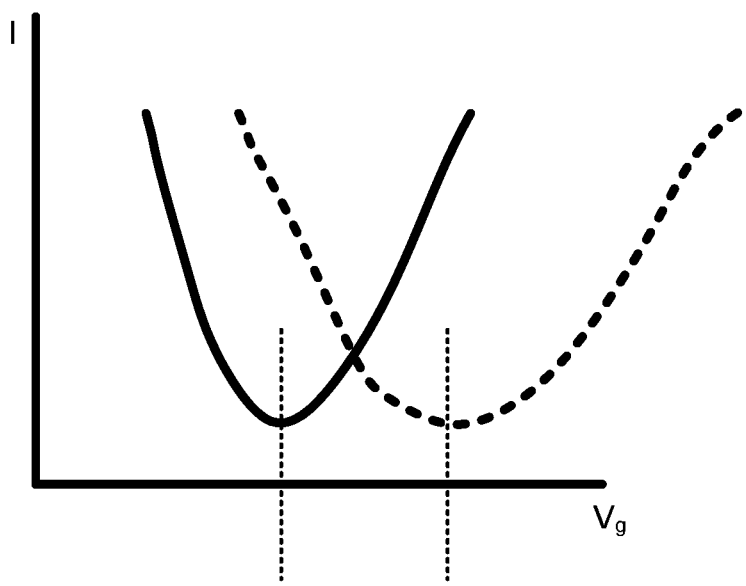
FIG. 6D is a graph of an I-Vg curve illustrating a change in the shape of the I-Vg curve.

Particularly, as can be seen with respect to FIG. 6B, the difference between the reference I-Vg curve measurement and the chemical reaction I-Vg curve measurement is a shift in a minimum current point of the Vg value of the chemical reaction I-Vg curve relative to a minimum current point of the Vg value of the reference I-Vg curve. As can be seen, this shift is from left to right along the Vg axis. Hence, as can be seen with respect to FIG. 6C, in some instances, a change in reaction conditions that result in a change in the I-Vg curve may be demarcated by a shift in the I-Vg curve, or as depicted in FIG. 6D, it may be demarcated by a change in the shape of the I-Vg curve. More particularly, as exemplified in FIG. 6C, in one embodiment, the difference between the reference I-Vg curve and the chemical reaction I-Vg curve may be a change in the slope of the chemical reaction I-Vg curve relative to a change in the slope of the reference I-V g curve. Likewise, as exemplified in FIG. 6D, the difference between the reference I-Vg curve and the chemical reaction I-Vg curve may be an overall change in the shape of the chemical reaction I-Vg curve relative to an overall change in shape of the reference I-Vg curve.

Figure 6E:
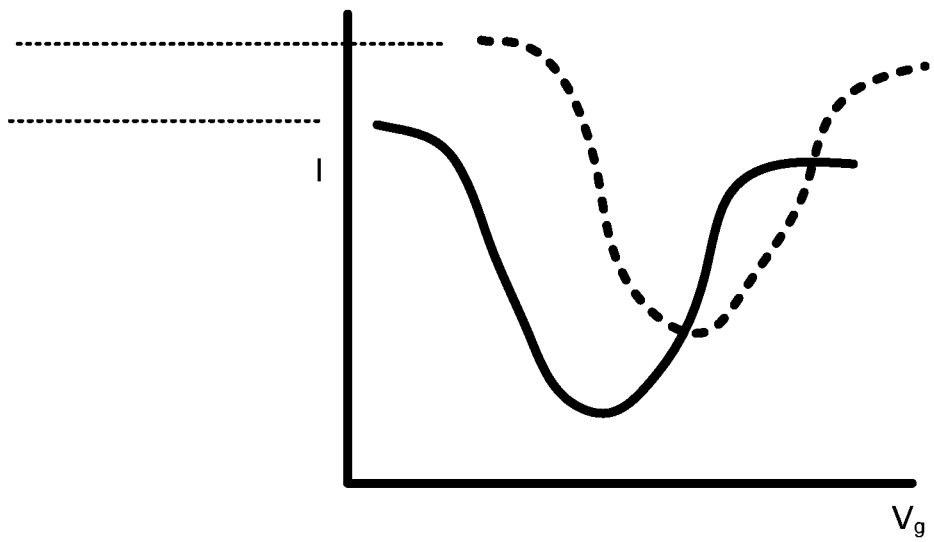
FIG. 6E is a graph of an I-Vg curve illustrating a change in the level of the I-Vg curve (Ion in p-type region).
Figure 6F:
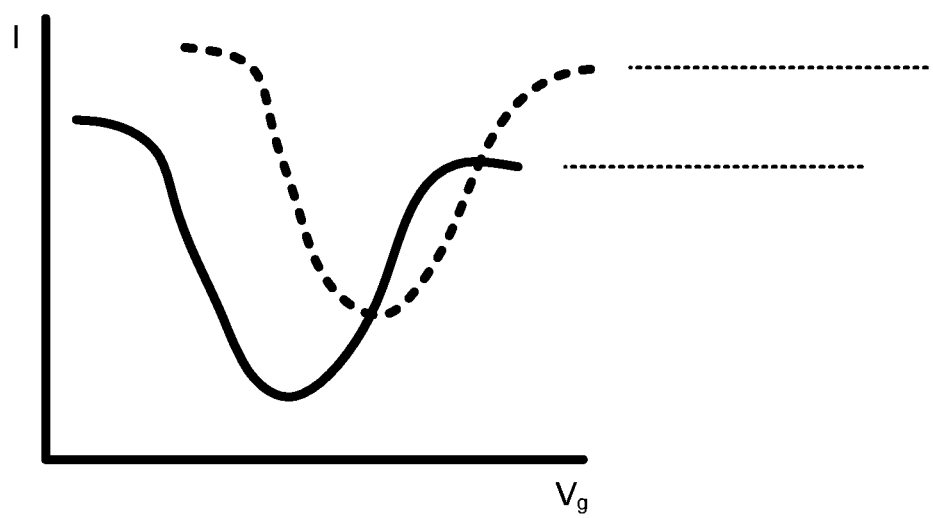
FIG. 6F is a graph of an I-Vg curve illustrating a change in the level of the I-Vg curve (Ion in n-type region).

In other instances, as can be seen with respect to FIGS. 6E and 6F, the difference between the reference I-Vg curve and the chemical reaction I-Vg curve may be a shift in an Ion value of the chemical reaction I-Vg curve relative to a shift in an Ion value of the reference I-Vg curve, for instance, where the Ion values are taken from a p-type (FIG. 6E) or n-type (FIG. 6F) section of the I-Vg curve (see FIG. 6A). For example, the measurements of the slopes may be taken from the steepest and/or flattest sections on the p-type and/or n-type portions of the I-Vg curves. Specifically, FIGS. 6E and 6F depict graphs of I-Vg curves illustrating a change in the level of the I-Vg curve where the ion is in a p-type region (FIG. 6E), and a change in the level of the I-Vg curve where the Ion value is in a n-type region (FIG. 6F).

Figure 6G:
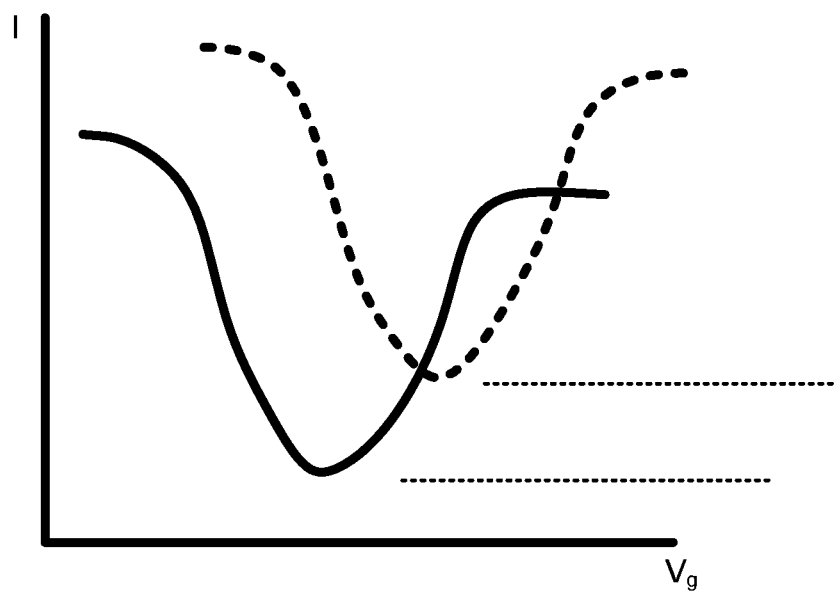
FIG. 6G is a graph of an I-Vg curve illustrating a change in the level of the I-Vg curve (Ioff).
Figure 6H:
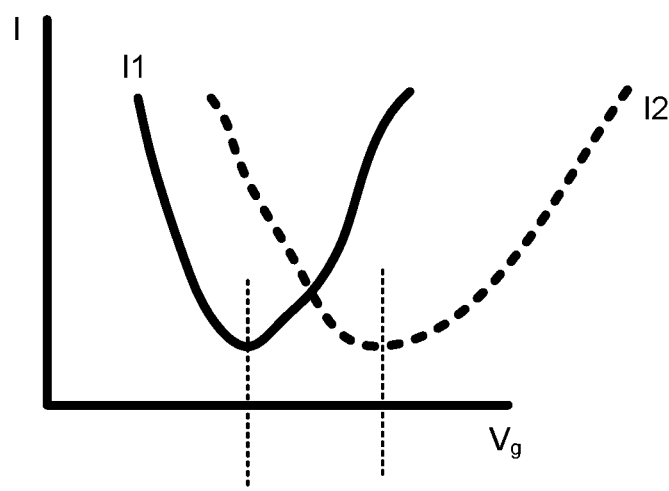
FIG. 6H is a graph of an I-Vg curve illustrating a fit polynomial or other fitting line to curve and use coefficients as read criterion.
Figure 6I:
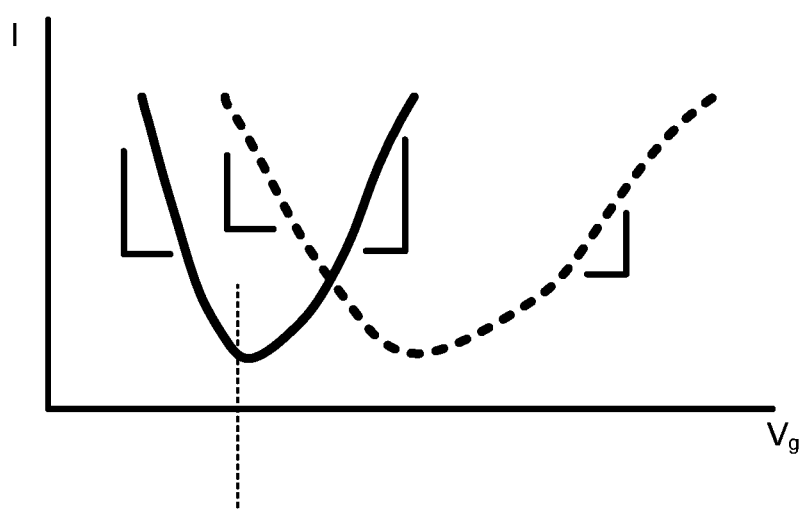
FIG. 6I is a graph of an I-Vg curve illustrating a check-slope of the I-Vg curve on one or both sides (Gm & proportional to mobility), and use of a solution gate and backgate in combination to improve a signal and move the curve where desired.

Additionally, in particular instances, the difference between the reference I-Vg curve and the chemical reaction I-Vg curve may be a shift in an Ioff value of the chemical reaction I-Vg curve relative to an Ioff value of the reference I-Vg curve. Particularly, FIG. 6G depicts a graph of an I-Vg curve illustrating a change in the level of the I-Vg curve (Ioff). More particularly, in such embodiments, as depicted in FIG. 6H, the difference in the overall shape of the I-Vg curves may be determined by first fitting a polynomial or other fitting line to each of the I-Vg curves and then comparing the coefficients of those fitting lines. Specifically, FIG. 6H depicts a graph of an I-Vg curve illustrating a fit polynomial or other fitting line to curve and use coefficients as read criterion. In other embodiments, the difference between a reference I-Vg curve and the chemical reaction I-Vg curve is based on more than one chemical reaction I-V g curve. Further, FIG. 6I depicts a graph of an I-Vg curve illustrating a check-slope of the I-Vg curve on one or both sides (Gm & proportional to mobility), and use of a solution gate and backgate in combination to improve a signal and move the curve where desired.

It is to be noted, with respect to FIGS. 5B and 5C, when no microbead 60 is present in the well structure 38, an electric signal may be transmitted to the computing component 150. In such an instance, the processor may be configured to eliminate from the measurement the number of wells 38 that are unoccupied, or at least to compensate in the measurement for the number of wells 38 that are unoccupied, such as where the measurement may be a shift in the I-V curve and/or I-Vg curve. Likewise, when two or more microbeads 60a and 60b are present in the well structure 38, an electric signal may be transmitted to the computing component 150. In such an instance, the processor may be configured to eliminate from the measurement the number of wells 38 containing multiple microbeads 60, or at least compensate in the measurement for the number of wells 38 containing multiple microbeads 60, such as where the measurement may be recognized as a shift in the I-V curve and/or I-Vg curve.

Accordingly, as can be seen with respect to FIGS. 6A-6I, in particular embodiments, the FET and/or processor may be configured to respond to a shift in the I-V or I-Vg curve, such as where the curve is shifted in response to the detection of a biological compound and/or the result of a reaction taking place in or on a surface 26 of the FET device 1. In some instances, the I-V/I-Vg curve may be produced and/or shifted in response to a chemical reaction occurring on a reaction layer 34/36 and/or the surface of a 1D or 2D, e.g., graphene, surface 30 of the field effect transistor 1, such as resulting from the detection of a biological compound or reaction occurring within the well structure 38 of the device. Hence, the FET and/or processor may be configured so as to shift the I-V curve or I-Vg curve such as in response to the chemical reaction.

Figure 7A:
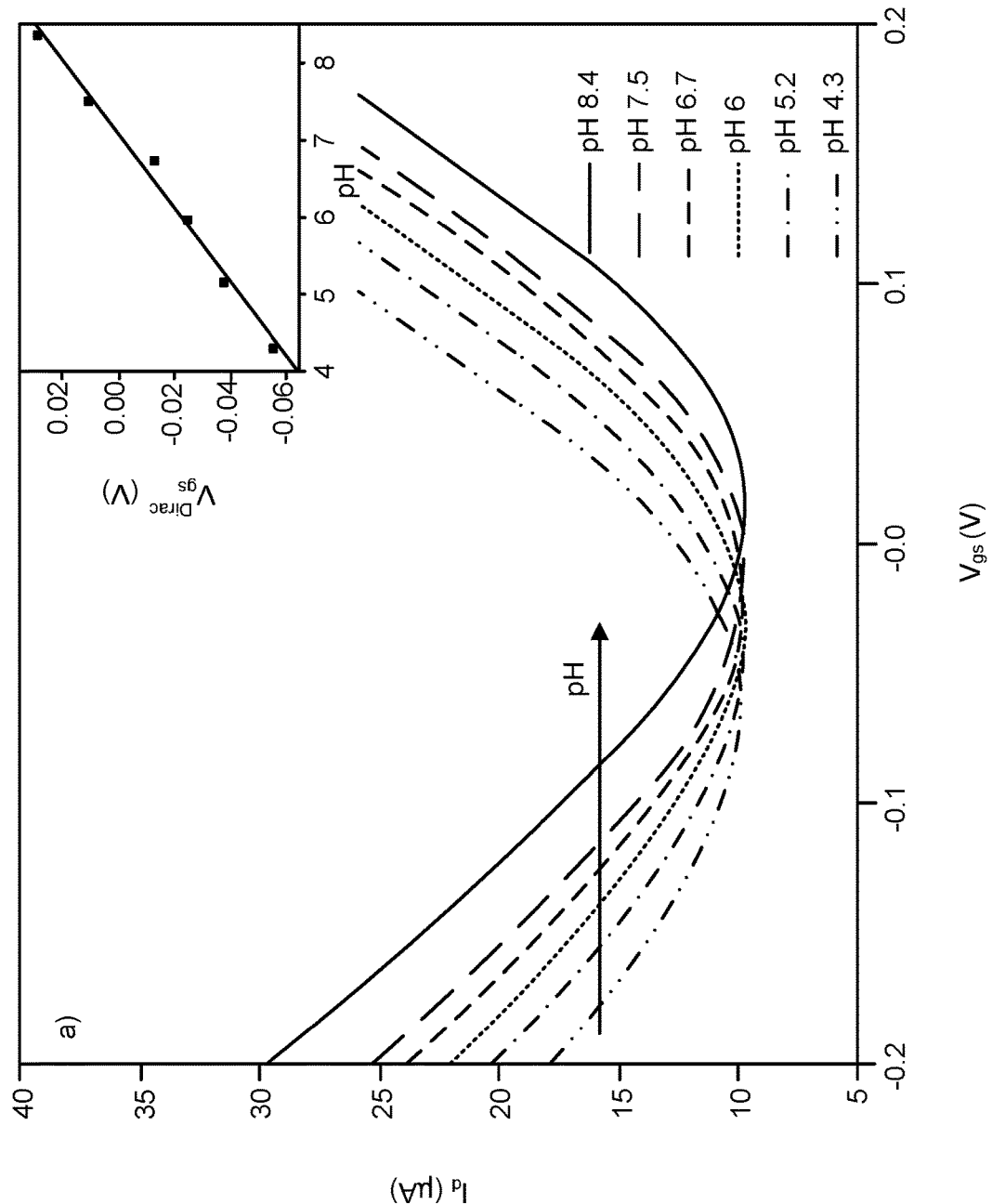
FIG. 7A is a graph of an I-Vg curve for various pH values.
Figure 7B:
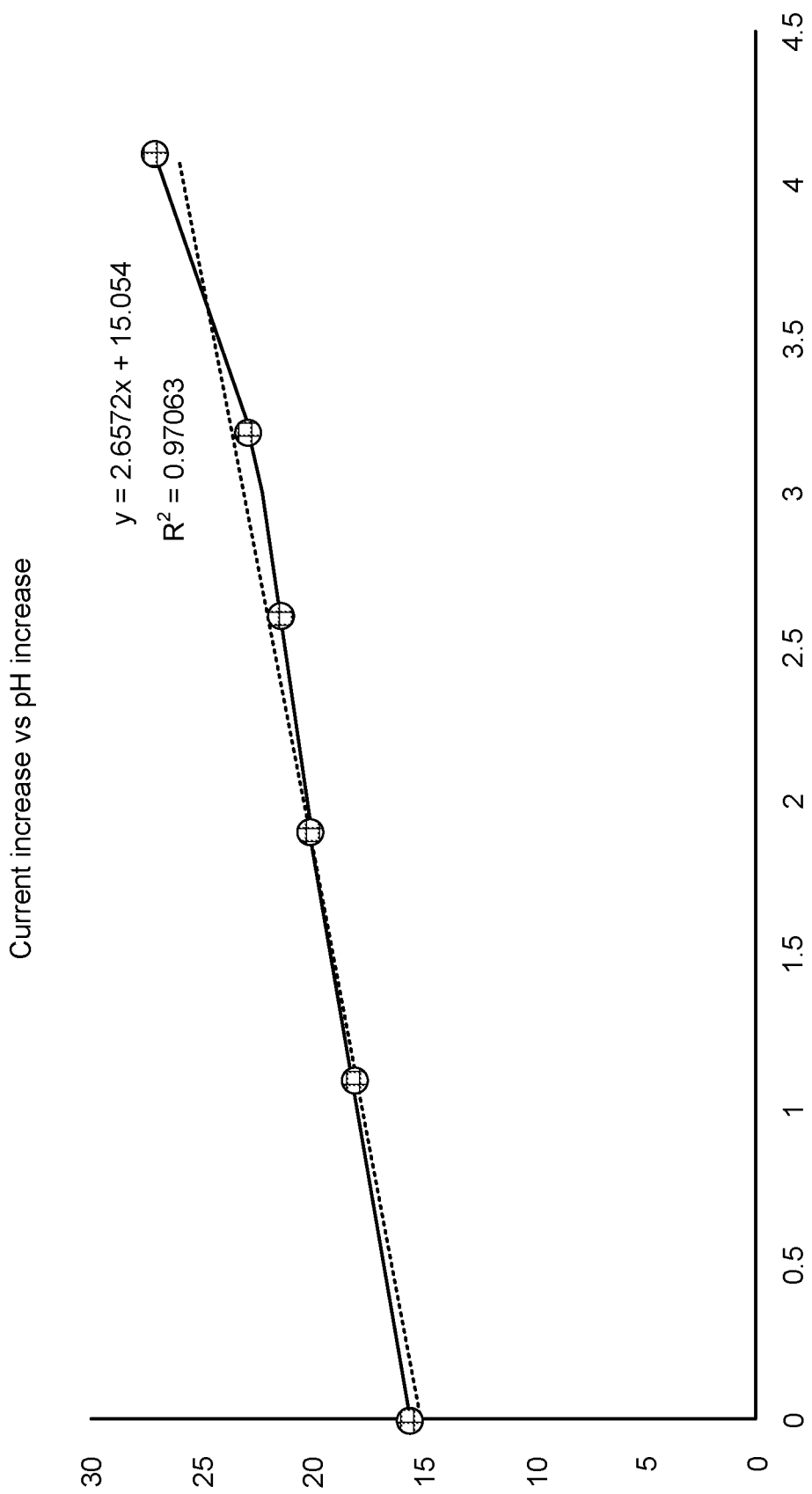
FIG. 7B is a graph of current increase vs. pH increase.
Figure 7C:
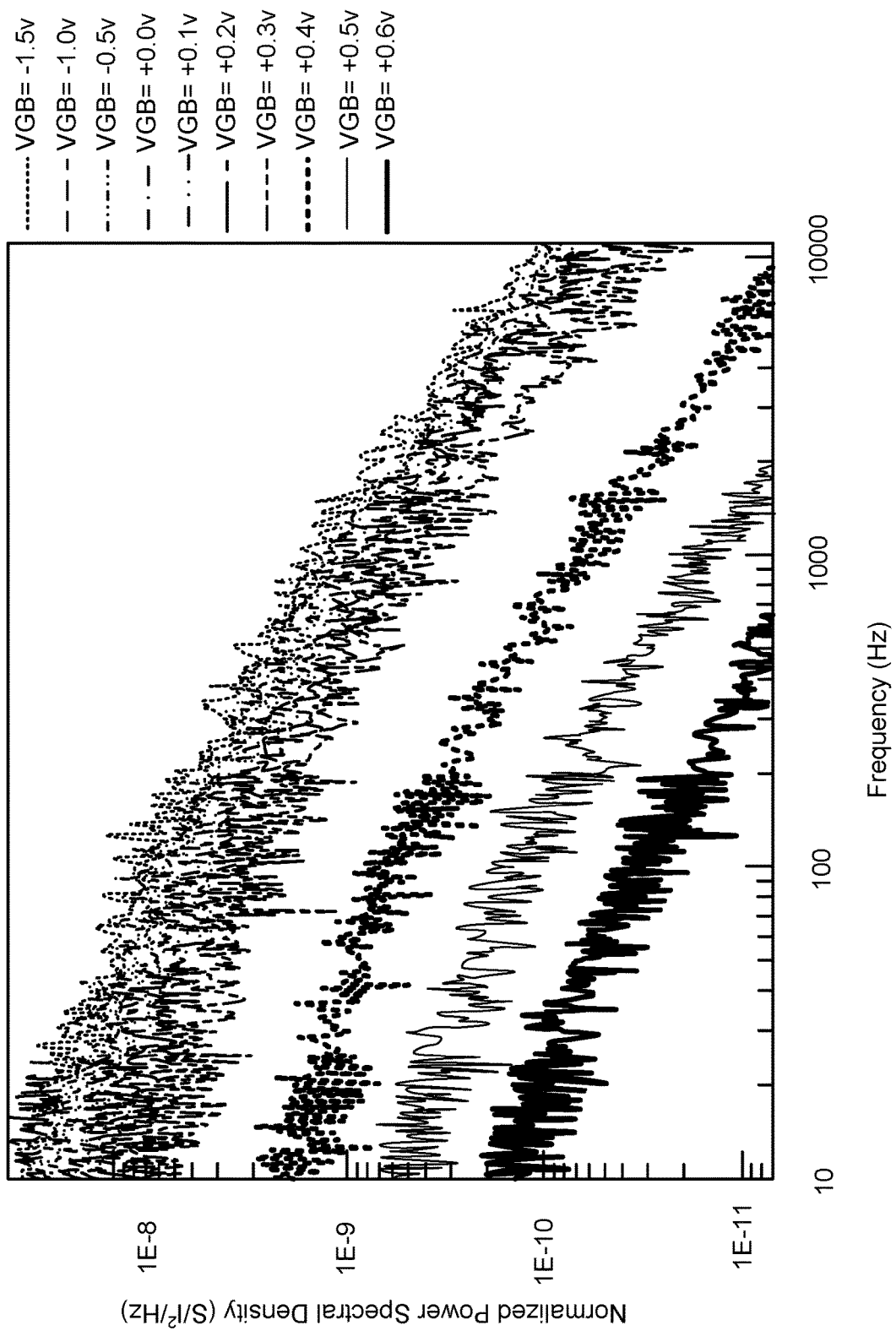
FIG. 7C is a graph of frequency vs. normalized power spectral density for silicon ISFET.
Figure 7D:
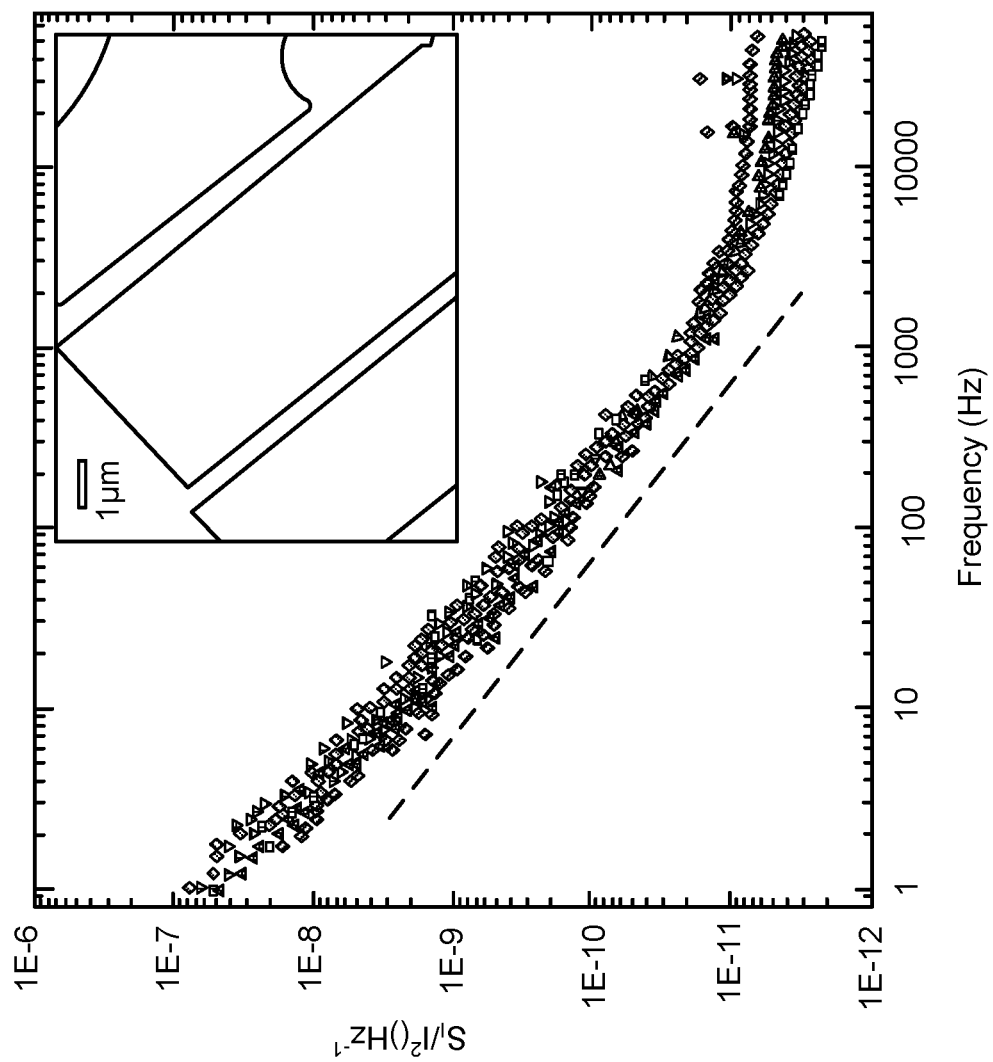
FIG. 7D is a graph of frequency vs. normalized power spectral density for a typical graphene FET.
Figure 7E:
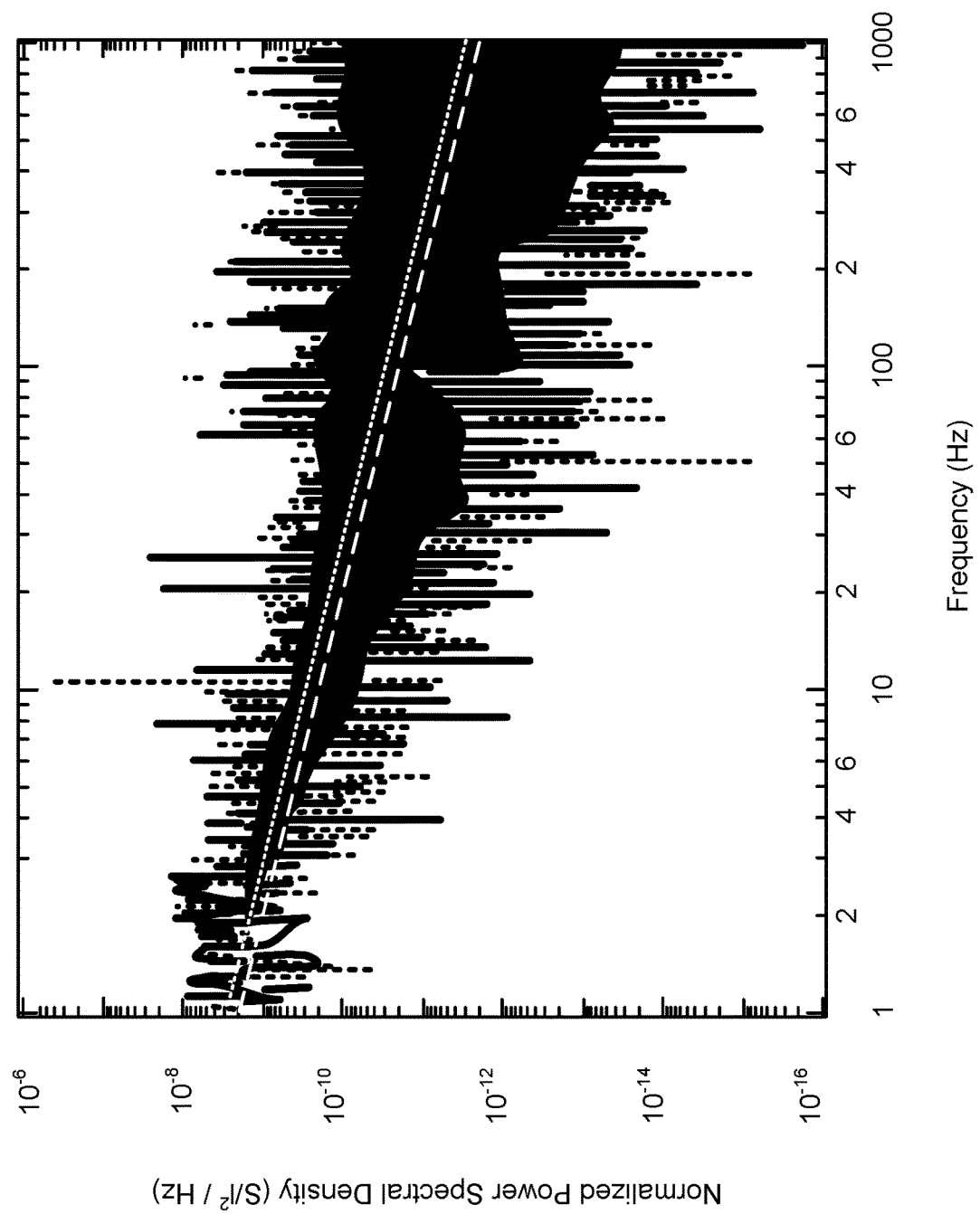
FIG. 7E is a graph of frequency vs. normalized power spectral density for a graphene FET of the present invention.
Figure 7F:
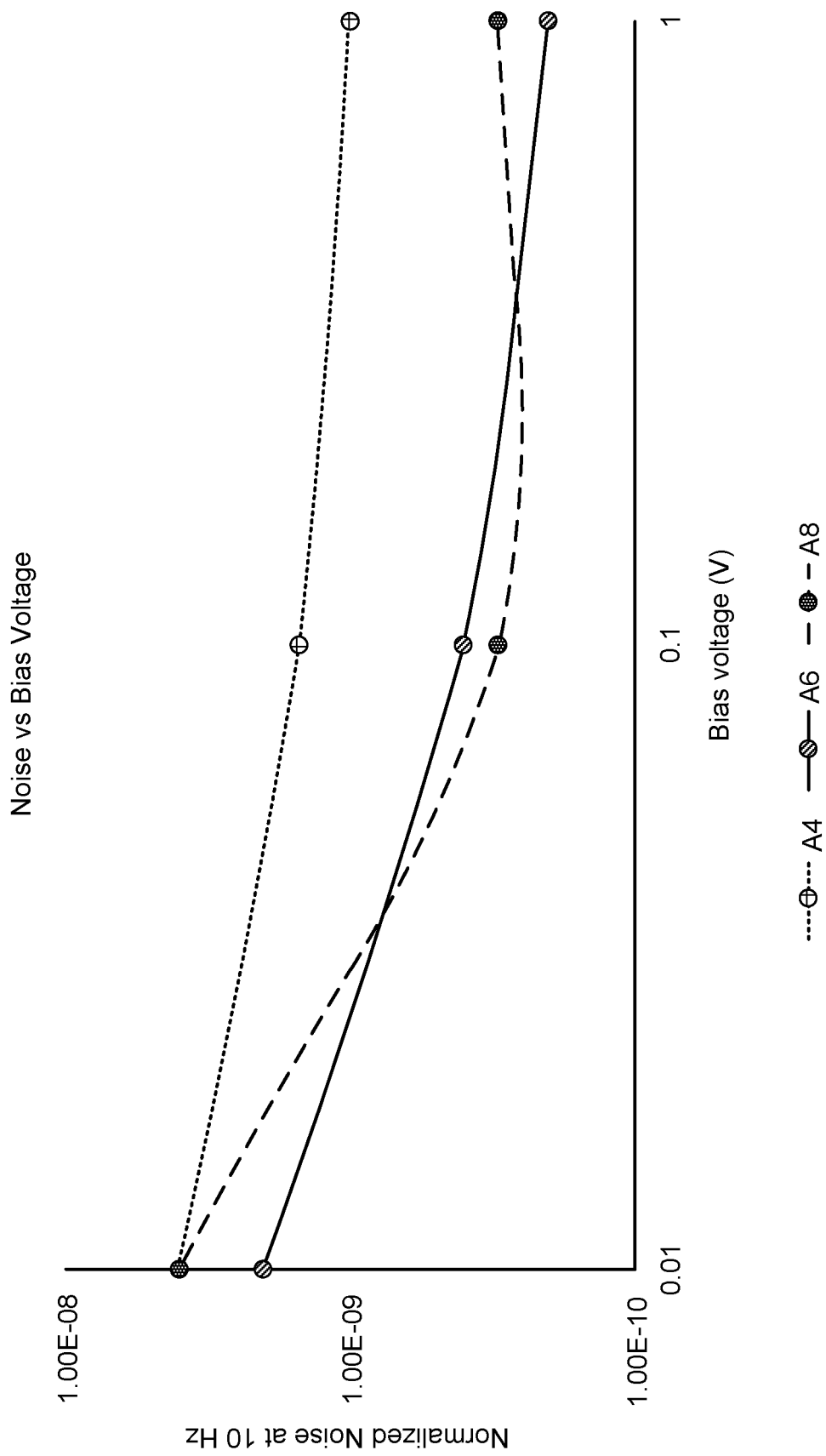
FIG. 7F is a graph of noise vs. bias voltage.
Figure 7G:
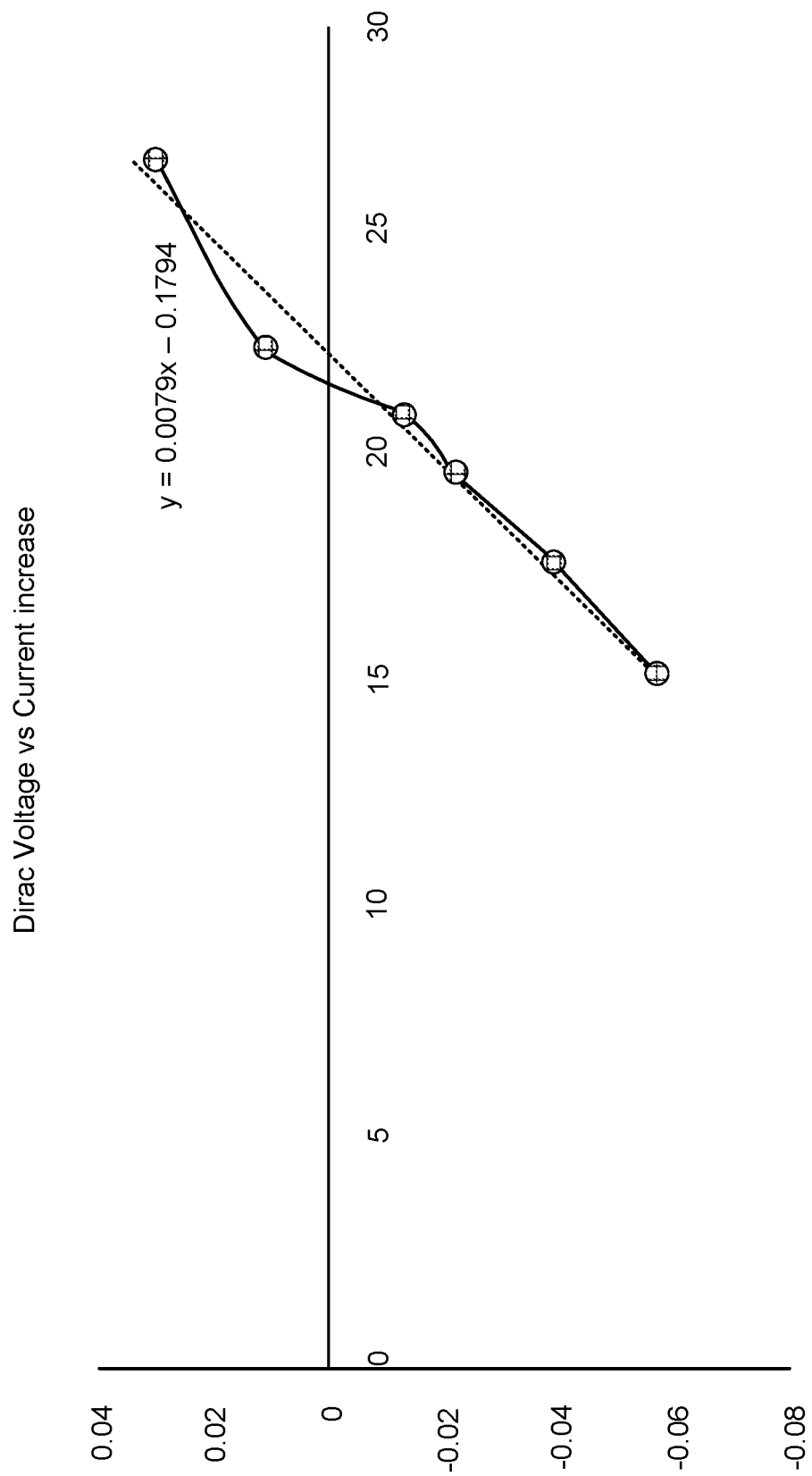
FIG. 7G is a graph of Dirac voltage vs. current increase.

For instance, FIG. 7A depicts a graph of an I-Vg curve for various pH values. Particularly, FIG. 7A illustrates the transfer characteristics of a 20×40 micron graphene-on-SiO2 SGFET ("solution gated FET") at a constant drain-source voltage of Vds=50 mV for different pH values. FIG. 7B depicts a graph of current increase vs. pH increase. Likewise, FIG. 7C depicts a graph of frequency vs. normalized power spectral density for a silicon ISFET device. FIG. 7D illustrates a graph of frequency vs. normalized power spectral density for a typical graphene FET device of the disclosure. Additionally, FIG. 7E depicts a graph of frequency vs. normalized power spectral density for a graphene FET of the disclosure. FIG. 7F depicts a graph of noise vs. bias voltage, and FIG. 7G depicts a graph of Dirac voltage vs. current increase.

Hence, in various aspects of the disclosure, one or more elements and/or methods, as herein described, may be used to shift a reference I-V or I-Vg curve and/or a chemical reaction I-Vg curve so that the difference between the reference I-Vg curve and a chemical reaction I-Vg curve is more pronounced. However, in various embodiments, to make such a difference more pronounced, and thus, better able to be detected, the device may include a further structure 40, such as a membrane or other element that is configured for enhancing the ability of the processor to determine the difference between various I-V and/or I-Vg curves. (See, for instance, FIG. 8A). Particularly, in various embodiments, a further structured layer 4, e.g., a tertiary or quaternary structure, may also be provided, such as where the further structured layer may be included and/or present within the well or chamber, such as to enhance the ability of the processor to determine the difference between the current and/or voltages as well as their respective associated curves. Hence, in one aspect, a chemically-sensitive FET transistor 1 is provided where the FET is fabricated on a primary structure having a stacked configuration including an inorganic base layer 10, e.g., a silicon layer; a dielectric structure and/or an organic or inorganic insulator layer 20, such as a silicon dioxide layer; a 1D, 2D, or 3D material layer 30, such as a carbon nanotube, nanowire, or graphene layer; an oxidation and/or passivation layer 34/36; and further having a conductive source 22 and drain 24 embedded in one or more of the layers, such as between and/or forming a gate structure 26, e.g., a solution gate region 37.

Figure 8B:
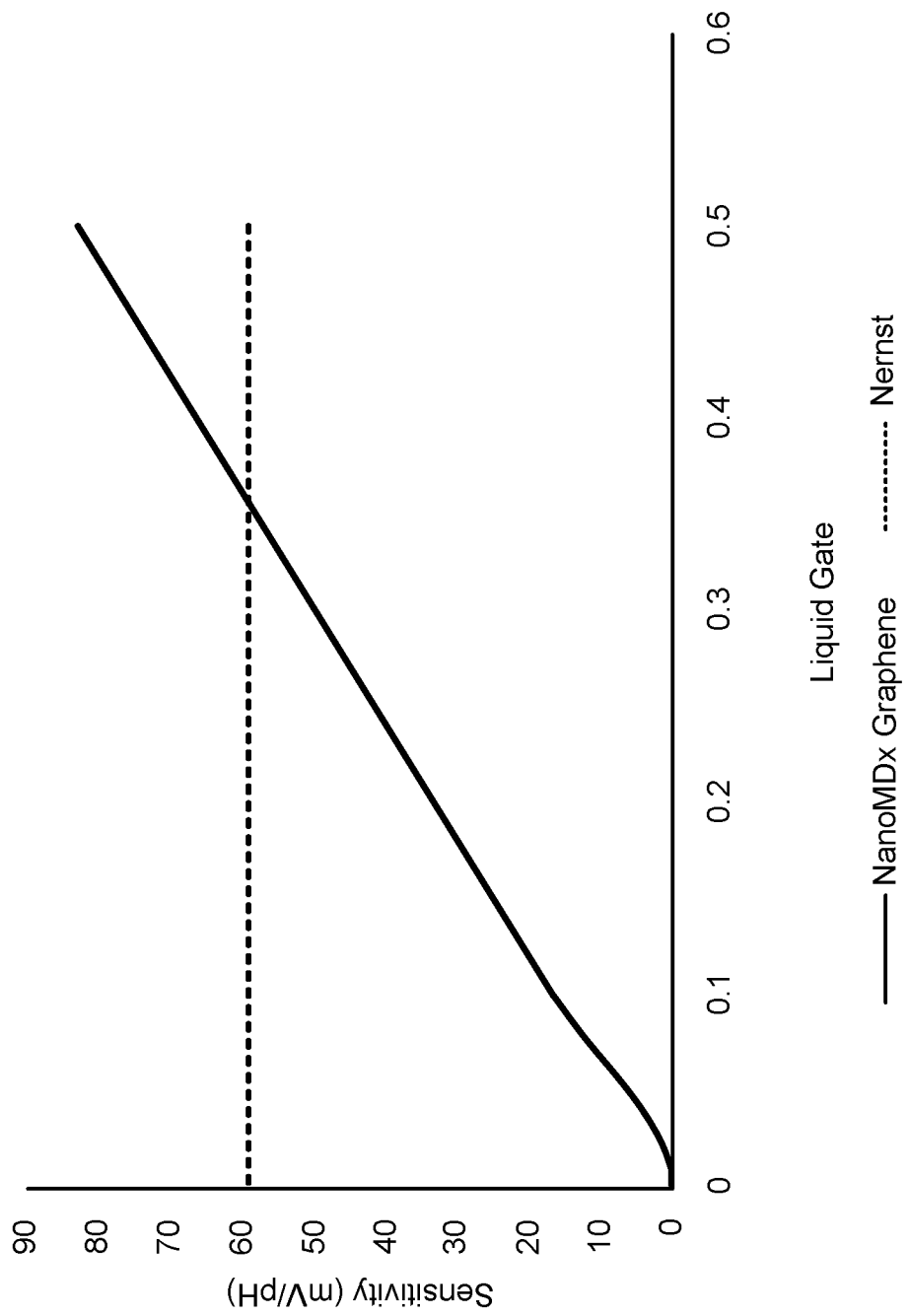
FIG. 8B is a graph of an average sensitivity of a graphene FET ("GFET") calculated as a function of liquid gate potential.

Accordingly, as can be seen with respect to FIG. 8A, in various embodiments, the gate region 26 may be configured so as to form a chamber 37 and/or well 38 and the 1D or 2D material 30 and/or oxidation layers 34 may be positioned between the conductive source 22 and drain 24 in such a manner as to form a bottom surface of the chamber 37. In various instances, the structures may further include or otherwise be associated with an integrated circuit and/or a processor, such as for generating and/or processing generated data, such as sensor derived data. And, further, in various embodiments, the chamber 37 may further include a membrane 40 or other element positioned above or between one or more of the 1D, 2D, or 3D structure layer and/or the oxidation 34 and passivation layers 36, such as where the membrane structure 40 is configured for enhancing the ability of the processor to determine the difference between various I-V and/or I-Vg curves. For instance, FIG. 8B depicts a graph of an average sensitivity of a graphene FET ("gFET") calculated as a function of liquid gate potential. The gFET of the present disclosure surpasses the theoretical 59 mVolt maximum for an ISFET type device made of silicon. This difference is even more pronounced when a ion exclusive membrane 40 is included as part of the device.

In particular embodiments, therefore, as seen with respect to FIGS. 6 and 8, a further structured layer 40, e.g., a secondary or tertiary structure, may also be provided, such as where the further structured layer may be included and/or present within the well or chamber, such as to enhance the ability of the processor to determine the difference between the current and/or voltages as well as their respective associated curves. More particularly, the additional structure may include an ion-selective permeable membrane 40, such as an ion-selective permeable membrane that allows ions of interest to pass through the membrane 40 while blocking other indeterminate ions, such as to enhance the ability of the processor to determine the difference between the reference I-V or I-Vg curve and the chemical reaction I-V or I-Vg curve, and thus enhance the ability of the processor to detect a desired chemical reaction. In various instances, the FET 1 may be configured such that the I-V or I-Vg curve(s) may be shifted so as to better respond to, detect, and/or otherwise determine a biological compound and/or a chemical reaction, such as a biological compound and/or a chemical reaction occurring on the 1D or 2D, e.g., graphene, surface 30 of the chemically-sensitive field effect transistor 1. In particular instances, the ion-selective permeable membrane 40 may include a 2D transistor material, e.g., graphene, which may or may not be electrically connected to the source and/or drain layer and/or channel 26.

Accordingly, in various instances, the chemically-sensitive field effect transistor 1 may be fabricated on an integrated circuit wafer that includes a primary 10 and/or secondary 20 structure as well as a channel structure 26, a processor and/or a tertiary structure 35, such as a structure forming one or more wells 38. For instance, the first and/or secondary structures may include a conductive source 22 and a conductive drain 24, which together with the other components of the FET 1 form a channel region 26. The channel 26 extends from the conductive source 22 to the conductive drain 24, with the channel 26 formed between the two, where a one-dimensional or two-dimensional transistor material layer 30 may be positioned above and/or may otherwise be in contact with the source 22 and drain 24. As indicated above, the FET 1 may include a processor, such as where the processor is configured for generating one or more of a reference I-Vg curve and a chemical reaction I-Vg curve, such as in response to a chemical reaction that is to be detected, for instance, a reaction occurring over or near a reaction zone 26 of the chemically-sensitive field effect transistor 1. In particular embodiments, the processor is configured for determining a difference between the reference I-Vg curve and the chemical reaction I-Vg curve. Hence, in various embodiments, an additional structure 40 may be included, such as a structure that is configured for enhancing the ability of the processor to determine this and other associated differences.

Particularly, in various embodiments, the additional structure may be an ion-selective permeable membrane 40 that allows one or more ions of interest to pass through the membrane 40 while blocking other ions. More particularly, the additional structure 40 may be configured so as to enhance the ability of the processor to determine the difference between the reference I-Vg curve and the chemical reaction I-Vg curve, and thus further enhances the ability of the processor to detect a desired chemical reaction. Accordingly, in various instances, the ion-selective permeable membrane 40 may be positioned within the well 38 and/or over a passivation layer 36, an ion sensitive or reaction layer 34, a 1D and/or a 2D transistor material layer 30, and/or a dielectric layer 35 that itself may be positioned over and/or otherwise form a part of the chamber 37 or channel 26. In certain embodiments, the membrane layer 40 may be or otherwise be associated with an ion getter material, such as an ion getter material that traps ions that may or may not be relevant to the biological species and/or chemical reaction to be sensed and/or determined, such as to enhance the ability of the processor to determine the difference between the reference I-V or I-Vg curve and/or the chemical reaction I-V or I-Vg curve. This may be useful because reducing the number and/or amount of interfering ions, enhances the ability of the processor to detect the desired biological species and/or results of the chemical reactions. Particularly, the ion getter material may be arranged within proximity to the chamber 37 and/or surface 21 thereof so that the action of gettering the unwanted ions improves the detection capability of the chemically-sensitive field effect transistor 1. In some instances, one or more of the various layers herein, such as the ion getter material may be placed over or between one or more of the other layers, such as the dielectric layer 20/35, oxide layer 34, or 2D or 1D layers 30, positioned in proximity to one or more of the chambers, channels, or surfaces of the FET device 1.

In particular instances, the ion-selective permeable structure 40 may include a polymer such as perfluorosulphonic material, a perfluorocarboxylic material, PEEK, PBI, Nafion or PTFE. In other instances, the ion-selective permeable structure may be composed of an inorganic material such as an oxide or a glass. In particular instances, the ion-selective permeable structure 40 may be applied to a surface, e.g., 21, of the FET such as by being deposited thereon, such as by a spincoating, anodization, PVD, or other sol gel methods. An additional material, e.g., HMDS, may also be included so as to manage the interaction of the chamber 37 and/or channel 26 and/or associated oxide layer 20/35 and/or an underlying 2D or 1D transistor layer 30. For instance, a chemically-sensitive field effect transistor 1 of the disclosure may include an additional structure that includes a 2D transistor channel or surface which may include an ion-sensitive material over the channel or surface. In such an instance, the material may be sensitive to ions that are different from the ions associated with the biological molecule or chemical reaction that is to be detected. Particularly, the ion-selective permeable structure 40 may additionally be composed of an ion sensitive 1D or 2D transistor material, such as graphene, that is in addition to the 1D or 2D material layer 30, and is not electrically connected to the channel 26.

In certain instances, the ion-selective permeable structure 40 may be positioned over the ion sensitive layer 30 that itself may be positioned over the channel structure or surface 26. As indicated, the additional structure 40 may be composed of an ion getter material, wherein the ion getter material is configured to trap ions that are not relevant to the chemical reaction to be determined. Accordingly, in some instances, a suitably configured membrane 40 and/or additional structure, e.g., HMDS or other siloxane, may be useful because the action of sensing ions that are different from the ions associated with the biologics and/or chemical reactions that are to be detected allows the processor to filter out the signal from the unwanted ions from the signal of the ions of interest. In particular instances, the HMDS material may be positioned under the graphene. Accordingly, in various instances, an exemplary ion-selective permeable membrane 40 and/or an additional getter structure may be positioned over a channel structure 26, where these structures are configured so as to only allow ions of interest to travel through them. In particular instances, the getter material may be positioned within the chamber 37 or elsewhere on the chip or in the package so as to attract unwanted ions. Another alternative would be to include another ion-selective functional layer(s) over some of the sensors which can detect the presence of contaminants or unwanted ions so that their interaction with the sensor and thus the determination of the sensor reaction to the desired ion can be filtered out.

In all of these instances, the action of trapping ions that are not relevant to the chemical reaction to be determined enhances the ability of the processor to determine the difference between the reference I-V g curve and the chemical reaction I-Vg curve, e.g., because there are fewer interfering ions. In such instances, the membrane 40 and/or ion getter material may be arranged within proximity to a reaction zone 26 that is in proximity to a channel region so that the action of gettering the unwanted ions improves the detection capability of the chemically-sensitive field effect transistor. Alternatively, the ion getter material may be placed over a dielectric layer that is in proximity to one or more of the reaction zones 26 and/or channels.

In another aspect, the present gFET integrated circuits, sensors, and/or arrays of the disclosure may be fabricated such as using any suitable complementary metal-oxide semiconductor (CMOS) processing techniques known in the art. In certain instances, such a CMOS processing technique may be configured to increase the measurement sensitivity and/or accuracy of the sensor and/or array, and at the same time facilitate significantly small sensor sizes and dense gFET chamber sensor regions. Particularly, the improved fabrication techniques herein described employing a 1D, 2D, 3D, and/or oxide as a reaction layer provide for rapid data acquisition from small sensors to large and dense arrays of sensors. In particular embodiments, where an ion-selective permeable membrane is included, the membrane layer may include a polymer, such as a perfluorosulphonic material, a perfluorocarboxylic material, PEEK, PBI, Nafion, and/or PTFE. In some embodiments, the ion-selective permeable membrane may include an inorganic material, such as an oxide or a glass. One or more of the various layers, e.g., the reaction, passivation, and/or permeable membrane layers may be fabricated or otherwise applied by a spin-coating, anodization, PVD, and/or sol gel method.

Accordingly, when using the device for sequencing a nucleic acid sample, the target nucleic acid sample may be coupled to or in proximity with the graphene coated surface of the reaction zone. This template sequence may then be sequenced and/or analyzed by performing one or more of the following steps. For example, a primer, and/or a polymerase, e.g., an RNA and/or DNA polymerase, and/or one or more substrates, e.g. deoxynucleotide triphosphates dATP, dGTP, dCTP, and dTTP, may be added, e.g., sequentially, to the reaction chamber, such as after the hybridization reaction begins so as to induce an elongation reaction. Once the appropriate substrate hybridizes to its complement in the template sequence, there will be a concomitant change in the individual electrical characteristic voltage, e.g., the source-drain voltage (Vsd), measured as a result of the new local gating effect.

Hence, for every elongation reaction with the appropriate, e.g., complementary, substrate there will be a change in the characteristic voltage. For instance, as described herein, a field-effect device for nucleic acid sequencing and/or gene detection is disposed in a sample chamber of a flow cell, and a sample solution, e.g., containing a polymerase and one or more substrates, may be introduced to the sample solution chamber. In various embodiments, a reference electrode may be disposed upstream, downstream or in fluid contact with the field effect device and/or the source and/or drain may themselves serve as electrodes, such as for hybridization detection, and gate voltage may be applied whenever needed.

Particularly, in an exemplary elongation reaction, polynucleotides are synthesized if the added substrate is complementary to the base sequence of the target DNA primer and/or template. If the added substrate is not complementary to the next available base sequence, hybridization does not occur and there is no elongation. Since nucleic acids, such as DNAs and RNAs, have a negative charge in aqueous solutions, hybridization resulting in elongation can be incrementally determined by the change in the charge density in the reaction chamber 30. And because the substrates are added sequentially, it can readily be determined which nucleotide bound to the template thereby facilitating the elongation reaction. Accordingly, as a result of elongation, the negative charge on the graphene gate surface, insulating film surface, and/or the sidewall surface of the reaction chamber will be increased. This increase may then be detected, such as a change in the gate source voltage, as described in detail herein. By determining the addition of which substrate resulted in a signal of change in gate-source voltage, the base sequence identity of the target nucleic acid can be determined and/or analyzed.

More specifically, the field-effect transistor, such as for nucleic acid elongation and/or hybridization detection, may be associated with a buffered solution that is added to the reaction chamber, which can then be used to determine if an elongation reaction has taken place. Particularly, once the template is associated with the substrate, the reaction mixture containing a polymerase, e.g., a Taq polymerase, and a first nucleic acid substrate, e.g., a dATP, is added to the buffer solution to carry out the elongation reaction on the graphene gate coated insulating film of the reaction chamber surface. If the dATP is a complement to the next available reaction site in the isolated template a binding event, e.g., a hybridization reaction, will occur and the antisense strand of the growing sequence will be elongated, and detected by the GFET transistor.

For example, if adenine (A) is complementary to the base thymine (T) on the target template adjacent to the 3'-terminus of the nucleic acid template, an elongation reaction occurs, resulting in synthesis of one adenine. In such instance, the enzyme, Taq DNA polymerase, and the substrate may be washed away from the gate portion and reaction chamber, and a buffer solution, e.g., a phosphoric acid buffer solution, e.g., having a pH of about 6, may be introduced on the graphene gate surface to measure changes in the source-drain voltage. If hybridization has occurred there will be a change in the source-drain voltage and it will be detected. However, if the dATP is not a match, there will be no hybridization, and if no hybridization, there will be no elongation. Consequently, a second reaction mixture containing another, different nucleotide substrate, e.g., dCTP and the enzyme polymerase, and the like will be added to the reaction chamber under conditions suitable for hybridization, which if it occurs will be detected by the GFET. If not, then the steps will be repeated with the next substrate. These steps may be repeated until the nucleic acid sample has been completely sequenced. In various instances, the temperature within the reaction chamber may be controlled, for instance, it may be set to 74° C., such as by using a temperature sensor and/or a heater integrated in the field-effect device.

Consequently, if a hybridization reaction takes place there will be a resultant change to the threshold voltage, which will be increased, e.g., by 4 mV, from before the elongation reaction. The shift of the threshold voltage in the positive direction indicates that a negative charge was generated on the graphene gate surface. It can be understood from this that synthesis of one base caused by the elongation reaction was detectable as a change in threshold voltage. A second elongation reaction may then take place and be repeated until the entire target nucleic acid has been sequenced.

Figure 9A:
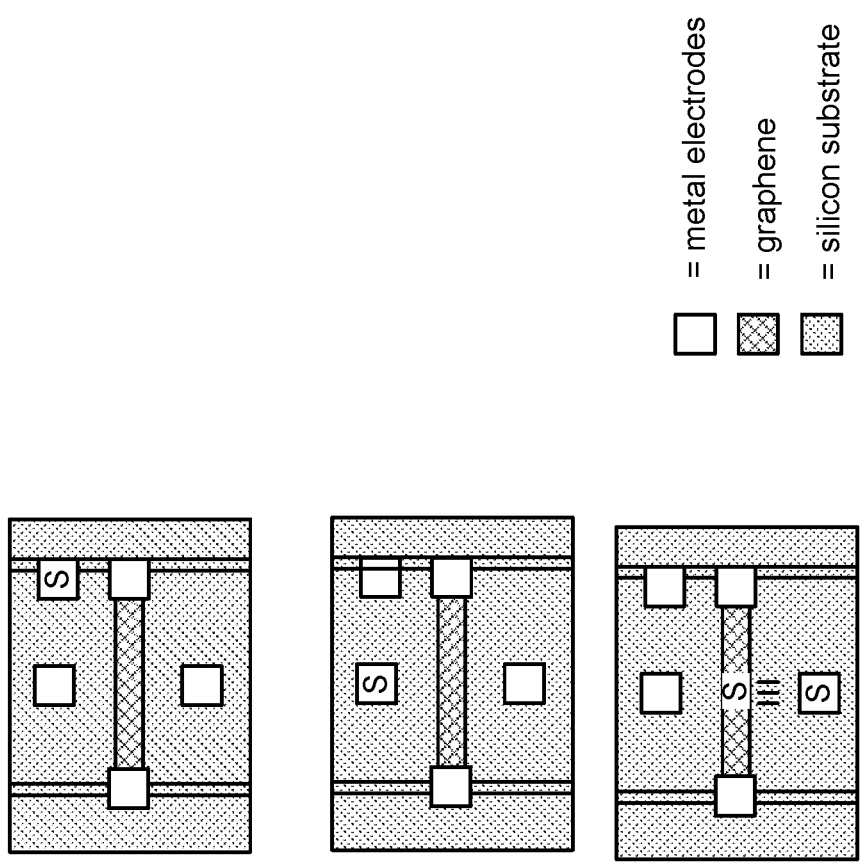
FIG. 9A is an illustration of electrowetting for biomolecule attachment.
Figure 9C:
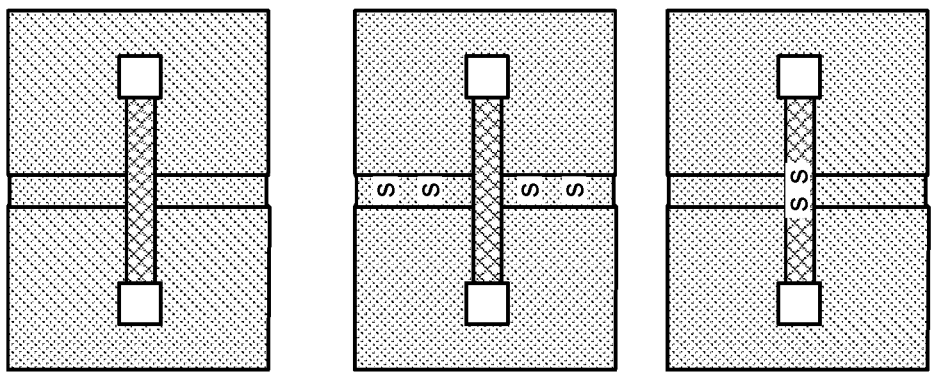
FIG. 9C is an illustration of microfluidics for biomolecule attachment.
Figure 9D:
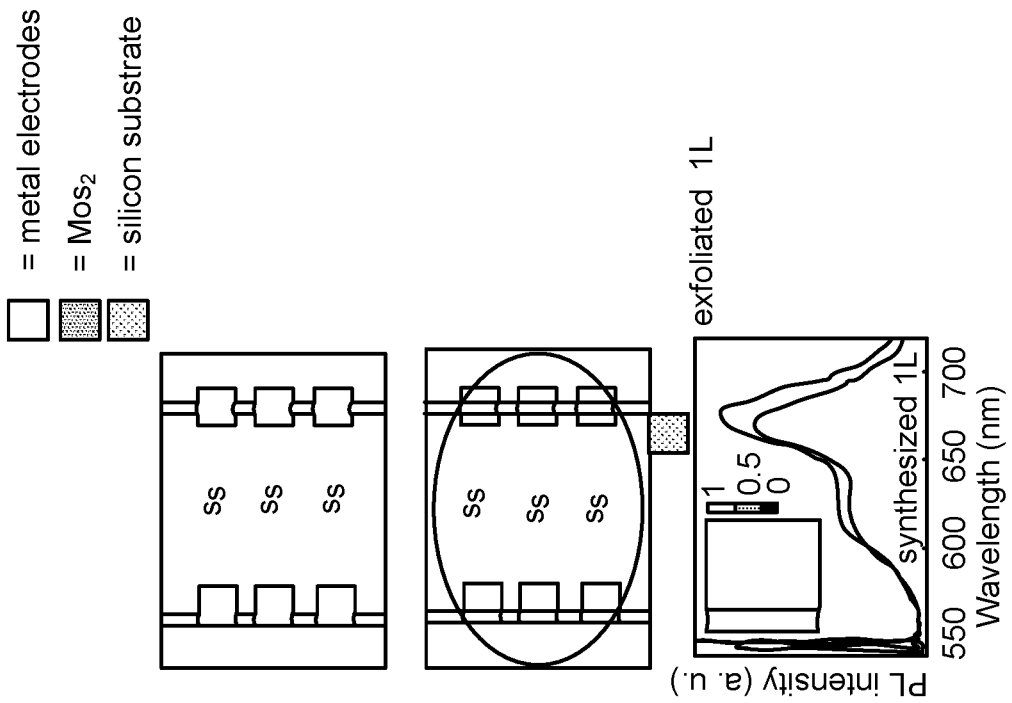
FIG. 9D is an illustration of an optical readout of DNA sequencing using nanomaterials.
Figure 9D:
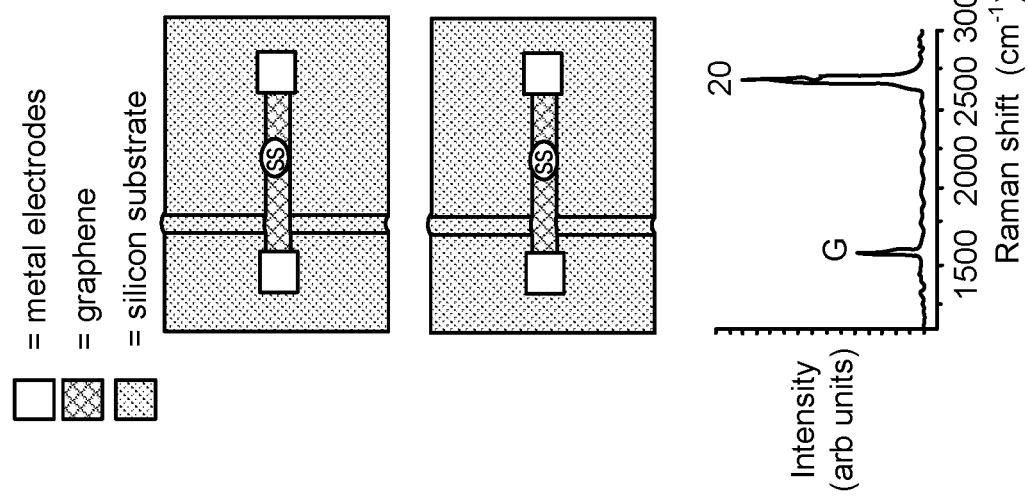

Accordingly, FIG. 9A is an illustration of electrowetting for biomolecule attachment, as disclosed herein. FIG. 9B is an illustration of electrophoresis for biomolecule attachment. FIG. 9C is an illustration of microfluidics for biomolecule attachment. And FIG. 30 is an illustration of an optical readout of DNA sequencing using nanomaterials.

More particularly, in such a configuration as represented in the figures, the drain current of the transistor may be modulated by the electrical charge carried by the nucleotide molecules involved in the hybridization and/or sequencing reactions. For example, after a binding event, the charge in the reaction zone increases resulting in a change in the output current that may be measured. Such a measurement may be made in accordance with the following equation:

More particularly, in such a configuration as represented in the figures, the drain 26 current of the transistor 20 may be modulated by the electrical charge carried by the nucleotide molecules involved in the hybridization and/or sequencing reactions. For example, after a binding event, the charge in the reaction zone increases resulting in a change in the output current that may be measured. Such a measurement may be made in accordance with the following equation:

$$V_{THF} = V_{TH0} - \frac{Q_{com} + Q_0}{C_C + C_F}$$

Such as where $C_C$ represents the current at the control capacitor, and $C_F$ represents the current at the parasitic capacitor. $V_{THF}$ represents the effective threshold voltage of the transistor 20, and $V_{TH0}$ represents the native threshold voltage. $Q_0$ represents the electric charge initially trapped in the floating gate, and $Q_{DNA}$ represents the total charge of hybridization complex.

For instance, a nucleic acid from a sample to be sequenced or representative of a probe to be targeted may be immobilized on the bottom surface or the sidewall of the sample solution well chamber. A Taq DNA polymerase and a nucleotide substrate may then be introduced to the sample solution chamber to induce an elongation reaction. As a result, DNAs may be synthesized along the surface in the vertical or lateral direction, e.g., in parallel to the surface of the graphene coated gate surfaces. In such an instance, as the source-drain current vs gate voltage characteristic changes by the electrostatic interaction with the charged particles (electrons) in the well, and the synthesis of the DNA is in the direction that is transverse or parallel to the graphene gate surface, this keeps the distance between the DNA and the electrons constant, thereby helping to maintain a constant electrostatic interaction. Thus, the base sequence of a template nucleic acid having a large base length can be sequenced and/or analyzed. In other embodiments, a nucleic acid probe may be immobilized on the surface of the reaction zone, as described above, and used in a hybridization reaction so as to detect genetic variation and/or the presence of a genetic disease.

In various instances, in order to conduct parallel analysis of a plurality of nucleic acid templates, the number of the transistors may be equal to or higher than the number and/or types of DNAs to be sequenced and/or analyzed. In certain instances, each nucleic acid template or probe may be an oligonucleotide or a fragment of DNA or RNA that may be constituted from about 100 to about 1000 bases, such as from 200 to about 800 bases, for instance, from about 300 or about 500 bases to about 600 or 700 bases or more or somewhere in between. However, in various instances, a fragment of nucleic acid having 100 bases or fewer may also be used.

Additionally, as indicated above, the present device may also be used in various different DNA/RNA hybridization reactions, such as for the purpose of determining a genetic variation and/or for detecting the presence of a genetic marker for a disease. In such an instance, a nucleic acid probe may be coupled to a bottom or side graphene coated surface of the reaction chamber, per above. As indicated, the probe may be of any suitable length but in various instances from about 5 or 10 to about 1000 bases, such as from 20 or about 50 to about 700 or about 800 bases, for instance, from about 100 or about 200 bases to about 300 bases including about 400 or about 500 bases to about 600 or 700 bases or more or somewhere in between.

For instance, in one exemplary instance, a nucleic acid probe containing about 10 to 15 bases coding for a gene sequence of interest that has been previously amplified, such as by polymerase chain reaction (PCR), may be immobilized on the gate, gate insulating film or side surface of the reaction chamber of the field-effect transistor. For example, once isolated and amplified, the base of the template may be modified so as to be attached to the graphene coated surface, and/or may be coupled to a secondary substrate, such as a glass or plastic bead that has been chemically treated so as to be coupled therewith. Once immobilized, the reaction chamber containing the probes, either on a secondary substrate or directly coupled with a chamber surface, may be reacted with a sample solution containing a number genes including a target gene of interest to be measured such that when a nucleic acid probe having a complementary base sequence to the target gene is immobilized on the gate, gate insulating film or the sidewall surface of the sample solution well structure, or on a secondary substrate immobilized within the reaction chamber of the field-effect device for gene detection, the target gene hybridizes with the nucleic acid probe under appropriate reaction conditions and the target gene and the nucleic acid probe form a double strand, the result of which hybridization reaction may be detected.

Figure 10A:
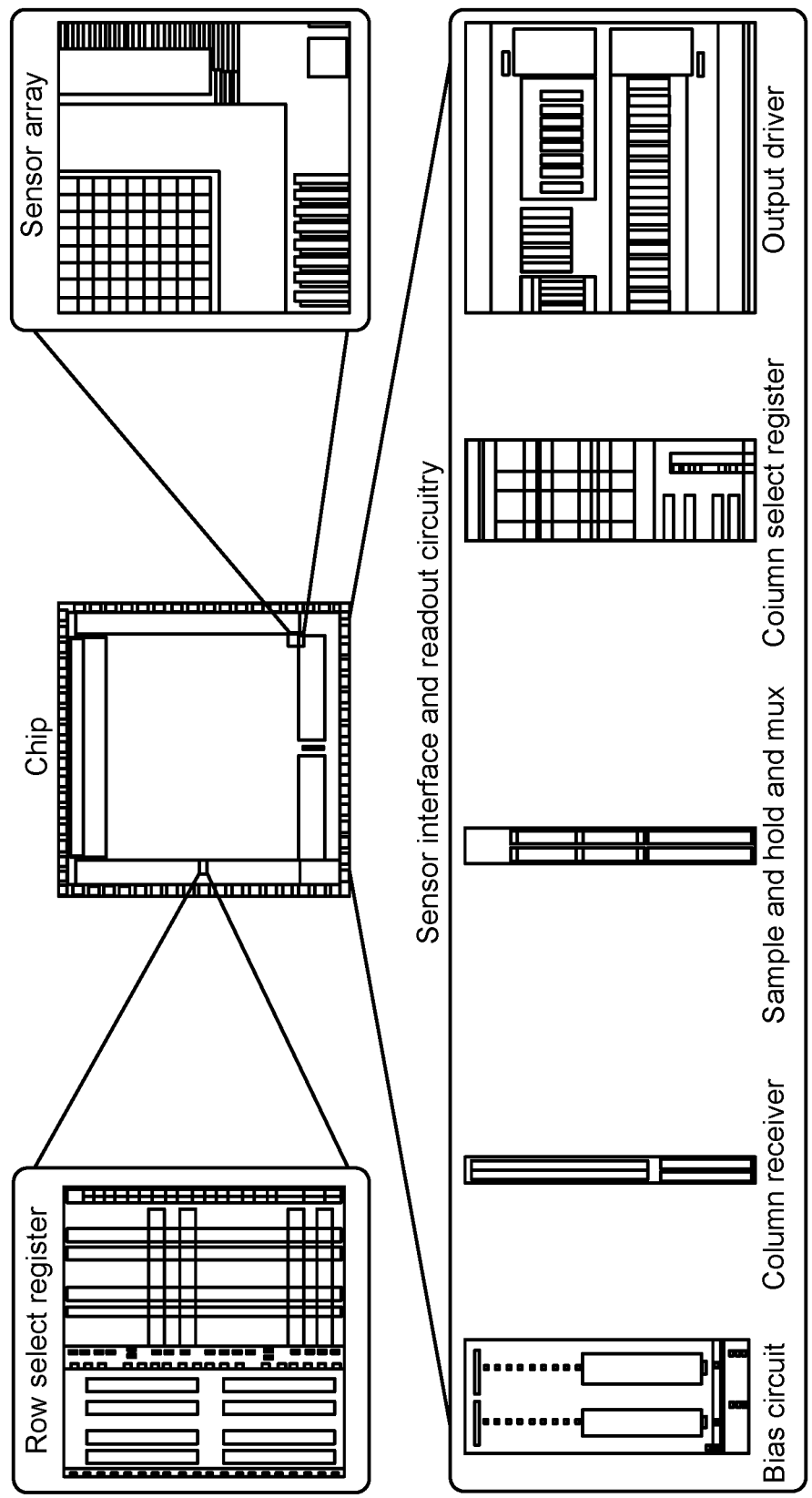
FIG. 10A is a block diagram of components for a system for analysis of biological or chemical materials.

As depicted in FIG. 10A, a gFET array sets forth a two dimensional gFET sensor array chip that in this instance is based on a column and row design, although other designs are also possible. As can be seen with respect to FIG. 10B, the system further includes a row and column decoder, as well as circuitry for performing the requisite sensing, detecting, and processing so as to measure the sensory data. Hence, also included is sensing, measurement, and other associated readout data.

Figure 10B:
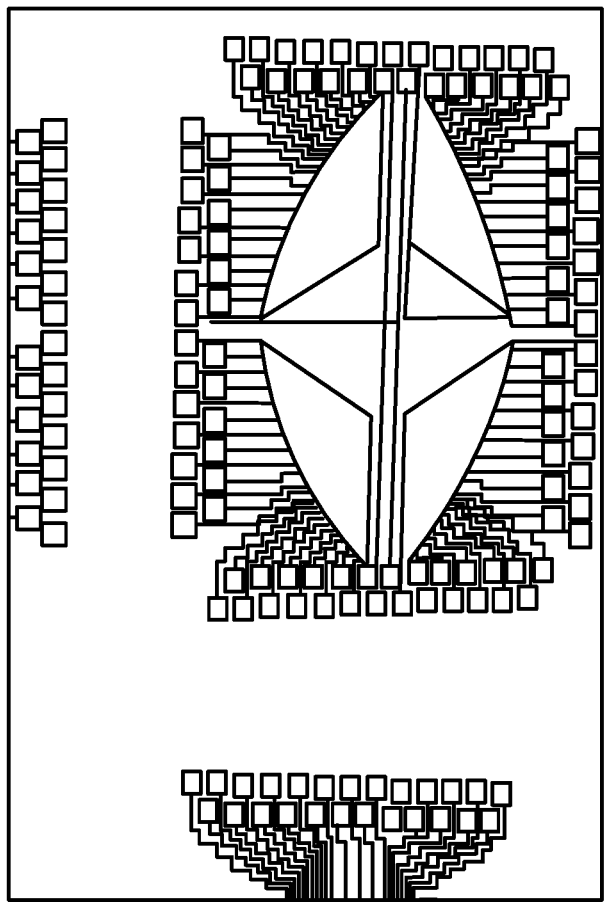
FIG. 10B is an illustration of an exemplary graphene field-effect transistor and chip.
Figure 10B:
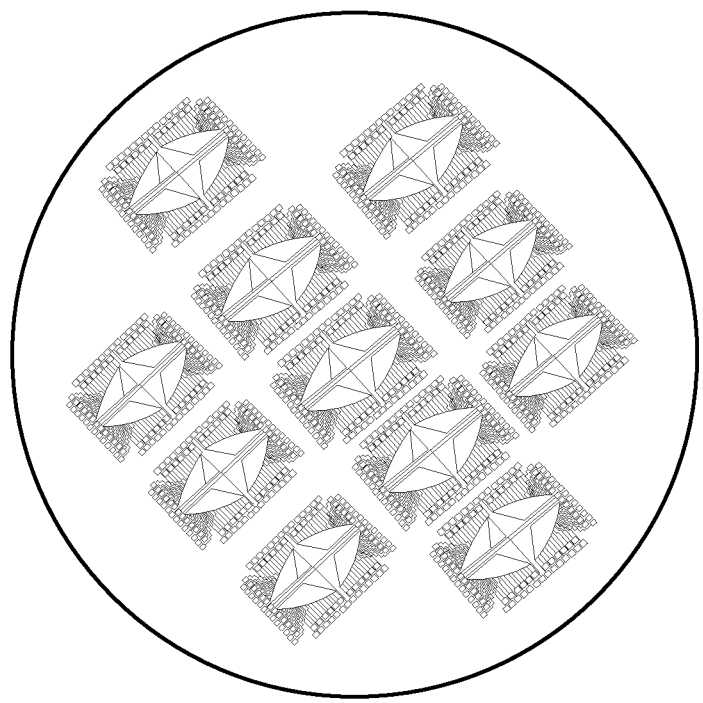

Accordingly, as can be seen with respect to FIGS. 10A and 10B, in various instances, a one or two-dimensional GFET array, as described herein, may be fabricated on a microchip in accordance with the methods herein disclosed. In various instances, the array chip may include a number of GFET sensors that may be arranged in columns and/or rows. A typical number of sensors may include GFET sensor elements, described herein as "sensors," that may be arranged in a 16 sensor by 16 sensor column/row array configuration. As depicted, the array includes two columns, but typically may include sixteen columns, arranged side by side, where each column includes 16 rows. Particularly, each column of the array includes up to 16 sensors. Each column may be configured so as to include a current source $I_{SOURCE}$ that may be shared by all sensors of the column. However, in various other embodiments, each sensor may have its own current source, or the array itself may have a single current source. Additionally, each GFET sensor may include a GFET, as described above, having an electrically coupled source and/or drain and/or body, and may further include one or more switches, such as a plurality of switches S1 and S2 that may be configured so as to be responsive to one of the up to sixteen row select signals (RSEL, and it's complements). More particularly, a row select signal and its complement may be generated simultaneously to "enable" or select a given sensor of the selected column, and such signal pairs may be generated in some sequence to successively enable different sensors of the column, e.g., together or one at a time, such as sequentially.

A row decoder may also be provided as part of the system. In such an instance, the row decoder may be configured so as to provide up to sixteen pairs of complementary row select signals, wherein each pair of row select signals may be adapted so as to simultaneously or sequentially enable one sensor in each column so as to provide a set of column output signals from the array, e.g., based on the respective source voltages VSa through VSb, etc. of the enabled row of GFETs. The row decoder may be implemented as a conventional four-to-sixteen decoder (e.g., a four-bit binary input ROW1-ROW4 to select one of 24 outputs). The set of column output signals VSa through VSb for an enabled row of the array is applied to switching logic, which may be configured to include up to sixteen transmission gates Sa through Sb (e.g., one transmission gate for each output signal).

As above, each transmission gate of the switching logic may be implemented using an n-channel or p-channel MOSFET, in a bottom or top gate configuration, or both to ensure a sufficient dynamic range for each of the output signals $V_{sa}$ through $V_{sb}$. The column decoder, like the row decoder, may be implemented as a conventional four-to-sixteen decoder and may be controlled via the four-bit binary input $COL_1$-$COL_4$ to enable one of the transmission gates Sa through Sb of the switching logic at any given time, so as to provide a single output signal $V_S$ from the switching logic. This output signal $V_S$ may be applied to a 10-bit analog to digital converter (ADC) to provide a digital representation $D_1$-$D_{10}$ of the output signal $V_S$ corresponding to a given sensor of the array.

As noted earlier, individual GFETs and arrays of GFETs such as those discussed above may be employed as sensing devices in a variety of applications involving chemistry and biology. In particular, such GFETs may be employed as pH sensors in various processes involving nucleic acids such as DNA. In general, the development of rapid and sensitive nucleic acid hybridization and sequencing methods, as herein described, e.g., utilizing automated DNA sequencers, may significantly advance the understanding of biology.

It should be noted, that with respect to the various arrays disclosed herein according to various embodiments of the present disclosure may be fabricated according to conventional CMOS fabrication techniques, as described above, as well as modified CMOS fabrication techniques (e.g., to facilitate realization of various functional aspects of the GFET arrays discussed herein, such as additional deposition of graphene and/or other passivation materials, process steps to mitigate trapped charge, etc.) and other semiconductor fabrication techniques beyond those conventionally employed in typical CMOS fabrication (e.g BiCMOS). Additionally, various lithography techniques may be employed as part of an array fabrication process. For example, in one exemplary implementation, a lithography technique may be employed in which appropriately designed blocks are "stitched" together by overlapping the edges of a step and repeat lithography exposures on a wafer substrate by approximately 0.2 micrometers. In a single exposure, the maximum die size typically is approximately 21 millimeters by 21 millimeters. By selectively exposing different blocks (sides, top & bottoms, core, etc.) very large chips can be defined on a wafer (up to a maximum, in the extreme, of one chip per wafer, commonly referred to as "wafer scale integration").

In one embodiment, the array includes 512 columns with corresponding column bias/readout circuitry (one for each column), wherein each column includes geometrically square sensors, each having a size of approximately 9 micrometers by 9 micrometers (e.g., the array may be up to 512 columns by 512 rows). In various instances, the entire array (including sensors together with associated row and column select circuitry and column bias/readout circuitry) may be fabricated on a semiconductor die as an application specific integrated circuit (ASIC), structured ASIC, or as a field gated array, such as having dimensions of approximately 7 millimeters by 7 millimeters.

Various power supply and bias voltages useful for array operation are provided to the array via electrical connections (e.g., pins, metal pads) and labeled for simplicity in block as "supply and bias connections." The array may also include a row select shift register, one or more, e.g., two sets of column select shift registers, and one or more, e.g., two, output drivers, which output drivers are configured to provide two parallel output signals from the array, $V_{outa}$ and $V_{outb}$, representing sensor measurements. The various power supply and bias voltages, control signals for the row and column shift registers, and control signals for the column bias/readout circuitry may be provided by an array controller, which controller may also read the output signals $V_{outa}$ and $V_{outb}$ (and other optional status/diagnostic signals) from the array. Configuring the array such that multiple regions (e.g., multiple columns) of the array may be read at the same time via multiple parallel array outputs (e.g., $V_{outa}$ and $V_{outb}$) facilitates increased data acquisition rates.

Accordingly, in various instances, an integrated circuit for performing a sequencing reaction is provided, such as where the sequencing reaction involves the sequencing of strands of nucleic acids, as described herein. In various instances, the integrated circuit may include a substrate and an array of graphene field effect transistors arranged on the substrate. In such an instance, one or more of, e.g., each, of the graphene field effect transistors may include a primary layer forming a base layer, and a secondary, e.g., intermediary, layer positioned over or otherwise associated with the primary layer, the secondary layer being formed of a first nonconductive material and including a source and a drain formed in the first nonconductive material, the source and drain being separated one from the other by a channel, and being formed of an electrically conductive material. In certain instances, a tertiary layer may be positioned over the secondary layer, such as where the tertiary layer includes a gate formed over the channel to electrically connect the source and the drain. In such an instance, the gate may be formed of a graphene layer. The tertiary layer may additionally include a surface structure that overlaps the source and the drain in the secondary layer, the surface structure further defining a well having side walls and a bottom that extends over at least a portion of the graphene layer of the gate so as to form a reaction chamber for the performance of the sequencing reaction. In particular embodiments, a chemically-sensitive bead provided in one or more wells of the array of graphene field effect transistors, such as where one or more, e.g., each, chemically-sensitive bead may be configured with one or more reactants to interact with portions of the strands of nucleic acids such that the associated graphene field effect transistor detects a change in ion concentration of the reactants by a change in current flow from the source to the drain via an activation of the graphene layer.

It should be noted that, in various embodiments of the array, one or more of the columns, e.g., the first and last columns, as well as the first and/or last sensors of each of the columns may be configured as "reference" or "dummy" sensors. For instance, the dummy sensors of an array, e.g., the topmost metal layer of each dummy sensor may be tied to the same metal layer of other dummy sensors and may be made accessible as a terminal of the chip, which in turn may be coupled to a reference voltage VREF. Such reference voltage VREF may be applied to the bias/readout circuitry of respective columns of the array. In some exemplary implementations, preliminary test/evaluation data may be acquired from the array based on applying the reference voltage VREF and selecting and reading out dummy sensors, and/or reading out columns based on the direct application of VREF to respective column buffers (e.g., via the CAL signal), to facilitate offset determination (e.g., sensor-to-sensor and column-to-column variances) and array calibration.

The calibration data can be stored for each sensor location either just prior to a sequencing session, or preferentially at the end of the device manufacturing process. The calibration data can be stored on-chip in non-volatile memory.

A useful detailed description is set forth in van Rooyen et al., U.S. Patent Publication Number 20140371110 for Bioinformatics Systems, Apparatuses, and Methods Executed On An Integrated Circuit Processing Platform, which is hereby incorporated by reference in its entirety.

A useful detailed description is set forth in van Rooyen et al., U.S. Patent Publication Number 20140309944 for Bioinformatics Systems, Apparatuses, and Methods Executed On An Integrated Circuit Processing Platform, which is hereby incorporated by reference in its entirety.

A useful detailed description is set forth in van Rooyen et al., U.S. Patent Publication Number 20140236490 for Bioinformatics Systems, Apparatuses, and Methods Executed On An Integrated Circuit Processing Platform, which is hereby incorporated by reference in its entirety.

A useful detailed description is set forth in van Rooyen et al., U.S. Patent Publication Number 20140200166 for Bioinformatics Systems, Apparatuses, and Methods Executed On An Integrated Circuit Processing Platform, which is hereby incorporated by reference in its entirety.

A useful detailed description is set forth in McMillen et al., U.S. Provisional Patent Application No. 62/127,232, filed on Mar. 2, 2015, for Bioinformatics Systems, Apparatuses, And Methods Executed On An Integrated Circuit Processing Platform, which is hereby incorporated by reference in its entirety.

A useful detailed description is set forth in van Rooyen et al., U.S. Provisional Patent Application No. 62/119,059, filed on Feb. 20, 2015, for Bioinformatics Systems, Apparatuses, And Methods Executed On An Integrated Circuit Processing Platform, which is hereby incorporated by reference in its entirety.

A useful detailed description is set forth in van Rooyen et al., U.S. Provisional Patent Application No. 61/988,128, filed on May 2, 2014, for Bioinformatics Systems, Apparatuses, And Methods Executed On An Integrated Circuit Processing Platform, which is hereby incorporated by reference in its entirety.

A useful detailed description of a GFET is set forth in van Rooyen, U.S. Provisional Patent Application No. 62/094,016, filed on Dec. 18, 2014, for Graphene FET Devices, Systems, And Methods Of Using The Same For Sequencing Nucleic Acids, which is hereby incorporated by reference in its entirety.

A useful detailed description of a GFET is set forth in Hoffman et al., U.S. Provisional Patent Application No.

62/130,594, filed on Mar. 9, 2015, for Chemically Sensitive Field Effect Transistor, which is hereby incorporated by reference in its entirety.

A useful detailed description of a GFET is set forth in Hoffman et al., U.S. Provisional Patent Application No. 62/130,598, filed on Mar. 9, 2015, for Method And System For Analysis Of Biological And Chemical Materials, which is hereby incorporated by reference in its entirety.

A useful method for growing and transferring graphene is disclosed in Hoffman et al., U.S. Provisional Patent Application No. 62/175,351, filed on Jun. 14, 2015, for a System And Method For Growing And Transferring Graphene For Use As A FET, which is hereby incorporated by reference in its entirety.

A use for two dimensional materials is disclosed in Hoffman et al., U.S. Provisional Patent Application No. 62/175,384, filed on Jun. 14, 2015, for a CMOS Integration Of A Two Dimensional Material, which is hereby incorporated by reference in its entirety.

The following U.S. patent applications discuss the processing component of the a system for analysis of biological and chemical materials: U.S. patent application Ser. No. 14/279,063, titled, Bioinformatics Systems, Apparatuses, and Methods Executed on an Integrated Circuit Processing Platform, filed May 15, 2014; U.S. patent application Ser. No. 14/180,248, titled Bioinformatics Systems, Apparatuses, and Methods Executed on an Integrated Circuit Processing Platform, filed Feb. 13, 2014; U.S. patent application Ser. No. 14/179,513, titled Bioinformatics Systems, Apparatuses, and Methods Executed on an Integrated Circuit Processing Platform, filed Feb. 12, 2014; U.S. patent application Ser. No. 14/158,758, titled Bioinformatics Systems, Apparatuses, and Methods Executed on an Integrated Circuit Processing Platform, filed Jan. 17, 2014; U.S. patent application Ser. No. 14/279,063; U.S. Provisional Application No. 61/826,381, titled System and Method for Computation Geneomic Pipeline, filed May 22, 2013; U.S. Provisional Application No. 61/943,870, titled Dynamic Genome Reference Generation For Improved NGS Accuracy And Reproducibility, filed Feb. 24, 2014; all of which are hereby incorporated by reference in their entireties herein.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

The invention claimed is:

1. A chemically-sensitive field effect transistor having a multi-layered structure for chip fabrication, the field effect transistor comprising:
    a substrate layer having an extended body;
    a first insulating layer positioned above the extended body of the substrate layer;
    a second insulating layer positioned above the first insulating layer, wherein the second insulating layer is configured to form one or more side wall members of a well for a fluid containing an analyte;
    a source electrode and a drain electrode each having a top surface and a bottom surface, the top surface separated from the bottom surface by opposing outer and inner side portions, each of the opposed side portions and each of the bottom surfaces of the source and drain electrodes being disposed within or over the first insulating layer, the source electrode being separated from the drain electrode by a distance;
    a graphene layer comprising a two-dimensional (2D) monolayer of carbon atoms arranged as a lattice structure and positioned above the first insulating layer and forming a channel between the source electrode and drain electrode; and
    a solution gate region configured to form a solution gate above the channel in response to the fluid being flowed over the channel of the graphene layer at the bottom of the opening of the well, wherein the solution gate is configured to enable a set of measurements to be made to determine differences between individual I-Vg curves comprising a first I-Vg curve that serves as a reference curve and a second I-Vg curve having a shifted and changed shape relative to the reference curve based on characteristics of the analyte present in the fluid being flowed over to have direct fluidic contact with the channel of the 2D graphene layer, wherein each I-Vg curve comprises a p-type portion and an n-type portion and wherein the set of measurements for the individual I-Vg curves includes:
        an on-state drain current (Ion) measurement taken from a p-type portion of the I-Vg curve;
        a first transconductance measurement taken at the steepest and/or flattest sections of the p-type portion of the I-Vg curve;
        a Dirac voltage ($V_{Dirac}$) measurement taken at a lowest point of the I-Vg curve;
        a second transconductance measurement taken at the steepest and/or flattest sections of the n-type portion of the I-Vg curve; and
        an on-state drain current (Ion) measurement taken from the n-type portion of the I-Vg curve.

2. The chemically-sensitive field effect transistor according to claim 1, further comprising one or more ion-selective permeable membrane layers positioned over the channel of the graphene layer and configured to allow one or more ions of interest to pass through the membrane while blocking other ions.

3. The chemically-sensitive field effect transistor according to claim 2, wherein the one or more ion-selective membrane layers comprise polymer material selected from perfluorosulphonic material, perfluorocarboxylic material, polyetheretherketone (PEEK), polybenzimidazole (PBI), sulfonated tetrafluoroethylene based fluoropolymer-copolymer (Nafion®), and/or polytetrafluoroethylene (PTFE).

4. The chemically-sensitive field effect transistor according to claim 3, wherein the one or more ion-selective permeable membrane layers are physically deposited on to the channel of the graphene layer by spincoating or physical vapor deposition (PVD).

5. The chemically-sensitive field effect transistor according to claim 2, further comprising a getter material arranged within the well and configured to trap unwanted ions, contaminants, and/or other impurities.

6. The chemically-sensitive field effect transistor according to claim 1, wherein the second insulating layer blocks the fluid from contacting the source electrode or the drain electrode.

7. The chemically-sensitive field effect transistor according to claim 6, wherein the second insulating layer is composed of a polymer, polyimide, or benzocyclobutene (BCB), a silicon oxide, a silicon nitride, a silicon oxynitride, or a silicon carbide.

8. A biosensor chip comprising:
a plurality of chemically-sensitive field effect transistors, individually having:
a multi-layered structure configured to perform a set of measurements of a biological reaction involving a binding event of one or more label-free biological analytes, the field effect transistors individually comprising:
a substrate layer having an extended body;
a first insulating layer positioned above the extended body of the substrate layer;
a source electrode and a drain electrode disposed in or over the first insulating layer, the source electrode separated from the drain electrode by a distance;
a second insulating layer positioned above the first insulating layer and proximate the source and drain electrodes, wherein the second insulating layer forms two or more side wall members of a well for a fluid comprising the analyte;
a graphene layer comprising a two-dimensional (2D) monolayer of carbon atoms arranged as a lattice structure and positioned at a bottom of an opening of the well and above the first insulating layer and extending between the source and drain electrodes thereby forming a channel between the source electrode and drain electrode; and
a solution gate region configured to form a solution gate above the channel in response to the fluid being flowed over the channel of the graphene layer at the bottom of the opening of the well, wherein the solution gate is configured to enable the set of measurements to be made to determine differences between individual I-Vg curves comprising a first I-Vg curve that serves as a reference curve and a second I-Vg curve having a shifted and changed shape relative to the reference curve based on characteristics of the analyte present in the fluid being flowed over to have direct fluidic contact with the channel of the 2D graphene layer, wherein each I-Vg curve comprises a p-type portion and an n-type portion and wherein the set of measurements for the individual I-Vg curves includes:
an on-state drain current (Ion) taken from a p-type portion of the I-Vg curve;
a first transconductance measurement taken at the steepest and/or flattest sections of the p-type portion of the I-Vg curve;
a Dirac voltage ($V_{Dirac}$) measurement;
a second transconductance measurement taken at the steepest and/or flattest sections of the n-type portion of the I-Vg curve; and
an on-state drain current (Ion) taken from the n-type portion of the I-Vg curve.

9. The biosensor chip according to claim 8, wherein the multi-layered structure of one or more transistors of the plurality of chemically sensitive transistors further comprises one or more ion-selective permeable membrane layers positioned over the channel of the graphene layer and configured to allow one or more ions of interest to pass through the membrane while blocking other ions.

10. The biosensor chip according to claim 9, wherein the one or more ion-selective membrane layers comprise polymer material selected from perfluorosulphonic material, perfluorocarboxylic material, polyetheretherketone (PEEK), polybenzimidazole (PBI), sulfonated tetrafluoroethylene based fluoropolymer-copolymer (Nafion®), and/or polytetrafluoroethylene (PTFE.

11. The biosensor chip according to claim 10, wherein the one or more ion-selective permeable membrane layers are physically deposited on to the channel of the graphene layer by spincoating or physical vapor deposition (PVD).

12. The biosensor chip according to claim 11, further comprising a getter material arranged within the well and configured to trap unwanted ions, contaminants, and/or other impurities.

13. The biosensor chip according to claim 9, wherein the second insulating layer blocks the fluid from contacting the source electrode or the drain electrode.

14. A system comprising:
a biosensor chip having a plurality of chemically-sensitive field effect transistors, the individual chemically-sensitive field effect transistors having a multi-layered structure for determining characteristics of one or more analytes contained in a fluid flowed over a channel of the field effect transistor, the field effect transistor comprising:
a substrate layer having an extended body;
a first insulating layer positioned above the extended body of the substrate layer;
a source electrode and a drain electrode positioned in or over the first insulating layer, the source electrode and the drain electrode being separated by a distance;
a second insulating layer positioned above the first insulating layer and proximate the source and drain electrodes, wherein the second insulating layer is configured to form one or more side wall members of a well for the fluid containing the analyte;
a graphene layer comprising a two-dimensional monolayer of carbon atoms arranged as a lattice structure and positioned between the first and second insulating layers and substantially extending between an outer side portion of the drain electrode and an outer side portion of the source electrode to form a channel between the source and drain electrodes;
a solution gate region configured to form a solution gate above the channel in response to the fluid being flowed over the channel of the graphene layer at the bottom of the opening of the well, wherein the solution gate is configured to enable a set of measurements to be made to determine differences between individual I-Vg curves comprising a first I-Vg curve that serves as a reference curve and a second I-Vg curve having a shifted and changed shape relative to the reference curve based on characteristics of the analyte present in the fluid being flowed over to have direct fluidic contact with the channel of the 2D graphene layer, wherein each I-Vg curve comprises a p-type portion and an n-type portion and wherein the set of measurements for the individual I-Vg curves includes:
an on-state drain current (Ion) measurement taken from a p-type portion of the I-Vg curve;
a first transconductance measurement taken at the steepest and/or flattest sections of the p-type portion of the I-Vg curve;
a Dirac voltage ($V_{Dirac}$) measurement;
a second transconductance measurement taken at the steepest and/or flattest sections of the n-type portion of the I-Vg curve; and
an on-state drain current (Ion) measurement taken from the n-type portion of the I-Vg curve.

15. The system of claim 14, further comprising a processor wherein the multi-layered structure of the individual chemically sensitive field effect transistors is configured to enable the processor to measure for the individual chemically sensitive field effect transistors a shift and a change of a plurality of characteristics of the first I-Vg curve that serves as a reference curve and of the second I-Vg curve to detect differences from the reference curve based on characteristics of the analyte in the well.

16. The system according to claim 15, further comprising one or more ion-selective permeable membrane layers positioned over the channel of the graphene layer and configured to allow one or more ions of interest to pass through the membrane while blocking other ions.

17. The system according to claim 16, wherein the one or more ion-selective membrane layers comprise polymer material selected from polyetheretherketone (PEEK), polybenzimidazole (PBI), sulfonated tetrafluoroethylene based fluoropolymer-copolymer (Nafion®), and/or polytetrafluoroethylene (PTFE).

18. The system according to claim 15, wherein the one or more ion-selective permeable membrane layers are physically deposited on to the channel of the graphene layer by spincoating or physical vapor deposition (PVD).

19. The system according to claim 15, further comprising a magnetic field generator corresponding to the individual wells and configured to selectively position a proximity of one or more beads having the one or more analytes attached, to the channel of the individual transistors within the individual wells of the biosensor chip.

20. The system according to claim 19, wherein the one or more analytes involve a plurality of biological materials selected from the group consisting of a nucleotide, nucleic acid, and a protein, and the processor is configured to detect differences in the position and shape of individual I-Vg curves detected in response to one or more analytes attached to the beads.

* * * * *